(12) United States Patent
Dutta et al.

(10) Patent No.: US 6,375,954 B1
(45) Date of Patent: *Apr. 23, 2002

(54) SIZE-VARIABLE STRAIN-SPECIFIC PROTECTIVE ANTIGEN FOR POTOMAC HORSE FEVER

(75) Inventors: Sukanta Dutta, Glenn Dale; Biswajit Biswas, Greenbelt, both of MD (US); Ramesh Vemulapalli, Blacksburg, VA (US)

(73) Assignee: University of Maryland College Park, College Park, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/157,257

(22) Filed: Sep. 18, 1998

Related U.S. Application Data

(60) Provisional application No. 60/059,252, filed on Sep. 18, 1997.

(51) Int. Cl.$^7$ .............................................. A61K 39/02
(52) U.S. Cl. ................................ 424/234.1; 424/184.1; 424/185.1; 424/191.1; 424/265.1; 530/350.1
(58) Field of Search ....................... 530/350; 424/265.1, 424/184.1, 185.1, 191.1, 234.1

(56) References Cited

U.S. PATENT DOCUMENTS 4,759,927 A    7/1988   Dutta

OTHER PUBLICATIONS

"Molecular Basis of Antigenic Variation of Strain Specific Surface Antigen Gene of *Ehrlichia Risticii* and Development of a Multiplex PCR Assay for Differentiation of Strains", By Biswajit Biswas, Dissertation submitted to the Faculty of the Graduated School of the University of Maryland at College Park (1996) (Abstract).

"Molecular Analysis of Differences Between Two Strains of *Ehrlichia Risticii* and Identification of Protective Antigen", by Ramesh Vemulapalli, Dissertation to the Faculty of the Graduated School of the University of Maryland at College Park (1996) (Abstract).

Ramesh Vemulapalli et al, "Studies with Recombinant Proteins Of *Ehrlichia Risticii*: Identification of Strain–Specific Antigen as a Protective Antigen", Veterinary Parasitology, vol. 76, pp. 189–202, 1998.

Sukanta Dutta et al, "Association of Deficiency in Antibody Response to Vaccine and Heterogeneity Of *Ehrlichia Risticii* Strains with Potomac Horse Fever Vaccine Failure in Horses", Journal of Clinical Microbiology, vol. 36, No. 2, pp. 506–512, Feb. 1998.

Vemulapalli et al. J. Clin. Microbiol. Nov. 1995. 33(11): 2987–2993.*

Shankarappa et al. Internatl. J. System. Bacteriol. Jan. 1992. 42(1): 127–132.*

Kaylor et al. Infect. Immun. Jun. 1991. 59(6): 2058–2062.*

Shankarappa et al. Infect. Immun. Feb. 1992. 60(2): 612–617.*

* cited by examiner

*Primary Examiner*—Jennifer E. Graser
(74) *Attorney, Agent, or Firm*—Arent Fox Kintner Plotkin Kahn PLLC

(57) ABSTRACT

An isolated and purified antigen which is expressed by a wild-type *E. risticii* strain and is specific to the strain. The present invention also relates to nucleic acid constructs which encode the antigen, expression vectors, transformed host cells, and methods for producing the antigen.

3 Claims, 14 Drawing Sheets

Fig.1

Primer Sequences for PCR amplification of any SSA gene.

Primer names ECP 1 and ECP 2 [Expression cloning Primer (ECP)]

ECP 1 => 5'CAT AAA ATT TCT AAG ACG AAG GAT CCC TAT GTC 3'

ECP 2 => 5'GAG AGA AAG TTC CCC GTG TGA ATT CTA GCT AGG 3'

Fig.2A

```
                                              -35                  -10    +1
ATTGGATCTAAATAATGTACACTGGAGGTTCGTATTTTCTATTATGAAAGGGATAGA  57
ATGTTAAATTTTATGATTTTTTATAATAAAAATAGATATAAAATTTAGTAGTTTTAT 114
AAATTTTTCATAACAAAGGACTATCCTCCTTGCATAAAATTTCTAAGACGAAAAATC 171
                                                                                                                        RBS
CCTATGTCAAATGAAACACTTTTGAGCGTACTTTCTGATGAAACGCACTTTGCTAAT 228
  M   S   N   E   T   L   L   S   V   L   S   D   E   T   H   F   A   N
CTAGTTGATGAACTTCTTCTCATCTTGGTTAAAGACAGTATTTTCACTCAAGTAATA 285
  L   V   D   E   L   L   L   I   L   V   K   D   S   I   F   T   Q   V   I
AAAGGCGAGGGAAAGACAGAATTAAAAGACATACTTACAGACAACACTGGTAAGTTT 342
  K   G   E   G   K   T   E   L   K   D   I   L   T   D   N   T   G   K   F
AAAGAACTTATAGAAAGTGCAGGTAAAGACATACTAAAAGAGATACTTACAGACAAT 399
  K   E   L   I   E   S   A   G   K   D   I   L   K   E   I   L   T   D   N
ACCGGCAATTTTAAAGGACTTATAGAAGGTAATGGTAAGACGGAGGCAAAAGAGGTA 456
  T   G   N   F   K   G   L   I   E   G   N   G   K   T   E   A   K   E   V
CGCACTAATGAAAAATTCAAGGAGCTTTTTGGAAGCAATGGTAAGGACATACTGAAA 513
  R   T   N   E   K   F   K   E   L   F   G   S   N   G   K   D   I   L   K
GACATTCTTACTGATAACACCGGTAACTTTAAAGGCCTTATAGAAAGTGCAGCTAAG 570
  D   I   L   T   D   N   T   G   N   F   K   G   L   I   E   S   A   A   K
GGTAAGCTGAAAGATCTTCTTATTGATGAAAAATTTCAAAAATTATTCGAGGATGAA 627
  G   K   L   K   D   L   L   I   D   E   K   F   Q   K   L   F   E   D   E
ACGAAAGCTGGTCGTGTAAAAGAAATACTTACAGACAGCAACGCTAAGGAAATACTC 684
  T   K   A   G   R   V   K   E   I   L   T   D   S   N   A   K   E   I   L
ACAAATGAAGTAGCAAAAGAGGTACTAAAATCCGATAAATTCAAGGAGGCAATAACT 741
  T   N   E   V   A   K   E   V   L   K   S   D   K   F   K   E   A   I   T
GGCGATGGTAAGGACGCACTAAAAGAGATACTTACTTGTGATAAATTTAAAGAGGCT 798
  G   D   G   K   D   A   L   K   E   I   L   T   C   D   K   F   K   E   A
GTAACAGGCAATGGTAAAGACATACTAAAAGGTATACTTACAGATAGCACTGGTAAA 855
  V   T   G   N   G   K   D   I   L   K   G   I   L   T   D   S   T   G   K
TTTAAAGAACTTATAGAAAGTACTAGTAAAGACATACTAAAAGAGATACTTACAGAT 912
  F   K   E   L   I   E   S   T   S   K   D   I   L   K   E   I   L   T   D
AATACCGGTAACTTTAAAGGCCTTATAGAAAGCACTGGCAAGGAGAAAGTAAAAGAA 969
  N   T   G   N   F   K   G   L   I   E   S   T   G   K   E   K   V   K   E
CTTCTTATCGATGGGAAGTTTAAGGACCTGTTTACTGATGCAACAAAAGCCGGTTAT 1026
  L   L   I   D   G   K   F   K   D   L   F   T   D   A   T   K   A   G   Y
GTAAAAGAAATACTCACGAACGATACAGCTAAGGAAGTACTTACAGATCAAACAGCA 1083
  V   K   E   I   L   T   N   D   T   A   K   E   V   L   T   D   Q   T   A
AAGGAGGTCCTAAAAGATAGTACAGCTAAAGACATATTAAAGGACACAAACGCAGCT 1140
  K   E   V   L   K   D   S   T   A   K   D   I   L   K   D   T   N   A   A
GCGGTACTAAAAAACAGCACAGCTAAAGAAATACTTACAAACCAAACCGCTAAAGAA 1197
  A   V   L   K   N   S   T   A   K   E   I   L   T   N   Q   T   A   K   E
GTGCTTACAGATGGTACATCCAAAGAAGTACTAAAAGAGATACTTACTTGTGATAAA 1254
  V   L   T   D   G   T   S   K   E   V   L   K   E   I   L   T   C   D   K
TTTAAAGAGGCAGTAACAGGAGATGGTAAAGACATACTAAAAGGTATACTTACAGAT 1311
  F   K   E   A   V   T   G   D   G   K   D   I   L   K   G   I   L   T   D
AGCACTGGTAAGTTTAAAGAACTTATAGAAAGTACTGGTAAAGACATACTGAAAGAC 1368
  S   T   G   K   F   K   E   L   I   E   S   T   G   K   D   I   L   K   D
```

Fig.2B

```
ATTCTTACAGATAGCACTGGTAAATTTAAAGAACTTATAGAAGTACTGGTAAAGAAC 1425
 I  L  T  D  S  T  G  K  F  K  E  L  I  E  V  L  V  K  N
AAGCTAAAAGAGATTCTTACAGATAACACCGGTAACTTCAAAGGGCTTGTAGAAGGC 1482
 K  L  K  E  I  L  T  D  N  T  G  N  F  K  G  L  V  E  G
GCCGGGAAGGATGAAGCAAAAGCAGTACTTACTGACGAGAAATTTAAAGGCTTGTTT 1539
 A  G  K  D  E  A  K  A  V  L  T  D  E  K  F  K  G  L  F
GATGACAAAACAATAGCTGGCTATGTAAAAGAAATACTCACCAGCGAGAAGTTTAAA 1596
 D  D  K  T  I  A  G  Y  V  K  E  I  L  T  S  E  K  F  K
AAACTGTTTGAAAGTGCAGGTAAGACTAAAGTAAAAGAACTCCTCATTGATGAGAAG 1653
 K  L  F  E  S  A  G  K  T  K  V  K  E  L  L  I  D  E  K
TTTCAAAAATTATTTGAGGATGACACGAAAGCCAGTCATGTAAAAGAAATACTCACG 1710
 F  Q  K  L  F  E  D  D  T  K  A  S  H  V  K  E  I  L  T
AACGATACAGCTAAGGAAATACTTACAGATCAAACAGCTAAAGAAGTCCTAAAGGAT 1767
 N  D  T  A  K  E  I  L  T  D  Q  T  A  K  E  V  L  K  D
AGTACAGCTAAAGAGATATTAAAGGACACAAACGCAGCTGCGCTACTAAAAGACAGC 1824
 S  T  A  K  E  I  L  K  D  T  N  A  A  A  L  L  K  D  S
ACAGCAAAAGAGGTACTAAAATCCGATAAATTTAAAGATGCAATAACTGGTGCTGGT 1881
 T  A  K  E  V  L  K  S  D  K  F  K  D  A  I  T  G  A  G
AAGGACGCACTAAAAGAGATACTTACTTGTGATAAATTTAAAGAGGCAGTAACAGGC 1938
 K  D  A  L  K  E  I  L  T  C  D  K  F  K  E  A  V  T  G
AATGGTAAAGACATACTAAAAGGTATACTTACAGATAGCACTGGTAAATTTAAAGAG 1995
 N  G  K  D  I  L  K  G  I  L  T  D  S  T  G  K  F  K  E
CTAATAGAAAGCACTGGTAAGGATAAGCTAAAAGAGATTCTTACAGATAACACCGGT 2052
 L  I  E  S  T  G  K  D  K  L  K  E  I  L  T  D  N  T  G
AACTTTAAATTTCTTGTAGAAGGCGCCGGTAAGGATGAAGCAAAAGCAGTACTTACT 2109
 N  F  K  F  L  V  E  G  A  G  K  D  E  A  K  A  V  L  T
CACGAGAAATTTAAAGACTTGTTTAATGTCAAAACAACAGCTGGCTACGTGAAAGAA 2166
 H  E  K  F  K  D  L  F  N  V  K  T  T  A  G  Y  V  K  E
ATACTTACCAGCGACAAGTTTAAAGAACTGTTTACTGATGCAACAAAAGCTGGCTAC 2223
 I  L  T  S  D  K  F  K  E  L  F  T  D  A  T  K  A  G  Y
GTGAAAGAAATACTCACGAACGATACAGCTAAGGAAATACTTACAGATCAAACAGCT 2280
 V  K  E  I  L  T  N  D  T  A  K  E  I  L  T  D  Q  T  A
AAAGAAGTCCTAAAGGATGGTACAGCTAAAGACATATTAAAGGACACAAACGCACGT 2337
 K  E  V  L  K  D  G  T  A  K  D  I  L  K  D  T  N  A  R
GCGCTACTAAAAGACAGCACAGCCAAAGAAGTACTAAAATGCGATAAATTTAAGGAA 2394
 A  L  L  K  D  S  T  A  K  E  V  L  K  C  D  K  F  K  E
GCAATAACAGGTGCCGGTAAAGATGAGCTAAAATACATACTCACTAATAGCGAGTTT 2451
 A  I  T  G  A  G  K  D  E  L  K  Y  I  L  T  N  S  E  F
AAAAGCTTATTTCATAGCAAAGATAGCGCTGAAGCTGTTAAAGCAATATTTACCCAC 2508
 K  S  L  F  H  S  K  D  S  A  E  A  V  K  A  I  F  T  H
AATAAGTTTAAAGAACTACTTGAACATGCAAGAACAACCCAAACAATACGCAGGCGC 2565
 N  K  F  K  E  L  L  E  H  A  R  T  T  Q  T  I  R  R  R
TTTGCAAATGCTTTAGATCAACTAAAAGCGCTAATTACCTGTGGCAGCGGTGATCAT 2622
 F  A  N  A  L  D  Q  L  K  A  L  I  T  C  G  S  G  D  H
```

Fig.2C

```
    GCAACAAAACTACAAGCCTTTGGAAGTGCACTATGCACCAAAAAGAAGGAGTTGTGC  2679
 5   A  T  K  L  Q  A  F  G  S  A  L  C  T  K  K  K  E  L  C
    AGTAATTTTAGCTGTGCAAACTGCAGTAGTACAACAACTGCATAATTACGTAGCGCT  2736
     S  N  F  S  C  A  N  C  S  S  T  T  T  A  *
    AGGTGGGGGTAATTTACCCCCACCTAGCTAGAATCACACGGGGAACTTTCTCTCTAT  2793
10      Transcription termination
    TACTAGGGTCTTAGGATTTACAAACAAATTACTATGACAGCCA                2836
```

Fig.3A

```
ATTGGATCTAAATAATATACACTGGAGGTTCGTATTTTCTATTATGAAAGGGATAGA  57
            -35                    -10       +1
ATGTTAAATTTTATGATTTTTTATAATAAAAATAGATATAAAATTTAGTAATTTTAT 114

AAATTTTTTATAACAAAGGACTACCCTCCCTACATAAAATTTCTAAGACGAAAAATC 171
                                                    RBS
CCTATGTCAAATGAAACACTTCTGAGCGTACTTTCTGATGAAACGCACTTTGCTAAT 228
  M  S  N  E  T  L  L  S  V  L  S  D  E  T  H  F  A  N

CTAGTTGATGAACTTCTTCTCAGCTTGGTTAAAGACAGTATTTTCACTCAAGTAATA 285
  L  V  D  E  L  L  L  S  L  V  K  D  S  I  F  T  Q  V  I

AAAGGCGAGGGAAAGACAGAATTAAAAGACATTCTTACAGATAGCACTGGCAAGTTT 342
  K  G  E  G  K  T  E  L  K  D  I  L  T  D  S  T  G  K  F

AAAGAGCTGATAGGAAGTAGCGGTAAGGATATACTAAAAAGCATACACACAGATGGC 399
  K  E  L  I  G  S  S  G  K  D  I  L  K  S  I  H  T  D  G

TCAGGCAACTTTAAAGGCCTTATACAAAGCACAGGTAAGGCAGAAGTAAAAGAGGTA 456
  S  G  N  F  K  G  L  I  Q  S  T  G  K  A  E  V  K  E  V

CTCACTAATGAAAAATTCAAAGAGCTTTTTGGAAGCGAAGGTAAAGACATACTAAAA 513
  L  T  N  E  K  F  K  E  L  F  G  S  E  G  K  D  I  L  K

GAGATACTTACAGACAATACCGGCAATTTTAAAGGGCTTATAGAAGGCAAAGGTAAG 570
  E  I  L  T  D  N  T  G  N  F  K  G  L  I  E  G  K  G  K

GATGAAGCAAAGGGAGTACTTACTGACGAGAAATTTAAAGGCTTGTTTGATGACAAA 627
  D  E  A  K  G  V  L  T  D  E  K  F  K  G  L  F  D  D  K

ACAATAGCTGGCTATGTAAAAGAAATACTCACCAGCGAGAGTTTAAAAAACTGTTTG 684
  T  I  A  G  Y  V  K  E  I  L  T  S  E  S  L  K  N  C  L

AAAGGTGCAGGTAAGACTAAAGTAAAAGAACTCCTCATTGATGAGAAGTTTCAAAAA 741
  K  G  A  G  K  T  K  V  K  E  L  L  I  D  E  K  F  Q  K

TTATTTGAGGATGACACGAAAGCCAGTCATGTAAAAGAAATACTTACAGACAGTAAC 798
  L  F  E  D  D  T  K  A  S  H  V  K  E  I  L  T  D  S  N

GCTAAGGAAATACTCACAAATGAAGTAGCAAAAGAGGTACTAAAATCCGATAAATTT 855
  A  K  E  I  L  T  N  E  V  A  K  E  V  L  K  S  D  K  F

AAAGATGCAATAACTGGTGCTGGTAAGGACGCACTAAAAGAGATACTTACTTGCGAT 912
  K  D  A  I  T  G  A  G  K  D  A  L  K  E  I  L  T  C  D

AAATTTAAAGATGCAGTAACAGGTAATGGTAAGGACGCACTAAAAGAAATACTTACT 969
  K  F  K  D  A  V  T  G  N  G  K  D  A  L  K  E  I  L  T

TGCGATAAATTTAAAGATGCAGTAACAGGCAATGGTAAAGACAAGCTAAAAGAGATT 1026
  C  D  K  F  K  D  A  V  T  G  N  G  K  D  K  L  K  E  I

CTTACTCACGAGAAGTTTAAAGCACTCATAGAGAGTGAAGGCAAAGACATACTGAAA 1083
  L  T  H  E  K  F  K  A  L  I  E  S  E  G  K  D  I  L  K

GAAATTCTTACAGATAGTACCGGTAAATTTAAAGAGCTAATAGAAAGCACTGGTAAA 1140
  E  I  L  T  D  S  T  G  K  F  K  E  L  I  E  S  T  G  K

GACAAGCTAAAAGAGATTTTCACAGATAACACCGGTAACTTTAAAGGGCTTGTAGAA 1197
  D  K  L  K  E  I  F  T  D  N  T  G  N  F  K  G  L  V  E

GGCGCCGGTAAGGATGAAGCAAAAGCAGTACTTACTCACGAGAAATTTAAAGACTTG 1254
  G  A  G  K  D  E  A  K  A  V  L  T  H  E  K  F  K  D  L

TTTAATGACAAAACAACAGCTGGCTACGTGAAAGAAATACTCACCAGTGATAAGTTT 1311
  F  N  D  K  T  T  A  G  Y  V  K  E  I  L  T  S  D  K  F

AAAAAATTATTTGAGGACAATACCAAAGCTGGCTACGTGAAAGAAATACTCACGAAC 1368
  K  K  L  F  E  D  N  T  K  A  G  Y  V  K  E  I  L  T  N
```

Fig.3B

```
GATACAGCTAAGGAAATACTCACAAATCAAACAGCTAAAGAAGTCCTAAAAGACAGC  1425
 D  T  A  K  E  I  L  T  N  Q  T  A  K  E  V  L  K  D  S
ACAGCCAAAGAAATACTAAAATGCGATAAATTTAAGGACGCAATAACAGGCGCTGGT  1482
 T  A  K  E  I  L  K  C  D  K  F  K  D  A  I  T  G  A  G
AAAGATGAGCTAAAATACATACTCACTAATAACGAGTTTAAAAGCTTATTTGATAGC  1539
 K  D  E  L  K  Y  I  L  T  N  N  E  F  K  S  L  F  D  S
AAAGATAGCGCTGAAGCTGTTAAAGCAATATTTACCCACAATAAGTTTAAAGAACTA  1596
 K  D  S  A  E  A  V  K  A  I  F  T  H  N  K  F  K  E  L
CTTAAAACGTGCAAGGACAACCCAAAAAATACGGCGGCGCTTGCAGCTGCTTTAGAT  1653
 L  K  T  C  K  D  N  P  K  N  T  A  A  L  A  A  A  L  D
GAACTAAAAGATCTAATTACGTGTGACCGCAATAATCATGCAACAAAACTACAAGCC  1710
 E  L  K  D  L  I  T  C  D  R  N  N  H  A  T  K  L  Q  A
TTTGGAAGTGCACTATGCACCAGAAAAAAAGAGTCGTGCGATAATTTTAGCCCTGCA  1767
 F  G  S  A  L  C  T  R  K  K  E  S  C  D  N  F  S  P  A
AGCTGCAGTAGTACAGCAGCTACATAATTACGTAGCGCTAGGTGGGGGTAAATTACC  1824
 S  C  S  S  T  A  A  T              Transcription termination
CCCACCTACGTAGAATCACACGGGGAACTTTCTCTCTATTACTGAGGTCTTAGGATT  1881
TACTTTCAAATTACTATGACAGCCGATTAAATTATTATGACAGACGATACACTTTT  1937
```

Fig.3C

```
     GATACAGCTAAGGAAATACTCACAAATCAAACAGCTAAAGAAGTCCTAAAAGACAGC 1425
      D  T  A  K  E  I  L  T  N  Q  T  A  K  E  V  L  K  D  S
 5   ACAGCCAAAGAAATACTAAAATGCGATAAATTTAAGGACGCAATAACAGGCGCTGGT 1482
      T  A  K  E  I  L  K  C  D  K  F  K  D  A  I  T  G  A  G
     AAAGATGAGCTAAAATACATACTCACTAATAACGAGTTTAAAAGCTTATTTGATAGC 1539
      K  D  E  L  K  Y  I  L  T  N  N  E  F  K  S  L  F  D  S
     AAAGATAGCGCTGAAGCTGTTAAAGCAATATTTACCCACAATAAGTTTAAAGAACTA 1596
10    K  D  S  A  E  A  V  K  A  I  F  T  H  N  K  F  K  E  L
     CTTAAAACGTGCAAGGACAACCCAAAAAATACGGCGGCGCTTGCAGCTGCTTTAGAT 1653
      L  K  T  C  K  D  N  P  K  N  T  A  A  L  A  A  A  L  D
     GAACTAAAAGATCTAATTACGTGTGACCGCAATAATCATGCAACAAAACTACAAGCC 1710
      E  L  K  D  L  I  T  C  D  R  N  N  H  A  T  K  L  Q  A
     TTTGGAAGTGCACTATGCACCAGAAAAAAAGAGTCGTGCGATAATTTTAGCCCTGCA 1767
15    F  G  S  A  L  C  T  R  K  K  E  S  C  D  N  F  S  P  A
     AGCTGCAGTAGTACAGCAGCTACATAATTACGTAGCGCTAGGTGGGGGTAAATTACC 1824
      S  C  S  S  T  A  A  T              Transcription termination
     CCCACCTACGTAGAATCACACGGGGAACTTTCTCTCTATTACTGAGGTCTTAGGATT 1881
20
     TACTTTCAAATTACTATGACAGCCGATTAAATTATTATGACAGACGATACACTTTT 1937
```

Fig.4A

```
ATTGGATCTAAATAATGTACACTGGAGGTTCGTATTTTCTATTATGAAAGGGATAGA  57
         -35                              -10       +1
ATGTTAAATTTTATGATTTTTTATAATAAAAATAGATATAAAATTTAGTAGTTTTAT  114

AAATTTTTCATAACAAGGACTATCCTCCTTGCATAAAATTTCTAAGACGAAAAATC   171
                                                  RBS
CTTATGTCAAATGAAACACTTCTGAGCGTACTTTCTGATGAAACGCACTTTGCTAAT  225
     M  S  N  E  T  L  L  S  V  L  S  D  E  T  H  F  A  N
CTAGTTGATGAACTTCTTCTCAGCTTGGTTAAAGACAGTATTTTCACTCAAGTAATA  285
  L  V  D  E  L  L  L  S  L  V  K  D  S  I  F  T  Q  V  I
AAAGGCGAGGGAAAGACAGAATTAAAAGACATTCTTACAGATAGCACTGGCAAGTTT  342
  K  G  E  G  K  T  E  L  K  D  I  L  T  D  S  T  G  K  F
AAAGAGCTGATAGGAAGTAGCGGTAAGGATATACTAAAAAGCATACTCACAGATGGC  399
  K  E  L  I  G  S  S  G  K  D  I  L  K  S  I  L  T  D  G
TCAGGCAACTTTAAAGGCCTTATACAAAGCACAGGTAAGGCAGAAGTAAAAGAGGTA  456
  S  G  N  F  K  G  L  I  Q  S  T  G  K  A  E  V  K  E  V
CTCACTAATGAAAAATTCAAAGAGCTTTTTGGAAGCGATGGTAAGGATATATTAAAA  513
  L  T  N  E  K  F  K  E  L  F  G  S  D  G  K  D  I  L  K
GACATACTCACAGATAGCACTGGTAAGTTTAAAGAGCTGATAGGAAGTAGCGGTAAG  570
  D  I  L  T  D  S  T  G  K  F  K  E  L  I  G  S  S  G  K
GACATACTAAAAAACATTCTTACAGATAGCACCGGTAAGTTTAAAGAACTTATAGAA  627
  D  I  L  K  N  I  L  T  D  S  T  G  K  F  K  E  L  I  E
AGTGCAGGTAAGGGTAAGCTGAAAGACCTTCTTATTGATGGAAACTTTAAAAAATTA  684
  S  A  G  K  G  K  L  K  D  L  L  I  D  G  N  F  K  K  L
TTTGAGGATGACACGAAAGCTGCTCATGTAAAAGAAATACTTACAGACAGCAACGCT  741
  F  E  D  D  T  K  A  A  K  V  K  E  I  L  T  D  S  N  A
AAGGAAATACTCACAAATGAAGTAGCAAAAGAGGTACTAAAATCCGATAAATTTAAA  798
  K  E  I  L  T  N  E  V  A  K  E  V  L  K  S  D  K  F  K
GATGCAATAACTGGTGCTGGTAAGGACGCACTAAAAGAGATACTTACTTGCGATAAA  855
  D  A  I  T  G  A  G  K  D  A  L  K  E  I  L  T  C  D  K
TTTAAAGATGCAGTAACAGGCAATGGTAAGGACGCACTAAAAGAAATACTTACTTGC  912
  F  K  D  A  V  T  G  N  G  K  D  A  L  K  E  I  L  T  C
GATAAATTTAAAGATGCAGTAACAGGCAATGGTAAAGACAAGCTAAAAGAGATTCTT  969
  D  K  F  K  D  A  V  T  G  N  G  K  D  K  L  K  E  I  L
```

Fig.4B

```
ACTCACGAGAAGTTTAAAGCACTCATAGAGAGTGAAGGCAAAGACATACTGAAAGAC 1026
 T  H  E  K  F  K  A  L  I  E  S  E  G  K  D  I  L  K  D
ATTCTTACAGATAGTACCGGTAAATTTAAAGAGCTAATAGAAAGCACGGGTAAGGAT 1083
 I  L  T  D  S  T  G  K  F  K  E  L  I  E  S  T  G  K  D
GAAGCAAAAGCAGTACTTACTGACGAGAAATTTAAAGACTTGTTTAATGACAAAACA 1140
 E  A  K  A  V  L  T  D  E  K  F  K  D  L  F  N  D  K  T
ACAGCTGGCTACGTGAAAGAAATACTCACCAGTGATAAGTTTAAAAAATTATTTGAG 1197
 T  A  G  Y  V  K  E  I  L  T  S  D  K  F  K  K  L  F  E
GACAATACCAAAGCTGGCTACGTGAAAGAAATACTCACGAACGATACAGCTAAGGAA 1254
 D  N  T  K  A  G  Y  V  K  E  I  L  T  N  D  T  A  K  E
ATACTTACCAATCATAAATTTAAGGAAGCAATAACTGGCGATGGTAAAGACATACTG 1311
 I  L  T  N  H  K  F  K  E  A  I  T  G  D  G  K  D  I  L
AAAGAAATTCTTACAGATAGCACTGGTAACTTTAAAGGCGCAATAACAGGTGCCGGT 1368
 K  E  I  L  T  D  S  T  G  N  F  K  G  A  I  T  G  A  G
AAAGATCAGCTAAAATACATACTCACTAATAGCGAGTTTAAAAGCTTATTTGATAGC 1425
 K  D  Q  L  K  Y  I  L  T  N  S  E  F  K  S  L  F  D  S
AAAGATAGCGCTGAAGCTGTTAAAGAAATATTTACCCACAGTAAGTTTAAAGAACTA 1482
 K  D  S  A  E  A  V  K  E  I  F  T  H  S  K  F  K  E  L
CTTAAAACGTGCAAGGACAACCCAAAAAATACGGCGGCGCTTGCAGCTGCTTTAGAT 1539
 L  K  T  C  K  D  N  P  K  N  T  A  A  L  A  A  A  L  D
GAACTAAAAGATCTAATTACCTGTGGCAGCGGTGATCATGCAACAAAACTACAAGCC 1596
 E  L  K  D  L  I  T  C  G  S  G  D  H  A  T  K  L  Q  A
TTTGGAAGTGCACTATGCACCAGAAAAAAAGAGTCGTGCGATAATTTTAGCTCTGCA 1653
 F  G  S  A  L  C  T  R  K  K  E  S  C  D  N  F  S  S  A
AACTGCAGTAGTACAACAACTGCATAATTACGTAGCGCTAGGTGGGGGTAATTTACC 1710
 N  C  S  S  T  T  T  A  *            Transcription termination
CCCACCTAGCTAGAATCACACGGGGAACTTTCTCTCTATTACTAGGGTCTTAGGATT 1767
ACAAACAAATTACTATGACAGCCA                                    1791
```

Fig.5

50kD antigen

MSNETLLSVLSDETHFANLVDELLLSLVKDSIFTQVIKGEGKTELKDILTDSTGKFKELIGSSGKDILKSIHTDGSGNFKGLIQSTGKAEVKEVLTNEKF
      |DI                                                                                                              |DII

KELFGSEGKDILKEILTDNTGNFKKGLIEGKGKDEAKGVLTDEKFKGLFDDKTIAGYVKEILTDEKFQKLFEDTKASHV
          |DIII

KELTDSNAKEILTNEVAKEVLKSDKFKDAITGNGKDAALKEILTCDKFKDAVTGNGKDKLKEILTHEKFKALIESEG
          |DIV

KDILKEILTDSTGKFKELIESTGKDKLKEIFTDNTGNFKGLVEGAGKDEAKAVLTHEKFKDLFNDKTTAGYVKEILTSDKFKLFEDNTKAGYVKEILT
       |DVI                                            |DVIII

NDTAKEILTNQTAKEVLKDSTAKEILKCDKFKDAITGAGKDELKYILTNNEFKSLFDSKDSAEAVKAIFTHNKFKELLKTCKDNPKNTAALAAALDE

LKDLITCDRNNHATKLQAFGSALCTRKKESCDNFSPASCSSTAAT

85kD antigen

MSNETLLSVLSDETHFANLVDELLLILVKDSIFTQVIKGEGKTELKDILTDNTGKFKELIESAGKDILKEILTDNTGNFKGLIEGNGKTEAKEVRTNEKF
      |DI

KELFGSNGKDILKDILTDNTGNFKKGLIESAAKGKLKDLLIDEKFQKLFEDETKAGRVKEILTDSNAKEILTNEVAKEVLKSDKFKEAITGDGKDALKE
           |DIV                                                                                        |DVII

ILTCDKFKEAVTGNGKDILKGILTDSTGKFKELIESTSKDILKEILTNQTAKEVLKEILTCDKFKEAVTGDGKDILKGILTDSTGKFKELIESTGKDILK
                                           |DV                                                                                  |DVI

TDQTAKEVLKDSTAKDILKDTNAAAVLKNSTAKEILTNQTAKEVLTDGTSKEVLKEILTCDKFKEAVTGDGKDILKGILTDSTGKFKELIESTGKDILK

DILTDSTGKFKELIEVLVKNKLKEILTDNTGNFKGLVEGAGKDEAKAVLTDEKFKGLFDDKTIAGYVKEILTSEKFKKLFESAGKTKVKELLIDEKFQKL
  |DII                                                                                                                   |DIII

FEDDTKASHVKEILTDQTAKEILTNDTAKEVLKDSTAKEILKDTNAAALLKDSTAKEVLKDKFKDAITGAGKDAALKEILTCDKFKEAVTGNGKDIL

KGILTDSTGKFKELIESTGKDKLKEILTDNTGNFKFLVEGAGKDEAKAVLTHEKFKDLFNVKTTAGYVKEILTSDKFKELFTDATKAYVKEILTNDTAK
                                                                                                  |DVIII

ILTDQTAKEVLKDGTAKDILKDTNARALLKDTAKEVLKCDKFKEAITGAGKDELKYILTNSEFKSLFHSKDSAEAVKAIFTHNKFKELLEHARTTQTIR

RRFANALDQLKALITCGSGDHATKLQAFGSALCTKKKELCSNFSCANCSSTTTA

SEQUENCE LISTING

<160> NUMBER OF SEQ ID NOS: 48

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: synthetic primer

<400> SEQUENCE: 1
cataaaattt ctaagacgaa ggatccctat gtc                                33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: synthetic primer

<400> SEQUENCE: 2
gagagaaagt tccccgtgtg aattctagct agg                                33

<210> SEQ ID NO 3
<211> LENGTH: 2836
<212> TYPE: DNA
<213> ORGANISM: Ehrlichia risticii
<220> FEATURE:
<221> NAME/KEY: CDS
<222> LOCATION: (175)..(2721)

<400> SEQUENCE: 3
attggatcta aataatgtac actggaggtt cgtattttct attatgaaag ggatagaatg      60
ttaaatttta tgattttta taataaaaat agatataaaa tttagtagtt ttataaattt      120
ttcataacaa aggactatcc tccttgcata aaatttctaa gacgaaaaat ccct atg      177
                                                              Met
                                                               1 tca aat gaa aca ctt ttg agc gta ctt tct gat gaa acg cac ttt gct      225
Ser Asn Glu Thr Leu Leu Ser Val Leu Ser Asp Glu Thr His Phe Ala
              5                   10                  15 aat cta gtt gat gaa ctt ctt ctc atc ttg gtt aaa gac agt att ttc      273
Asn Leu Val Asp Glu Leu Leu Leu Ile Leu Val Lys Asp Ser Ile Phe
         20                  25                  30 act caa gta ata aaa ggc gag gga aag aca gaa tta aaa gac ata ctt      321
Thr Gln Val Ile Lys Gly Glu Gly Lys Thr Glu Leu Lys Asp Ile Leu
     35                  40                  45 aca gac aac act ggt aag ttt aaa gaa ctt ata gaa agt gca ggt aaa      369
Thr Asp Asn Thr Gly Lys Phe Lys Glu Leu Ile Glu Ser Ala Gly Lys
 50                  55                  60                  65 gac ata cta aaa gag ata ctt aca gac aat acc ggc aat ttt aaa gga      417
Asp Ile Leu Lys Glu Ile Leu Thr Asp Asn Thr Gly Asn Phe Lys Gly
                 70                  75                  80 ctt ata gaa ggt aat ggt aag acg gag gca aaa gag gta cgc act aat      465

```
                    -continued

Leu Ile Glu Gly Asn Gly Lys Thr Glu Ala Lys Glu Val Arg Thr Asn
                85                  90                  95 gaa aaa ttc aag gag ctt ttt gga agc aat ggt aag gac ata ctg aaa      513
Glu Lys Phe Lys Glu Leu Phe Gly Ser Asn Gly Lys Asp Ile Leu Lys
            100                 105                 110 gac att ctt act gat aac acc ggt aac ttt aaa ggc tta ata gaa agt      561
Asp Ile Leu Thr Asp Asn Thr Gly Asn Phe Lys Gly Leu Ile Glu Ser
        115                 120                 125 gca gct aag ggt aag ctg aaa gat ctt ctt att gat gaa aaa ttt caa      609
Ala Ala Lys Gly Lys Leu Lys Asp Leu Leu Ile Asp Glu Lys Phe Gln
130                 135                 140                 145 aaa tta ttc gag gat gaa acg aaa gct ggt cgt gta aaa gaa ata ctt      657
Lys Leu Phe Glu Asp Glu Thr Lys Ala Gly Arg Val Lys Glu Ile Leu
                150                 155                 160 aca gac agc aac gct aag gaa ata ctc aca aat gaa gta gca aaa gag      705
Thr Asp Ser Asn Ala Lys Glu Ile Leu Thr Asn Glu Val Ala Lys Glu
            165                 170                 175 gta cta aaa tcc gat aaa ttc aag gag gca ata act ggc gat ggt aag      753
Val Leu Lys Ser Asp Lys Phe Lys Glu Ala Ile Thr Gly Asp Gly Lys
        180                 185                 190 gac gca cta aaa gag ata ctt act tgt gat aaa ttt aaa gag gct gta      801
Asp Ala Leu Lys Glu Ile Leu Thr Cys Asp Lys Phe Lys Glu Ala Val
195                 200                 205 aca ggc aat ggt aaa gac ata cta aaa ggt ata ctt aca gat agc act      849
Thr Gly Asn Gly Lys Asp Ile Leu Lys Gly Ile Leu Thr Asp Ser Thr
210                 215                 220                 225 ggt aaa ttt aaa gaa ctt ata gaa agt act agt aaa gac ata cta aaa      897
Gly Lys Phe Lys Glu Leu Ile Glu Ser Thr Ser Lys Asp Ile Leu Lys
                230                 235                 240 gag ata ctt aca gat aat acc ggt aac ttt aaa ggc ctt ata gaa agc      945
Glu Ile Leu Thr Asp Asn Thr Gly Asn Phe Lys Gly Leu Ile Glu Ser
            245                 250                 255 act ggc aag gag aaa gta aaa gaa ctt ctt atc gat ggg aag ttt aag      993
Thr Gly Lys Glu Lys Val Lys Glu Leu Leu Ile Asp Gly Lys Phe Lys
        260                 265                 270 gac ctg ttt act gat gca aca aaa gcc ggt tat gta aaa gaa ata ctc     1041
Asp Leu Phe Thr Asp Ala Thr Lys Ala Gly Tyr Val Lys Glu Ile Leu
275                 280                 285 acg aac gat aca gct aag gaa gta ctt aca gat caa aca gca aag gag     1089
Thr Asn Asp Thr Ala Lys Glu Val Leu Thr Asp Gln Thr Ala Lys Glu
290                 295                 300                 305 gtc cta aaa gat agt aca gct aaa gac ata tta aag gac aca aac gca     1137
Val Leu Lys Asp Ser Thr Ala Lys Asp Ile Leu Lys Asp Thr Asn Ala
                310                 315                 320 gct gcg gta cta aaa aac agc aca gct aaa gaa ata ctt aca aac caa     1185
Ala Ala Val Leu Lys Asn Ser Thr Ala Lys Glu Ile Leu Thr Asn Gln
            325                 330                 335 acc gct aaa gaa gtg ctt aca gat ggt aca tcc aaa gaa gta cta aaa     1233
Thr Ala Lys Glu Val Leu Thr Asp Gly Thr Ser Lys Glu Val Leu Lys
        340                 345                 350 gag ata ctt act tgt gat aaa ttt aaa gag gca gta aca gga gat ggt     1281
Glu Ile Leu Thr Cys Asp Lys Phe Lys Glu Ala Val Thr Gly Asp Gly
355                 360                 365 aaa gac ata cta aaa ggt ata ctt aca gat agc act ggt aag ttt aaa     1329
Lys Asp Ile Leu Lys Gly Ile Leu Thr Asp Ser Thr Gly Lys Phe Lys
370                 375                 380                 385 gaa ctt ata gaa agt act ggt aaa gac ata ctg aaa gac att ctt aca     1377
Glu Leu Ile Glu Ser Thr Gly Lys Asp Ile Leu Lys Asp Ile Leu Thr
                390                 395                 400
```

-continued

| | |
|---|---|
| gat agc act ggt aaa ttt aaa gaa ctt ata gaa gta ctg gta aag aac<br>Asp Ser Thr Gly Lys Phe Lys Glu Leu Ile Glu Val Leu Val Lys Asn<br>     405                    410                    415 | 1425 |
| aag cta aaa gag att ctt aca gat aac acc ggt aac ttc aaa ggg ctt<br>Lys Leu Lys Glu Ile Leu Thr Asp Asn Thr Gly Asn Phe Lys Gly Leu<br>         420                    425                   430 | 1473 |
| gta gaa ggc gcc ggg aag gat gaa gca aaa gca gta ctt act gac gag<br>Val Glu Gly Ala Gly Lys Asp Glu Ala Lys Ala Val Leu Thr Asp Glu<br>435                   440                    445 | 1521 |
| aaa ttt aaa ggc ttg ttt gat gac aaa aca ata gct ggc tat gta aaa<br>Lys Phe Lys Gly Leu Phe Asp Asp Lys Thr Ile Ala Gly Tyr Val Lys<br>450                   455                   460                   465 | 1569 |
| gaa ata ctc acc agc gag aag ttt aaa aaa ctg ttt gaa agt gca ggt<br>Glu Ile Leu Thr Ser Glu Lys Phe Lys Lys Leu Phe Glu Ser Ala Gly<br>                 470                   475                   480 | 1617 |
| aag act aaa gta aaa gaa ctc ctc att gat gag aag ttt caa aaa tta<br>Lys Thr Lys Val Lys Glu Leu Leu Ile Asp Glu Lys Phe Gln Lys Leu<br>               485                   490                   495 | 1665 |
| ttt gag gat gac acg aaa gcc agt cat gta aaa gaa ata ctc acg aac<br>Phe Glu Asp Asp Thr Lys Ala Ser His Val Lys Glu Ile Leu Thr Asn<br>     500                    505                    510 | 1713 |
| gat aca gct aag gaa ata ctt aca gat caa aca gct aaa gaa gtc cta<br>Asp Thr Ala Lys Glu Ile Leu Thr Asp Gln Thr Ala Lys Glu Val Leu<br>515                   520                    525 | 1761 |
| aag gat agt aca gct aaa gag ata tta aag gac aca aac gca gct gcg<br>Lys Asp Ser Thr Ala Lys Glu Ile Leu Lys Asp Thr Asn Ala Ala Ala<br>530                   535                   540                 545 | 1809 |
| cta cta aaa gac agc aca gca aaa gag gta cta aaa tcc gat aaa ttt<br>Leu Leu Lys Asp Ser Thr Ala Lys Glu Val Leu Lys Ser Asp Lys Phe<br>               550                   555                   560 | 1857 |
| aaa gat gca ata act ggt gct ggt aag gac gca cta aaa gag ata ctt<br>Lys Asp Ala Ile Thr Gly Ala Gly Lys Asp Ala Leu Lys Glu Ile Leu<br>               565                   570                   575 | 1905 |
| act tgt gat aaa ttt aaa gag gca gta aca ggc aat ggt aaa gac ata<br>Thr Cys Asp Lys Phe Lys Glu Ala Val Thr Gly Asn Gly Lys Asp Ile<br>               580                   585                   590 | 1953 |
| cta aaa ggt ata ctt aca gat agc act ggt aaa ttt aaa gag cta ata<br>Leu Lys Gly Ile Leu Thr Asp Ser Thr Gly Lys Phe Lys Glu Leu Ile<br>595                   600                    605 | 2001 |
| gaa agc act ggt aag gat aag cta aaa gag att ctt aca gat aac acc<br>Glu Ser Thr Gly Lys Asp Lys Leu Lys Glu Ile Leu Thr Asp Asn Thr<br>610                   615                   620                 625 | 2049 |
| ggt aac ttt aaa ttt ctt gta gaa ggc gcc ggt aag gat gaa gca aaa<br>Gly Asn Phe Lys Phe Leu Val Glu Gly Ala Gly Lys Asp Glu Ala Lys<br>                 630                   635                   640 | 2097 |
| gca gta ctt act cac gag aaa ttt aaa gac ttg ttt aat gtc aaa aca<br>Ala Val Leu Thr His Glu Lys Phe Lys Asp Leu Phe Asn Val Lys Thr<br>               645                   650                   655 | 2145 |
| aca gct ggc tac gtg aaa gaa ata ctt acc agc gac aag ttt aaa gaa<br>Thr Ala Gly Tyr Val Lys Glu Ile Leu Thr Ser Asp Lys Phe Lys Glu<br>             660                    665                   670 | 2193 |
| ctg ttt act gat gca aca aaa gct ggc tac gtg aaa gaa ata ctc acg<br>Leu Phe Thr Asp Ala Thr Lys Ala Gly Tyr Val Lys Glu Ile Leu Thr<br>675                   680                    685 | 2241 |
| aac gat aca gct aag gaa ata ctt aca gat caa aca gct aaa gaa gtc<br>Asn Asp Thr Ala Lys Glu Ile Leu Thr Asp Gln Thr Ala Lys Glu Val<br>690                   695                   700                 705 | 2289 |
| cta aag gat ggt aca gct aaa gac ata tta aag gac aca aac gca cgt<br>Leu Lys Asp Gly Thr Ala Lys Asp Ile Leu Lys Asp Thr Asn Ala Arg<br>               710                   715                   720 | 2337 |

-continued

```
gcg cta cta aaa gac agc aca gcc aaa gaa gta cta aaa tgc gat aaa    2385
Ala Leu Leu Lys Asp Ser Thr Ala Lys Glu Val Leu Lys Cys Asp Lys
            725                 730                 735 ttt aag gaa gca ata aca ggt gcc ggt aaa gat gag cta aaa tac ata    2433
Phe Lys Glu Ala Ile Thr Gly Ala Gly Lys Asp Glu Leu Lys Tyr Ile
            740                 745                 750 ctc act aat agc gag ttt aaa agc tta ttt cat agc aaa gat agc gct    2481
Leu Thr Asn Ser Glu Phe Lys Ser Leu Phe His Ser Lys Asp Ser Ala
        755                 760                 765 gaa gct gtt aaa gca ata ttt acc cac aat aag ttt aaa gaa cta ctt    2529
Glu Ala Val Lys Ala Ile Phe Thr His Asn Lys Phe Lys Glu Leu Leu
770                 775                 780                 785 gaa cat gca aga aca acc caa aca ata cgc agg cgc ttt gca aat gct    2577
Glu His Ala Arg Thr Thr Gln Thr Ile Arg Arg Arg Phe Ala Asn Ala
                790                 795                 800 tta gat caa cta aaa gcg cta att acc tgt ggc agc ggt gat cat gca    2625
Leu Asp Gln Leu Lys Ala Leu Ile Thr Cys Gly Ser Gly Asp His Ala
            805                 810                 815 aca aaa cta caa gcc ttt gga agt gca cta tgc acc aaa aag aag gag    2673
Thr Lys Leu Gln Ala Phe Gly Ser Ala Leu Cys Thr Lys Lys Lys Glu
            820                 825                 830 ttg tgc agt aat ttt agc tgt gca aac tgc agt agt aca aca act gca    2721
Leu Cys Ser Asn Phe Ser Cys Ala Asn Cys Ser Ser Thr Thr Thr Ala
        835                 840                 845 taattacgta gcgctaggtg gggtaattt accccccacct agctagaatc acacggggaa    2781
ctttctctct attactaggg tcttaggatt tacaaacaaa ttactatgac agcca          2836
```

<210> SEQ ID NO 4
<211> LENGTH: 849
<212> TYPE: PRT
<213> ORGANISM: Ehrlichia risticii

<400> SEQUENCE: 4

```
Met Ser Asn Glu Thr Leu Leu Ser Val Leu Ser Asp Glu Thr His Phe
  1               5                  10                  15

Ala Asn Leu Val Asp Glu Leu Leu Ile Leu Val Lys Asp Ser Ile
             20                  25                  30

Phe Thr Gln Val Ile Lys Gly Glu Gly Lys Thr Glu Leu Lys Asp Ile
         35                  40                  45

Leu Thr Asp Asn Thr Gly Lys Phe Lys Glu Leu Ile Glu Ser Ala Gly
     50                  55                  60

Lys Asp Ile Leu Lys Glu Ile Leu Thr Asp Asn Thr Gly Asn Phe Lys
 65                  70                  75                  80

Gly Leu Ile Glu Gly Asn Gly Lys Thr Glu Ala Lys Glu Val Arg Thr
                 85                  90                  95

Asn Glu Lys Phe Lys Glu Leu Phe Gly Ser Asn Gly Lys Asp Ile Leu
            100                 105                 110

Lys Asp Ile Leu Thr Asp Asn Thr Gly Asn Phe Lys Gly Leu Ile Glu
        115                 120                 125

Ser Ala Ala Lys Gly Lys Leu Lys Asp Leu Leu Ile Asp Glu Lys Phe
    130                 135                 140

Gln Lys Leu Phe Glu Asp Glu Thr Lys Ala Gly Arg Val Lys Glu Ile
145                 150                 155                 160

Leu Thr Asp Ser Asn Ala Lys Glu Ile Leu Thr Asn Glu Val Ala Lys
                165                 170                 175
```

```
Glu Val Leu Lys Ser Asp Lys Phe Lys Glu Ala Ile Thr Gly Asp Gly
            180                 185                 190

Lys Asp Ala Leu Lys Glu Ile Leu Thr Cys Asp Lys Phe Lys Glu Ala
            195                 200                 205

Val Thr Gly Asn Gly Lys Asp Ile Leu Lys Gly Ile Leu Thr Asp Ser
            210                 215                 220

Thr Gly Lys Phe Lys Glu Leu Ile Glu Ser Thr Ser Lys Asp Ile Leu
225                 230                 235                 240

Lys Glu Ile Leu Thr Asp Asn Thr Gly Asn Phe Lys Gly Leu Ile Glu
                245                 250                 255

Ser Thr Gly Lys Glu Lys Val Lys Glu Leu Leu Ile Asp Gly Lys Phe
            260                 265                 270

Lys Asp Leu Phe Thr Asp Ala Thr Lys Ala Gly Tyr Val Lys Glu Ile
            275                 280                 285

Leu Thr Asn Asp Thr Ala Lys Glu Val Leu Thr Asp Gln Thr Ala Lys
            290                 295                 300

Glu Val Leu Lys Asp Ser Thr Ala Lys Asp Ile Leu Lys Asp Thr Asn
305                 310                 315                 320

Ala Ala Ala Val Leu Lys Asn Ser Thr Ala Lys Glu Ile Leu Thr Asn
                325                 330                 335

Gln Thr Ala Lys Glu Val Leu Thr Asp Gly Thr Ser Lys Glu Val Leu
            340                 345                 350

Lys Glu Ile Leu Thr Cys Asp Lys Phe Lys Glu Ala Val Thr Gly Asp
            355                 360                 365

Gly Lys Asp Ile Leu Lys Gly Ile Leu Thr Asp Ser Thr Gly Lys Phe
            370                 375                 380

Lys Glu Leu Ile Glu Ser Thr Gly Lys Asp Ile Leu Lys Asp Ile Leu
385                 390                 395                 400

Thr Asp Ser Thr Gly Lys Phe Lys Glu Leu Ile Glu Val Leu Val Lys
                405                 410                 415

Asn Lys Leu Lys Glu Ile Leu Thr Asp Asn Thr Gly Asn Phe Lys Gly
            420                 425                 430

Leu Val Glu Gly Ala Gly Lys Asp Glu Ala Lys Ala Val Leu Thr Asp
            435                 440                 445

Glu Lys Phe Lys Gly Leu Phe Asp Asp Lys Thr Ile Ala Gly Tyr Val
            450                 455                 460

Lys Glu Ile Leu Thr Ser Glu Lys Phe Lys Lys Leu Phe Glu Ser Ala
465                 470                 475                 480

Gly Lys Thr Lys Val Lys Glu Leu Leu Ile Asp Glu Lys Phe Gln Lys
                485                 490                 495

Leu Phe Glu Asp Asp Thr Lys Ala Ser His Val Lys Glu Ile Leu Thr
            500                 505                 510

Asn Asp Thr Ala Lys Glu Ile Leu Thr Asp Gln Thr Ala Lys Glu Val
            515                 520                 525

Leu Lys Asp Ser Thr Ala Lys Glu Ile Leu Lys Asp Thr Asn Ala Ala
            530                 535                 540

Ala Leu Leu Lys Asp Ser Thr Ala Lys Glu Val Leu Lys Ser Asp Lys
545                 550                 555                 560

Phe Lys Asp Ala Ile Thr Gly Ala Gly Lys Asp Ala Leu Lys Glu Ile
                565                 570                 575

Leu Thr Cys Asp Lys Phe Lys Glu Ala Val Thr Gly Asn Gly Lys Asp
            580                 585                 590

Ile Leu Lys Gly Ile Leu Thr Asp Ser Thr Gly Lys Phe Lys Glu Leu
```

-continued

```
        595                 600                 605

Ile Glu Ser Thr Gly Lys Asp Lys Leu Lys Glu Ile Leu Thr Asp Asn
    610                 615                 620

Thr Gly Asn Phe Lys Phe Leu Val Glu Gly Ala Gly Lys Asp Glu Ala
625                 630                 635                 640

Lys Ala Val Leu Thr His Glu Lys Phe Lys Asp Leu Phe Asn Val Lys
                645                 650                 655

Thr Thr Ala Gly Tyr Val Lys Glu Ile Leu Thr Ser Asp Lys Phe Lys
            660                 665                 670

Glu Leu Phe Thr Asp Ala Thr Lys Ala Gly Tyr Val Lys Glu Ile Leu
        675                 680                 685

Thr Asn Asp Thr Ala Lys Glu Ile Leu Thr Asp Gln Thr Ala Lys Glu
    690                 695                 700

Val Leu Lys Asp Gly Thr Ala Lys Asp Ile Leu Lys Asp Thr Asn Ala
705                 710                 715                 720

Arg Ala Leu Leu Lys Asp Ser Thr Ala Lys Glu Val Leu Lys Cys Asp
                725                 730                 735

Lys Phe Lys Glu Ala Ile Thr Gly Ala Gly Lys Asp Glu Leu Lys Tyr
            740                 745                 750

Ile Leu Thr Asn Ser Glu Phe Lys Ser Leu Phe His Ser Lys Asp Ser
        755                 760                 765

Ala Glu Ala Val Lys Ala Ile Phe Thr His Asn Lys Phe Lys Glu Leu
    770                 775                 780

Leu Glu His Ala Arg Thr Thr Gln Thr Ile Arg Arg Arg Phe Ala Asn
785                 790                 795                 800

Ala Leu Asp Gln Leu Lys Ala Leu Ile Thr Cys Gly Ser Gly Asp His
                805                 810                 815

Ala Thr Lys Leu Gln Ala Phe Gly Ser Ala Leu Cys Thr Lys Lys Lys
            820                 825                 830

Glu Leu Cys Ser Asn Phe Ser Cys Ala Asn Cys Ser Ser Thr Thr Thr
        835                 840                 845

Ala

<210> SEQ ID NO 5
<211> LENGTH: 1937
<212> TYPE: DNA
<213> ORGANISM: Ehrlichia risticii
<220> FEATURE:
<221> NAME/KEY: CDS
<222> LOCATION: (175)..(1791)

<400> SEQUENCE: 5
attggatcta aataatatac actggaggtt cgtattttct attatgaaag ggatagaatg      60
ttaaatttta tgatttttta taataaaaat agatataaaa tttagtaatt ttataaattt     120
tttataacaa aggactaccc tccctacata aaatttctaa gacgaaaaat ccct atg       177
                                                            Met
                                                              1 tca aat gaa aca ctt ctg agc gta ctt tct gat gaa acg cac ttt gct       225
Ser Asn Glu Thr Leu Leu Ser Val Leu Ser Asp Glu Thr His Phe Ala
            5                  10                  15 aat cta gtt gat gaa ctt ctt ctc agc ttg gtt aaa gac agt att ttc       273
Asn Leu Val Asp Glu Leu Leu Leu Ser Leu Val Lys Asp Ser Ile Phe
        20                  25                  30 act caa gta ata aaa ggc gag gga aag aca gaa tta aaa gac att ctt       321
Thr Gln Val Ile Lys Gly Glu Gly Lys Thr Glu Leu Lys Asp Ile Leu
     35                  40                  45
```

```
aca gat agc act ggc aag ttt aaa gag ctg ata gga agt agc ggt aag      369
Thr Asp Ser Thr Gly Lys Phe Lys Glu Leu Ile Gly Ser Ser Gly Lys
 50              55                  60                  65 gat ata cta aaa agc ata cac aca gat ggc tca ggc aac ttt aaa ggc      417
Asp Ile Leu Lys Ser Ile His Thr Asp Gly Ser Gly Asn Phe Lys Gly
             70                  75                  80 ctt ata caa agc aca ggt aag gca gaa gta aaa gag gta ctc act aat      465
Leu Ile Gln Ser Thr Gly Lys Ala Glu Val Lys Glu Val Leu Thr Asn
             85                  90                  95 gaa aaa ttc aaa gag ctt ttt gga agc gaa ggt aaa gac ata cta aaa      513
Glu Lys Phe Lys Glu Leu Phe Gly Ser Glu Gly Lys Asp Ile Leu Lys
            100                 105                 110 gag ata ctt aca gac aat acc ggc aat ttt aaa ggg ctt ata gaa ggc      561
Glu Ile Leu Thr Asp Asn Thr Gly Asn Phe Lys Gly Leu Ile Glu Gly
    115                 120                 125 aaa ggt aag gat gaa gca aag gga gta ctt act gac gag aaa ttt aaa      609
Lys Gly Lys Asp Glu Ala Lys Gly Val Leu Thr Asp Glu Lys Phe Lys
130                 135                 140                 145 ggc ttg ttt gat gac aaa aca ata gct ggc tat gta aaa gaa ata ctc      657
Gly Leu Phe Asp Asp Lys Thr Ile Ala Gly Tyr Val Lys Glu Ile Leu
                150                 155                 160 acc agc gag agt tta aaa aac tgt ttg aaa ggt gca ggt aag act aaa      705
Thr Ser Glu Ser Leu Lys Asn Cys Leu Lys Gly Ala Gly Lys Thr Lys
            165                 170                 175 gta aaa gaa ctc ctc att gat gag aag ttt caa aaa tta ttt gag gat      753
Val Lys Glu Leu Leu Ile Asp Glu Lys Phe Gln Lys Leu Phe Glu Asp
        180                 185                 190 gac acg aaa gcc agt cat gta aaa gaa ata ctt aca gac agt aac gct      801
Asp Thr Lys Ala Ser His Val Lys Glu Ile Leu Thr Asp Ser Asn Ala
    195                 200                 205 aag gaa ata ctc aca aat gaa gta gca aaa gag gta cta aaa tcc gat      849
Lys Glu Ile Leu Thr Asn Glu Val Ala Lys Glu Val Leu Lys Ser Asp
210                 215                 220                 225 aaa ttt aaa gat gca ata act ggt gct ggt aag gac gca cta aaa gag      897
Lys Phe Lys Asp Ala Ile Thr Gly Ala Gly Lys Asp Ala Leu Lys Glu
                230                 235                 240 ata ctt act tgc gat aaa ttt aaa gat gca gta aca ggt aat ggt aag      945
Ile Leu Thr Cys Asp Lys Phe Lys Asp Ala Val Thr Gly Asn Gly Lys
            245                 250                 255 gac gca cta aaa gaa ata ctt act tgc gat aaa ttt aaa gat gca gta      993
Asp Ala Leu Lys Glu Ile Leu Thr Cys Asp Lys Phe Lys Asp Ala Val
        260                 265                 270 aca ggc aat ggt aaa gac aag cta aaa gag att ctt act cac gag aag     1041
Thr Gly Asn Gly Lys Asp Lys Leu Lys Glu Ile Leu Thr His Glu Lys
    275                 280                 285 ttt aaa gca ctc ata gag agt gaa ggc aaa gac ata ctg aaa gaa att     1089
Phe Lys Ala Leu Ile Glu Ser Glu Gly Lys Asp Ile Leu Lys Glu Ile
290                 295                 300                 305 ctt aca gat agt acc ggt aaa ttt aaa gag cta ata gaa agc act ggt     1137
Leu Thr Asp Ser Thr Gly Lys Phe Lys Glu Leu Ile Glu Ser Thr Gly
                310                 315                 320 aaa gac aag cta aaa gag att ttc aca gat aac acc ggt aac ttt aaa     1185
Lys Asp Lys Leu Lys Glu Ile Phe Thr Asp Asn Thr Gly Asn Phe Lys
            325                 330                 335 ggg ctt gta gaa ggc gcc ggt aag gat gaa gca aaa gca gta ctt act     1233
Gly Leu Val Glu Gly Ala Gly Lys Asp Glu Ala Lys Ala Val Leu Thr
        340                 345                 350 cac gag aaa ttt aaa gac ttg ttt aat gac aaa aca aca gct ggc tac     1281
His Glu Lys Phe Lys Asp Leu Phe Asn Asp Lys Thr Thr Ala Gly Tyr
```

-continued

```
    355                 360                 365 gtg aaa gaa ata ctc acc agt gat aag ttt aaa aaa tta ttt gag gac      1329
Val Lys Glu Ile Leu Thr Ser Asp Lys Phe Lys Lys Leu Phe Glu Asp
370                 375                 380                 385 aat acc aaa gct ggc tac gtg aaa gaa ata ctc acg aac gat aca gct      1377
Asn Thr Lys Ala Gly Tyr Val Lys Glu Ile Leu Thr Asn Asp Thr Ala
                390                 395                 400 aag gaa ata ctc aca aat caa aca gct aaa gaa gtc cta aaa gac agc      1425
Lys Glu Ile Leu Thr Asn Gln Thr Ala Lys Glu Val Leu Lys Asp Ser
            405                 410                 415 aca gcc aaa gaa ata cta aaa tgc gat aaa ttt aag gac gca ata aca      1473
Thr Ala Lys Glu Ile Leu Lys Cys Asp Lys Phe Lys Asp Ala Ile Thr
        420                 425                 430 ggc gct ggt aaa gat gag cta aaa tac ata ctc act aat aac gag ttt      1521
Gly Ala Gly Lys Asp Glu Leu Lys Tyr Ile Leu Thr Asn Asn Glu Phe
    435                 440                 445 aaa agc tta ttt gat agc aaa gat agc gct gaa gct gtt aaa gca ata      1569
Lys Ser Leu Phe Asp Ser Lys Asp Ser Ala Glu Ala Val Lys Ala Ile
450                 455                 460                 465 ttt acc cac aat aag ttt aaa gaa cta ctt aaa acg tgc aag gac aac      1617
Phe Thr His Asn Lys Phe Lys Glu Leu Leu Lys Thr Cys Lys Asp Asn
                470                 475                 480 cca aaa aat acg gcg gcg ctt gca gct gct tta gat gaa cta aaa gat      1665
Pro Lys Asn Thr Ala Ala Leu Ala Ala Ala Leu Asp Glu Leu Lys Asp
            485                 490                 495 cta att acg tgt gac cgc aat aat cat gca aca aaa cta caa gcc ttt      1713
Leu Ile Thr Cys Asp Arg Asn Asn His Ala Thr Lys Leu Gln Ala Phe
        500                 505                 510 gga agt gca cta tgc acc aga aaa aaa gag tcg tgc gat aat ttt agc      1761
Gly Ser Ala Leu Cys Thr Arg Lys Lys Glu Ser Cys Asp Asn Phe Ser
    515                 520                 525 cct gca agc tgc agt agt aca gca gct aca taattacgta gcgctaggtg       1811
Pro Ala Ser Cys Ser Ser Thr Ala Ala Thr
530                 535 ggggtaaatt acccccacct acgtagaatc acacggggaa ctttctctct attactgagg   1871
tcttaggatt tactttcaaa ttactatgac agccgattaa attattatga cagacgatac   1931
actttt                                                              1937

<210> SEQ ID NO 6
<211> LENGTH: 539
<212> TYPE: PRT
<213> ORGANISM: Ehrlichia risticii
<400> SEQUENCE: 6

Met Ser Asn Glu Thr Leu Leu Ser Val Leu Ser Asp Glu Thr His Phe
  1               5                  10                  15

Ala Asn Leu Val Asp Glu Leu Leu Leu Ser Leu Val Lys Asp Ser Ile
            20                  25                  30

Phe Thr Gln Val Ile Lys Gly Glu Gly Lys Thr Glu Leu Lys Asp Ile
        35                  40                  45

Leu Thr Asp Ser Thr Gly Lys Phe Lys Glu Leu Ile Gly Ser Ser Gly
     50                  55                  60

Lys Asp Ile Leu Lys Ser Ile His Thr Asp Gly Ser Gly Asn Phe Lys
 65                  70                  75                  80

Gly Leu Ile Gln Ser Thr Gly Lys Ala Glu Val Lys Glu Val Leu Thr
                 85                  90                  95

Asn Glu Lys Phe Lys Glu Leu Phe Gly Ser Glu Gly Lys Asp Ile Leu
```

-continued

```
                100                 105                 110
Lys Glu Ile Leu Thr Asp Asn Thr Gly Asn Phe Lys Gly Leu Ile Glu
                115                 120                 125
Gly Lys Gly Lys Asp Glu Ala Lys Gly Val Leu Thr Asp Glu Lys Phe
            130                 135                 140
Lys Gly Leu Phe Asp Asp Lys Thr Ile Ala Gly Tyr Val Lys Glu Ile
145                 150                 155                 160
Leu Thr Ser Glu Ser Leu Lys Asn Cys Leu Lys Gly Ala Gly Lys Thr
                165                 170                 175
Lys Val Lys Glu Leu Leu Ile Asp Glu Lys Phe Gln Lys Leu Phe Glu
                180                 185                 190
Asp Asp Thr Lys Ala Ser His Val Lys Glu Ile Leu Thr Asp Ser Asn
                195                 200                 205
Ala Lys Glu Ile Leu Thr Asn Glu Val Ala Lys Glu Val Leu Lys Ser
            210                 215                 220
Asp Lys Phe Lys Asp Ala Ile Thr Gly Ala Gly Lys Asp Ala Leu Lys
225                 230                 235                 240
Glu Ile Leu Thr Cys Asp Lys Phe Lys Asp Ala Val Thr Gly Asn Gly
                245                 250                 255
Lys Asp Ala Leu Lys Glu Ile Leu Thr Cys Asp Lys Phe Lys Asp Ala
            260                 265                 270
Val Thr Gly Asn Gly Lys Asp Lys Leu Lys Glu Ile Leu Thr His Glu
            275                 280                 285
Lys Phe Lys Ala Leu Ile Glu Ser Glu Gly Lys Asp Ile Leu Lys Glu
            290                 295                 300
Ile Leu Thr Asp Ser Thr Gly Lys Phe Lys Glu Leu Ile Glu Ser Thr
305                 310                 315                 320
Gly Lys Asp Lys Leu Lys Glu Ile Phe Thr Asp Asn Thr Gly Asn Phe
                325                 330                 335
Lys Gly Leu Val Glu Gly Ala Gly Lys Asp Glu Ala Lys Ala Val Leu
            340                 345                 350
Thr His Glu Lys Phe Lys Asp Leu Phe Asn Asp Lys Thr Thr Ala Gly
            355                 360                 365
Tyr Val Lys Glu Ile Leu Thr Ser Asp Lys Phe Lys Lys Leu Phe Glu
            370                 375                 380
Asp Asn Thr Lys Ala Gly Tyr Val Lys Glu Ile Leu Thr Asn Asp Thr
385                 390                 395                 400
Ala Lys Glu Ile Leu Thr Asn Gln Thr Ala Lys Glu Val Leu Lys Asp
                405                 410                 415
Ser Thr Ala Lys Glu Ile Leu Lys Cys Asp Lys Phe Lys Asp Ala Ile
            420                 425                 430
Thr Gly Ala Gly Lys Asp Glu Leu Lys Tyr Ile Leu Thr Asn Asn Glu
            435                 440                 445
Phe Lys Ser Leu Phe Asp Ser Lys Asp Ser Ala Glu Ala Val Lys Ala
            450                 455                 460
Ile Phe Thr His Asn Lys Phe Lys Glu Leu Leu Lys Thr Cys Lys Asp
465                 470                 475                 480
Asn Pro Lys Asn Thr Ala Ala Leu Ala Ala Leu Asp Glu Leu Lys
                485                 490                 495
Asp Leu Ile Thr Cys Asp Arg Asn Asn His Ala Thr Lys Leu Gln Ala
                500                 505                 510
Phe Gly Ser Ala Leu Cys Thr Arg Lys Lys Glu Ser Cys Asp Asn Phe
            515                 520                 525
```

-continued

```
Ser Pro Ala Ser Cys Ser Ser Thr Ala Ala Thr
    530                 535

<210> SEQ ID NO 7
<211> LENGTH: 1791
<212> TYPE: DNA
<213> ORGANISM: Ehrlichia risticii
<220> FEATURE:
<221> NAME/KEY: CDS
<222> LOCATION: (175)..(1677)

<400> SEQUENCE: 7
attggatcta aataatgtac actggaggtt cgtattttct attatgaaag ggatagaatg      60
ttaaatttta tgatttttta taataaaaat agatataaaa tttagtagtt ttataaattt     120
ttcataacaa aggactatcc tccttgcata aaatttctaa gacgaaaaat cctt atg       177
                                                            Met
                                                              1 tca aat gaa aca ctt ctg agc gta ctt tct gat gaa acg cac ttt gct       225
Ser Asn Glu Thr Leu Leu Ser Val Leu Ser Asp Glu Thr His Phe Ala
            5                  10                  15 aat cta gtt gat gaa ctt ctt ctc agc ttg gtt aaa gac agt att ttc       273
Asn Leu Val Asp Glu Leu Leu Leu Ser Leu Val Lys Asp Ser Ile Phe
        20                  25                  30 act caa gta ata aaa ggc gag gga aag aca gaa tta aaa gac att ctt       321
Thr Gln Val Ile Lys Gly Glu Gly Lys Thr Glu Leu Lys Asp Ile Leu
     35                  40                  45 aca gat agc act ggc aag ttt aaa gag ctg ata gga agt agc ggt aag       369
Thr Asp Ser Thr Gly Lys Phe Lys Glu Leu Ile Gly Ser Ser Gly Lys
 50                  55                  60                  65 gat ata cta aaa agc ata ctc aca gat ggc tca ggc aac ttt aaa ggc       417
Asp Ile Leu Lys Ser Ile Leu Thr Asp Gly Ser Gly Asn Phe Lys Gly
                 70                  75                  80 ctt ata caa agc aca ggt aag gca gaa gta aaa gag gta ctc act aat       465
Leu Ile Gln Ser Thr Gly Lys Ala Glu Val Lys Glu Val Leu Thr Asn
             85                  90                  95 gaa aaa ttc aaa gag ctt ttt gga agc gat ggt aag gat ata tta aaa       513
Glu Lys Phe Lys Glu Leu Phe Gly Ser Asp Gly Lys Asp Ile Leu Lys
        100                 105                 110 gac ata ctc aca gat agc act ggt aag ttt aaa gag ctg ata gga agt       561
Asp Ile Leu Thr Asp Ser Thr Gly Lys Phe Lys Glu Leu Ile Gly Ser
    115                 120                 125 agc ggt aag gac ata cta aaa aac att ctt aca gat agc acc ggt aag       609
Ser Gly Lys Asp Ile Leu Lys Asn Ile Leu Thr Asp Ser Thr Gly Lys
130                 135                 140                 145 ttt aaa gaa ctt ata gaa agt gca ggt aag ggt aag ctg aaa gac ctt       657
Phe Lys Glu Leu Ile Glu Ser Ala Gly Lys Gly Lys Leu Lys Asp Leu
                150                 155                 160 ctt att gat gga aac ttt aaa aaa tta ttt gag gat gac acg aaa gct       705
Leu Ile Asp Gly Asn Phe Lys Lys Leu Phe Glu Asp Asp Thr Lys Ala
            165                 170                 175 gct cat gta aaa gaa ata ctt aca gac agc aac gct aag gaa ata ctc       753
Ala His Val Lys Glu Ile Leu Thr Asp Ser Asn Ala Lys Glu Ile Leu
        180                 185                 190 aca aat gaa gta gca aaa gag gta cta aaa tcc gat aaa ttt aaa gat       801
Thr Asn Glu Val Ala Lys Glu Val Leu Lys Ser Asp Lys Phe Lys Asp
    195                 200                 205 gca ata act ggt gct ggt aag gac gca cta aaa gag ata ctt act tgc       849
Ala Ile Thr Gly Ala Gly Lys Asp Ala Leu Lys Glu Ile Leu Thr Cys
210                 215                 220                 225
```

-continued

```
gat aaa ttt aaa gat gca gta aca ggc aat ggt aag gac gca cta aaa         897
Asp Lys Phe Lys Asp Ala Val Thr Gly Asn Gly Lys Asp Ala Leu Lys
            230                 235                 240 gaa ata ctt act tgc gat aaa ttt aaa gat gca gta aca ggc aat ggt         945
Glu Ile Leu Thr Cys Asp Lys Phe Lys Asp Ala Val Thr Gly Asn Gly
        245                 250                 255 aaa gac aag cta aaa gag att ctt act cac gag aag ttt aaa gca ctc         993
Lys Asp Lys Leu Lys Glu Ile Leu Thr His Glu Lys Phe Lys Ala Leu
    260                 265                 270 ata gag agt gaa ggc aaa gac ata ctg aaa gac att ctt aca gat agt        1041
Ile Glu Ser Glu Gly Lys Asp Ile Leu Lys Asp Ile Leu Thr Asp Ser
275                 280                 285 acc ggt aaa ttt aaa gag cta ata gaa agc acg ggt aag gat gaa gca        1089
Thr Gly Lys Phe Lys Glu Leu Ile Glu Ser Thr Gly Lys Asp Glu Ala
290                 295                 300                 305 aaa gca gta ctt act gac gag aaa ttt aaa gac ttg ttt aat gac aaa        1137
Lys Ala Val Leu Thr Asp Glu Lys Phe Lys Asp Leu Phe Asn Asp Lys
            310                 315                 320 aca aca gct ggc tac gtg aaa gaa ata ctc acc agt gat aag ttt aaa        1185
Thr Thr Ala Gly Tyr Val Lys Glu Ile Leu Thr Ser Asp Lys Phe Lys
        325                 330                 335 aaa tta ttt gag gac aat acc aaa gct ggc tac gtg aaa gaa ata ctc        1233
Lys Leu Phe Glu Asp Asn Thr Lys Ala Gly Tyr Val Lys Glu Ile Leu
    340                 345                 350 acg aac gat aca gct aag gaa ata ctt acc aat cat aaa ttt aag gaa        1281
Thr Asn Asp Thr Ala Lys Glu Ile Leu Thr Asn His Lys Phe Lys Glu
355                 360                 365 gca ata act ggc gat ggt aaa gac ata ctg aaa gaa att ctt aca gat        1329
Ala Ile Thr Gly Asp Gly Lys Asp Ile Leu Lys Glu Ile Leu Thr Asp
370                 375                 380                 385 agc act ggt aac ttt aaa ggc gca ata aca ggt gcc ggt aaa gat cag        1377
Ser Thr Gly Asn Phe Lys Gly Ala Ile Thr Gly Ala Gly Lys Asp Gln
            390                 395                 400 cta aaa tac ata ctc act aat agc gag ttt aaa agc tta ttt gat agc        1425
Leu Lys Tyr Ile Leu Thr Asn Ser Glu Phe Lys Ser Leu Phe Asp Ser
        405                 410                 415 aaa gat agc gct gaa gct gtt aaa gaa ata ttt acc cac agt aag ttt        1473
Lys Asp Ser Ala Glu Ala Val Lys Glu Ile Phe Thr His Ser Lys Phe
    420                 425                 430 aaa gaa cta ctt aaa acg tgc aag gac aac cca aaa aat acg gcg gcg        1521
Lys Glu Leu Leu Lys Thr Cys Lys Asp Asn Pro Lys Asn Thr Ala Ala
435                 440                 445 ctt gca gct gct tta gat gaa cta aaa gat cta att acc tgt ggc agc        1569
Leu Ala Ala Ala Leu Asp Glu Leu Lys Asp Leu Ile Thr Cys Gly Ser
450                 455                 460                 465 ggt gat cat gca aca aaa cta caa gcc ttt gga agt gca cta tgc acc        1617
Gly Asp His Ala Thr Lys Leu Gln Ala Phe Gly Ser Ala Leu Cys Thr
            470                 475                 480 aga aaa aaa gag tcg tgc gat aat ttt agc tct gca aac tgc agt agt        1665
Arg Lys Lys Glu Ser Cys Asp Asn Phe Ser Ser Ala Asn Cys Ser Ser
        485                 490                 495 aca aca act gca taattacgta gcgctaggtg ggggtaattt accccccacct          1717
Thr Thr Thr Ala
            500 agctagaatc acacggggaa ctttctctct attactaggg tcttaggatt acaaacaaat     1777 tactatgaca gcca                                                       1791
```

<210> SEQ ID NO 8
<211> LENGTH: 501

```
<212> TYPE: PRT
<213> ORGANISM: Ehrlichia risticii

<400> SEQUENCE: 8
```

| | | | | | | | | | | | | | | |
|---|---|---|---|---|---|---|---|---|---|---|---|---|---|---|
| Met | Ser | Asn | Glu | Thr | Leu | Leu | Ser | Val | Leu | Ser | Asp | Glu | Thr | His | Phe |
| 1 | | | | 5 | | | | | 10 | | | | | 15 | |
| Ala | Asn | Leu | Val | Asp | Glu | Leu | Leu | Ser | Leu | Val | Lys | Asp | Ser | Ile |
| | | | 20 | | | | | 25 | | | | | 30 | |
| Phe | Thr | Gln | Val | Ile | Lys | Gly | Glu | Gly | Lys | Thr | Glu | Leu | Lys | Asp | Ile |
| | | | 35 | | | | 40 | | | | | 45 | | |
| Leu | Thr | Asp | Ser | Thr | Gly | Lys | Phe | Lys | Glu | Leu | Ile | Gly | Ser | Ser | Gly |
| | 50 | | | | | | 55 | | | | | 60 | | | |
| Lys | Asp | Ile | Leu | Lys | Ser | Ile | Leu | Thr | Asp | Gly | Ser | Gly | Asn | Phe | Lys |
| 65 | | | | | 70 | | | | | 75 | | | | | 80 |
| Gly | Leu | Ile | Gln | Ser | Thr | Gly | Lys | Ala | Glu | Val | Lys | Glu | Val | Leu | Thr |
| | | | | 85 | | | | | 90 | | | | | 95 | |
| Asn | Glu | Lys | Phe | Lys | Glu | Leu | Phe | Gly | Ser | Asp | Gly | Lys | Asp | Ile | Leu |
| | | | | 100 | | | | | 105 | | | | | 110 | |
| Lys | Asp | Ile | Leu | Thr | Asp | Ser | Thr | Gly | Lys | Phe | Lys | Glu | Leu | Ile | Gly |
| | | | 115 | | | | | 120 | | | | | 125 | | |
| Ser | Ser | Gly | Lys | Asp | Ile | Leu | Lys | Asn | Ile | Leu | Thr | Asp | Ser | Thr | Gly |
| | 130 | | | | | 135 | | | | | 140 | | | | |
| Lys | Phe | Lys | Glu | Leu | Ile | Glu | Ser | Ala | Gly | Lys | Gly | Lys | Leu | Lys | Asp |
| 145 | | | | | 150 | | | | | 155 | | | | | 160 |
| Leu | Leu | Ile | Asp | Gly | Asn | Phe | Lys | Lys | Leu | Phe | Glu | Asp | Asp | Thr | Lys |
| | | | | 165 | | | | | 170 | | | | | 175 | |
| Ala | Ala | His | Val | Lys | Glu | Ile | Leu | Thr | Asp | Ser | Asn | Ala | Lys | Glu | Ile |
| | | | | 180 | | | | | 185 | | | | | 190 | |
| Leu | Thr | Asn | Glu | Val | Ala | Lys | Glu | Val | Leu | Lys | Ser | Asp | Lys | Phe | Lys |
| | | | 195 | | | | | 200 | | | | | 205 | | |
| Asp | Ala | Ile | Thr | Gly | Ala | Gly | Lys | Asp | Ala | Leu | Lys | Glu | Ile | Leu | Thr |
| | 210 | | | | | 215 | | | | | 220 | | | | |
| Cys | Asp | Lys | Phe | Lys | Asp | Ala | Val | Thr | Gly | Asn | Gly | Lys | Asp | Ala | Leu |
| 225 | | | | | 230 | | | | | 235 | | | | | 240 |
| Lys | Glu | Ile | Leu | Thr | Cys | Asp | Lys | Phe | Lys | Asp | Ala | Val | Thr | Gly | Asn |
| | | | | 245 | | | | | 250 | | | | | 255 | |
| Gly | Lys | Asp | Lys | Leu | Lys | Glu | Ile | Leu | Thr | His | Glu | Lys | Phe | Lys | Ala |
| | | | 260 | | | | | 265 | | | | | 270 | | |
| Leu | Ile | Glu | Ser | Glu | Gly | Lys | Asp | Ile | Leu | Lys | Asp | Ile | Leu | Thr | Asp |
| | | 275 | | | | | 280 | | | | | 285 | | | |
| Ser | Thr | Gly | Lys | Phe | Lys | Glu | Leu | Ile | Glu | Ser | Thr | Gly | Lys | Asp | Glu |
| | 290 | | | | | 295 | | | | | 300 | | | | |
| Ala | Lys | Ala | Val | Leu | Thr | Asp | Glu | Lys | Phe | Lys | Asp | Leu | Phe | Asn | Asp |
| 305 | | | | | 310 | | | | | 315 | | | | | 320 |
| Lys | Thr | Thr | Ala | Gly | Tyr | Val | Lys | Glu | Ile | Leu | Thr | Ser | Asp | Lys | Phe |
| | | | | 325 | | | | | 330 | | | | | 335 | |
| Lys | Lys | Leu | Phe | Glu | Asp | Asn | Thr | Lys | Ala | Gly | Tyr | Val | Lys | Glu | Ile |
| | | | | 340 | | | | | 345 | | | | | 350 | |
| Leu | Thr | Asn | Asp | Thr | Ala | Lys | Glu | Ile | Leu | Thr | Asn | His | Lys | Phe | Lys |
| | | | 355 | | | | | 360 | | | | | 365 | | |
| Glu | Ala | Ile | Thr | Gly | Asp | Gly | Lys | Asp | Ile | Leu | Lys | Glu | Ile | Leu | Thr |
| | | 370 | | | | | 375 | | | | | 380 | | | |
| Asp | Ser | Thr | Gly | Asn | Phe | Lys | Gly | Ala | Ile | Thr | Gly | Ala | Gly | Lys | Asp |
| 385 | | | | | 390 | | | | | 395 | | | | | 400 |

```
Gln Leu Lys Tyr Ile Leu Thr Asn Ser Glu Phe Lys Ser Leu Phe Asp
                405                 410                 415

Ser Lys Asp Ser Ala Glu Ala Val Lys Glu Ile Phe Thr His Ser Lys
            420                 425                 430

Phe Lys Glu Leu Leu Lys Thr Cys Lys Asp Asn Pro Lys Asn Thr Ala
        435                 440                 445

Ala Leu Ala Ala Leu Asp Glu Leu Lys Asp Leu Ile Thr Cys Gly
    450                 455                 460

Ser Gly Asp His Ala Thr Lys Leu Gln Ala Phe Gly Ser Ala Leu Cys
465                 470                 475                 480

Thr Arg Lys Lys Glu Ser Cys Asp Asn Phe Ser Ser Ala Asn Cys Ser
                485                 490                 495

Ser Thr Thr Thr Ala
            500
```

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 9
cataaaattt ctaagacgaa ggatccctat gtc                              33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 10
gagagaaagt tccccgtgtg aattctagct agg                              33

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 11
atactaaaaa gcatactc                                               18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 12
ttctacaagc cctttaaa                                               18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 13

-continued gaatgttcag ctttccgg 18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 14
agctgtatcg ttcgtgag 18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 15
gtatacttac agatagcac 19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 16
gccgacagta tcattaaac 19

<210> SEQ ID NO 17
<211> LENGTH: 11
<212> TYPE: DNA
<213> ORGANISM: Artificial Sequence

<400> SEQUENCE: 17
aaagaaatac t 11

<210> SEQ ID NO 18
<211> LENGTH: 11
<212> TYPE: DNA
<213> ORGANISM: Ehrlichia risticii

<400> SEQUENCE: 18
gaaatactca c 11

<210> SEQ ID NO 19
<211> LENGTH: 11
<212> TYPE: DNA
<213> ORGANISM: Ehrlichia risticii

<400> SEQUENCE: 19
aaatttaaag a 11

<210> SEQ ID NO 20
<211> LENGTH: 11
<212> TYPE: DNA
<213> ORGANISM: Ehrlichia risticii

<400> SEQUENCE: 20
ctaaaagaga t 11

```
<210> SEQ ID NO 21
<211> LENGTH: 11
<212> TYPE: DNA
<213> ORGANISM: Ehrlichia risticii

<400> SEQUENCE: 21
aaagacatac t                                                          11

<210> SEQ ID NO 22
<211> LENGTH: 11
<212> TYPE: DNA
<213> ORGANISM: Ehrlichia risticii

<400> SEQUENCE: 22
tttaaagagc t                                                          11

<210> SEQ ID NO 23
<211> LENGTH: 11
<212> TYPE: DNA
<213> ORGANISM: Ehrlichia risticii

<400> SEQUENCE: 23 atttttttata a                                                         11

<210> SEQ ID NO 24
<211> LENGTH: 11
<212> TYPE: DNA
<213> ORGANISM: Ehrlichia risticii

<400> SEQUENCE: 24
aactttaaag g                                                          11

<210> SEQ ID NO 25
<211> LENGTH: 11
<212> TYPE: DNA
<213> ORGANISM: Ehrlichia risticii

<400> SEQUENCE: 25
aagtttaaag a                                                          11

<210> SEQ ID NO 26
<211> LENGTH: 11
<212> TYPE: DNA
<213> ORGANISM: Ehrlichia risticii

<400> SEQUENCE: 26
tactcactaa t                                                          11

<210> SEQ ID NO 27
<211> LENGTH: 11
<212> TYPE: DNA
<213> ORGANISM: Ehrlichia risticii

<400> SEQUENCE: 27
agtttaaaaa a                                                          11

<210> SEQ ID NO 28
<211> LENGTH: 11
<212> TYPE: DNA
<213> ORGANISM: Ehrlichia risticii

<400> SEQUENCE: 28
ataagtttaa a                                                          11
```

-continued

<210> SEQ ID NO 29
<211> LENGTH: 11
<212> TYPE: DNA
<213> ORGANISM: Ehrlichia risticii

<400> SEQUENCE: 29
atacttacag a 11

<210> SEQ ID NO 30
<211> LENGTH: 11
<212> TYPE: DNA
<213> ORGANISM: Ehrlichia risticii

<400> SEQUENCE: 30
aaatttaaag a 11

<210> SEQ ID NO 31
<211> LENGTH: 11
<212> TYPE: DNA
<213> ORGANISM: Ehrlichia risticii

<400> SEQUENCE: 31
ctaaaagaga t 11

<210> SEQ ID NO 32
<211> LENGTH: 11
<212> TYPE: DNA
<213> ORGANISM: Ehrlichia risticii

<400> SEQUENCE: 32
aaagaaatac t 11

<210> SEQ ID NO 33
<211> LENGTH: 11
<212> TYPE: DNA
<213> ORGANISM: Ehrlichia risticii

<400> SEQUENCE: 33
tacttacaga t 11

<210> SEQ ID NO 34
<211> LENGTH: 11
<212> TYPE: DNA
<213> ORGANISM: Ehrlichia risticii

<400> SEQUENCE: 34
aaagacatac t 11

<210> SEQ ID NO 35
<211> LENGTH: 11
<212> TYPE: DNA
<213> ORGANISM: Ehrlichia risticii

<400> SEQUENCE: 35
acagctaaag a 11

<210> SEQ ID NO 36
<211> LENGTH: 11
<212> TYPE: DNA
<213> ORGANISM: Ehrlichia risticii

<400> SEQUENCE: 36

-continued tttaaagaac t    11

<210> SEQ ID NO 37
<211> LENGTH: 11
<212> TYPE: DNA
<213> ORGANISM: Ehrlichia risticii

<400> SEQUENCE: 37
gaaatactta c    11

<210> SEQ ID NO 38
<211> LENGTH: 11
<212> TYPE: DNA
<213> ORGANISM: Ehrlichia risticii

<400> SEQUENCE: 38
agcactggta a    11

<210> SEQ ID NO 39
<211> LENGTH: 11
<212> TYPE: DNA
<213> ORGANISM: Ehrlichia risticii

<400> SEQUENCE: 39
gataaattta a    11

<210> SEQ ID NO 40
<211> LENGTH: 11
<212> TYPE: DNA
<213> ORGANISM: Ehrlichia risticii

<400> SEQUENCE: 40
cttatagaaa g    11

<210> SEQ ID NO 41
<211> LENGTH: 11
<212> TYPE: DNA
<213> ORGANISM: Ehrlichia risticii

<400> SEQUENCE: 41
gaaatactca c    11

<210> SEQ ID NO 42
<211> LENGTH: 11
<212> TYPE: DNA
<213> ORGANISM: Ehrlichia risticii

<400> SEQUENCE: 42
accggtaact t    11

<210> SEQ ID NO 43
<211> LENGTH: 11
<212> TYPE: DNA
<213> ORGANISM: Ehrlichia risticii

<400> SEQUENCE: 43
atgcaacaaa a    11

<210> SEQ ID NO 44
<211> LENGTH: 11
<212> TYPE: DNA
<213> ORGANISM: Ehrlichia risticii

<400> SEQUENCE: 44

-continued

```
gctaaagaag t                                                  11

<210> SEQ ID NO 45
<211> LENGTH: 11
<212> TYPE: DNA
<213> ORGANISM: Ehrlichia risticii

<400> SEQUENCE: 45
cttacagata a                                                  11

<210> SEQ ID NO 46
<211> LENGTH: 11
<212> TYPE: DNA
<213> ORGANISM: Ehrlichia risticii

<400> SEQUENCE: 46
gcaataactg g                                                  11

<210> SEQ ID NO 47
<211> LENGTH: 11
<212> TYPE: DNA
<213> ORGANISM: Ehrlichia risticii

<400> SEQUENCE: 47
atggtaagga c                                                  11

<210> SEQ ID NO 48
<211> LENGTH: 11
<212> TYPE: DNA
<213> ORGANISM: Ehrlichia risticii

<400> SEQUENCE: 48
acttatagaa g                                                  11
```

SIZE-VARIABLE STRAIN-SPECIFIC PROTECTIVE ANTIGEN FOR POTOMAC HORSE FEVER

This application claims the benefit of priority under 35 U.S.C. §119(e) to U.S. Provisional Application Ser. No. 60/059,252, filed on Sep. 18, 1997.

BACKGROUND OF THE INVENTION

1. Field of the Invention

The present invention relates to isolated and purified antigen which is expressed by a wild-type *E. risticii* strain and is specific to the strain. The present invention also relates to nucleic acid constructs which encode the antigen, expression vectors, transformed host cells, and methods for producing the antigen.

2. Discussion of the Background

Potomac horse fever (PHF), also known as equine monocytic ehrlichiosis (EME), is an acute infectious disease of horses. PHF was initially recognized in 1979 in areas along the Potomac river in Maryland and Virginia. The causative agent was subsequently identified in 1984 as *Ehrlichia risticii*, an obligatory intracellular rickettsial organism. Since then, PHF cases have been reported in many states of the U.S. and some provinces of Canada. Serological evidence suggests the presence of *E. risticii* in parts of Europe and Australia. The main disease features of PHF are fever, leukopenia, depression, anorexia and diarrhea. Some affected horses may also develop colic or laminitis. The mortality is as high as 20–25%. Recently, abortions in pregnant mares contracting the disease have been documented. PHF occurs mostly in the summer months. Although most of the rickettsial pathogens are transmitted by arthropod vectors and the seasonality of PHF also suggests this, all attempts to reveal the mode of transmission of *E. risticii* have been unsuccessful.

*E. risticii* infection is responsible for substantial economic loss to the equine industry. Currently, inactivated vaccines for PHF are commercially available from three different manufacturers. In endemic areas, vaccination of equine population against PHF is performed on a regular basis. Despite this, PHF is occurring in increasing numbers, including in vaccinated horses. In 1990, *E. risticii* was isolated from a horse suffering from severe PHF in spite of carrying a high titer of antibodies from multiple PHF vaccinations. On Western blot analysis, the antigenic profile of this newly isolated organism (90-12 strain) was considerably different from that of the original organism (25-D strain) isolated in 1984 during the initial outbreaks of the disease. In subsequent years, more isolates were obtained from vaccinated horses suffering from clinical PHF. These findings suggested the possible existence of strain variation in *E. risticii* and its probable role in vaccine failures in the field.

In the last few years, significant progress has been made toward understanding the pathogenesis and host immune response in *E. risticii* infection. Certain strains of mice have been identified to be good laboratory models of PHF. Various serological and DNA based tests have been developed to better facilitate diagnosis of the infection. Studies to identify the antigenic composition of the organisms and the major surface antigens involved in immune response were conducted. However, most of these studies have been performed with the original *E. risticii* isolates (isolated during 1984–85) from different laboratories. Except for one recent report on biological diversity in *E. risticii* isolates, no systematic comparison between different isolates has been made to identify the extent and importance of strain variation in this organism. Also, very little is known about the molecular biology of *E. risticii*. Hence, the present study has been undertaken to: i) understand the differences between the 25-D and 90-12 strains of *E. risticii*; ii) investigate the molecular basis of these differences; iii) identify protective antigen(s).

In addition to the main focus of problem solving *E. risticii* infections, there is an important scientific interest in these studies to gain more knowledge on ehrlichial organisms in general. Along with *E. risticii*, genus Ehrlichia of the family Rickettsiaceae contains some other recently identified organisms. New members of this genus include *E. chaffeensis* and *E. ewingii*, pathogens of human and dog, respectively. Recently identified human granulocytic ehrlichiosis (HGE) has been demonstrated to be caused by an organism similar to or the same as *E. equi*, an equine pathogen. Also, *E. risticii* has been found to infect dogs and cats. Emergence of these ehrlichial diseases and changes in host specificity of ehrlichial organisms are quite intriguing. Information on the important proteins of *E. risticii* and the genes they are encoded by may provide us with necessary clues to understand the sophisticated intracellular survival strategies of ehrlichial organisms and the natural dynamics in their ecosystem that lead to changes in their life cycles.

SUMMARY OF THE INVENTION

The present invention is based on the discovery that strains of *Ehrlichia risticii* express surface antigens that are specific to the strain. These surface-expressed proteins are termed strain-specific antigens (SSAs). These antigens have now been isolated and purified from the respective strains. The SSAs of the present invention may be used to detect *Ehrlichia risticii* strains and to generate a protective immune response against *E. risticii* strains, leading to the development of more effective vaccines against PHF.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 1: Primers sequences ECP 1 and ECP 2 for amplifying any SSA gene (SEQ ID NO: 1 and 2).

FIG. 2: Nucleotide sequence of 85 kD gene with flanking regions and deduced amino acid sequence of the strain-specific antigen from *E. risticii* 90-12 strain (SEQ ID NO: 3 and 4). Putative −10, −35, RBS regions are underlined and putative starts of transcription is denoted (+1). The dyad symmetry, and the adjacent thymine-rich regions are underlined.

FIG. 3: Nucleotide sequence of 50 kD gene with flanking regions and deduced amino acid sequence of the strain-specific antigen from *E. risticii* 25-D strain (SEQ ID NO: 5 and 6). Putative −10, −35, RBS regions are underlined and putative starts of transcription is denoted (+1). The dyad symmetry, and the adjacent thymine-rich regions are underlined.

FIG. 4: Nucleotide sequence of ATCC-50 kD gene with flanking regions and deduced amino acid sequence (SEQ ID NO: 7 and 8). Putative −10, −35, RBS regions are underlined and putative starts of transcription is denoted (+1). The dyad symmetry, and the adjacent thymine-rich regions are underlined.

FIG. 5: Analysis of deduced amino acid sequences of SSA homologues from two antigenic variants of *E. risticii* (SEQ ID NO: 4 and 6). There were a total of eight identical domains present in both 50 kD and 85 kD antigens. The number at the top show each identical domain. There were significantly high homology present in the corresponding domain of the same number. Minor amino acid changes in each domain in 85 kD identified after compared with 50 kD and marked by a black triangle head.

DETAILED DESCRIPTION OF THE INVENTION

Figure 6:
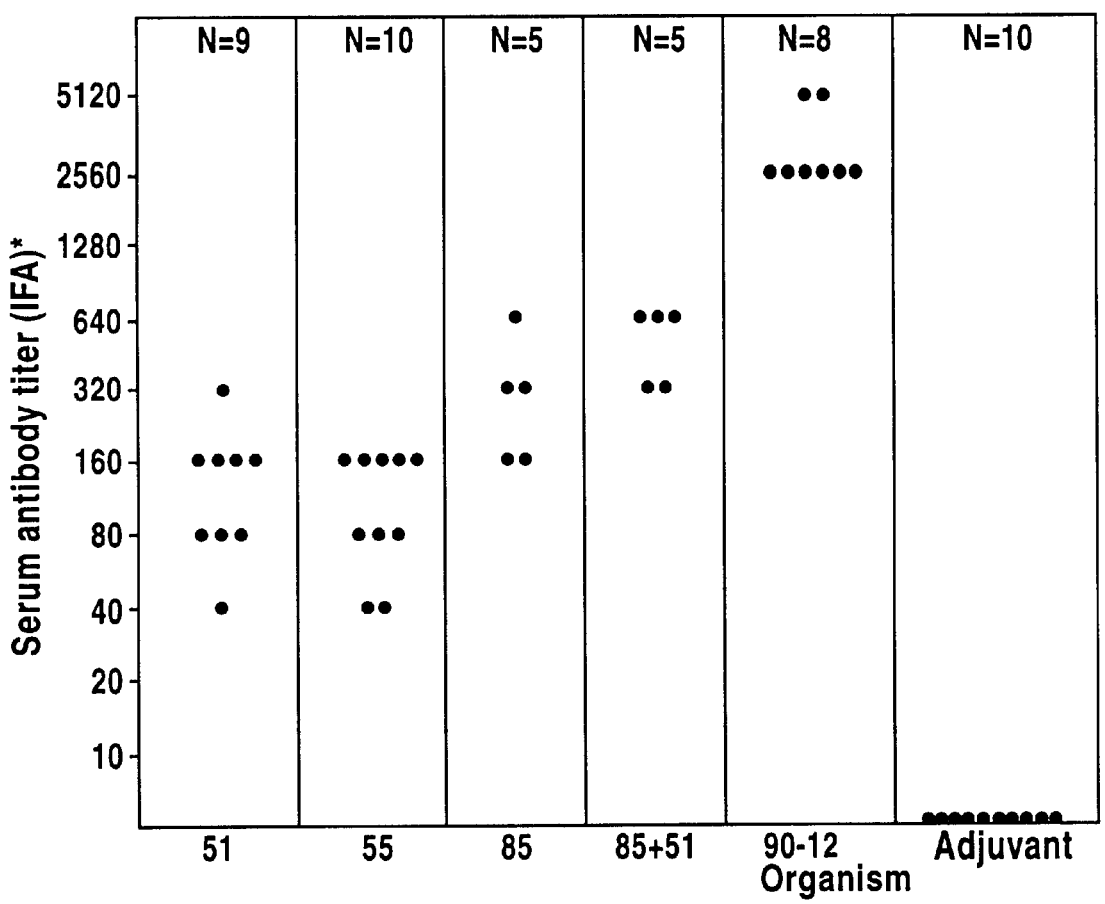
FIG. 6: Pre-challenge serum antibody titers of mice from different groups of experiment 1. All the antigens used for immunization of mice were from the 90-12 strain. Antibody titers were determined by performing indirect immunofluorescent assay (IFA). MM cells infected with the 90-12 strain were used in the IFA.

As used herein, the term "isolated and purified" refers to an antigen that has been separated and isolated from the *E. risticii* strain expressing the same. Preferably, the inventive SSA is separated from other proteins derived from *E. risticii*, especially other antigenic proteins.

The SSAs of the present invention may be obtained via PCR amplification from the genomic DNA of a wild-type *E. risticii* strain using well-known molecular biology techniques. Such techniques are well-known to those skilled in this art. The oligonucleotide primers for isolating a desired SSA gene may be prepared based on the specific nucleotide sequences disclosed herein. Specific examples of suitable primers are shown in FIG. 1 (SEQ ID NO: 1 and 2). For a discussion of PCR amplification, see *Current Protocols in Molecular Biology*, F. M. Ausubel et al, Eds., Volumes 1–3, John Wiley and Sons, 1998, incorporated herein by reference.

The SSA may vary widely in both overall size and amino acid composition. The SSA may have a molecular weight of about 40 to about 90 kDa, inclusive of all specific values and subranges therebetween. In specific embodiments of the present invention, the SSA has a molecular weight of about 50 kDa or 85 kDa. Examples of specific amino acid sequences of the inventive SSAs are shown in FIGS. 2–4 (SEQ ID NO: 9, 6 and 8).

The present invention also provides isolated and purified nucleic acids (e.g., recombinant DNAs) which encode the SSAs. Specific examples of nucleotide sequences encoding the SSA of the present invention are shown in FIGS. 2–4(SEQ ID NO: 3, 5 and 7). All nucleotide sequences encoding a particular SSA are included in the scope of the present invention. Selecting a nucleic acid encoding a particular amino acid sequence may be readily accomplished using the well-established genetic code relating the nucleic acid sequence of a codon sequence to the amino acid sequence encoded thereby. The genetic code is provided by R. H. Abeles et al, Biochemistry, Jones and Bartlett, 1992, p. 269, incorporated herein by reference in its entirety.

All percentage identities for the amino acid and DNA sequences noted above can be determined using a variety of algorithms known in the art. An example of a useful algorithm in this regard is the algorithm of Needleman and Wunsch, which is used in the "Gap" program by the Genetics Computer Group. This program finds alignment of two complete sequences that maximizes the number of matches and minimizes the number of gaps. Another useful algorithm is the algorithm of Smith and Waterman, which is used in the "BestFit" program by Genetics Computer Group. This program creates an optimal alignment of the best segment of similarity between two sequences. Optimal alignments are found by inserting gaps to maximize the number of matches using the local homology algorithm of Smith and Waterman. It is preferred to use the algorithm of Needleman and Wunsch to compare the amino acid and DNA percentage identity in the present case to another amino acid or DNA sequence.

The nucleic acid encoding the SSA may be incorporated into a vector suitable for directing the expression of the SSA in a suitable host (i.e., recombinant expression). Such expression vectors may have all of the customary transcriptional control elements which enable the SSA to be expressed in a host transformed with the vector. For a detailed discussion of expression vectors and related cloning technology, see *Current Protocols in Molecular Biology*, supra.

Suitable host cells include bacteria customarily used in the overproduction of recombinant protein sequences, e.g., *E. coli*. Mammalian cells may also be used as host cells if desired.

The inventive SSA may be produced by culturing a host cell transformed with an expression vector carrying the nucleic acid encoding the antigen in a suitable culture medium. The antigen is then isolated from the culture medium according to well-known procedures.

The isolated and purified SSA may be formulated into an immunogenic pharmaceutical composition by incorporating an effective amount of the antigen into a pharmaceutically acceptable carrier. Suitable carriers include, for example, aqueous solutions containing the customary components for administration to host, e.g., buffers, salts, adjuvants, etc. Upon administration of the composition to a host, the antigen induces a protective immune response against the *E. risticii* strain from which the antigen was derived. Preferably, such an immunogenic composition is a vaccine against the wild-type *E. risticii* strain from which the antigen was derived. Of course, in a preferred embodiment, the antigen also produces an immune response against other strains besides the wild-type strain from which the antigen is derived. In other words, a SSA from one strain may contain one or more epitopes which are shared with the SSA of other strains. A suitable host for the inventive immunogenic composition is, for example, a horse. The host may be any other animal that is susceptible to infection by *E. risticii*

(e.g., cats, dogs and humans). Formulating immunogenic pharmaceutical composition, administering the composition to a host, and determining the level of induced immune response are readily accomplished using techniques well-known to those skilled in this art.

Having generally described this invention, a further understanding can be obtained by reference to certain specific examples which are provided herein for purposes of illustration only and are not intended to be limiting unless otherwise specified.

EXAMPLES

Example 1

Isolation of Strain Specific Surface Antigen Gene of *Ehrlichia risticii*

*Ehrlichia risticii* Strains and DNA Preparation:

Two different strains of *E. risticii* were used for this study. The original *E. risticii* strain (25D) was isolated in 1984, during the initial outbreaks of PHF near the Potomac River bank in Maryland and Virginia. Recently the inventors isolated a new strain of *E. risticii* (90-12) from a vaccinated horse suffering from clinical PHF. These two strains of the organism were grown separately in human histiocyte cells and purification was accomplished over linear Renografin (Squibb, N.J.) density gradient centrifugation.

Propagation of *Ehrlichia risticii* in Cell Culture:

*E. risticii* strains were propagated a human histiocyte (HH) cell line (American Type culture Collection #U937). These cells were grown in RPMI 1640 medium (Flow Laboratories, McLean, Va.), supplemented with 4 mM L-glutamine (M.A. Bioproducts, Walkersville, Md.), and 15% fetal calf serum (Gibco Laboratories, Grand Island, N.Y.). Approximately $20 \times 10^6$ cells in the logarithmic phase of growth were centrifuged at 500×g for 10 minutes and the cell pellet was resuspended in 20 ml of *E. risticii* infected HH cell culture. This infected cell mixture was dispensed into a 150 cm$^2$ tissue culture flask and incubated at 37° C. in a humidified chamber in the presence of 5% $CO_2$ for one hour. Seventy ml of the growth medium was then added and the culture was incubated further.

The infected cell cultures were examined for infection by acridine orange staining according to a standard procedure. For this, about one ml of the cell suspension was centrifuged at 500×g for five minutes. The cell pellet, resuspended in about 50 μl of the supernatant, was applied onto a glass slide and allowed to air dry. The cells were fixed with absolute methanol for 10 minutes, stained with acridine orange stain for three minutes and examined with an ultraviolet microscope. The efficiency of infection of *E. risticii* was determined by considering the number and the intensity of orange specks of *E. risticii* inside the pale green stained cytoplasm of the HH cells.

The infected cultures were harvested on day 4–6 postinfection, depending upon the observed levels of infection. Infected HH cultures were centrifuged at 17,000×g for 20 minutes in a Sorvall refrigerated centrifuge (Sorvall, Norwalk, Conn.) and the cell pellet was resuspended in sodium-potassium-glutamine buffer to a final concentration of 50× and stored at −70° C.

Purification of *Ehrlichia risticii*:

*E. risticii* organisms were purified by centrifugation over a linear Renografin gradient according to known procedures described. Ten ml of 50× concentrate of infected HH culture were diluted with 20 ml of Tris buffer (10 mM Tris, pH 7.4). All the buffers contained 1.0 mM phenylmethylsulfonylfluoride (PMSF) and 1.0 mM iodoacetamide as proteinase inhibitors. The cell suspension was homogenized for three cycles in a Omni mixer (Dupont Co., Wilmington, Del.) at maximum setting for 30 seconds. Each cycle was followed with 30 seconds of cooling on ice. The homogenate was clarified at 2,000×g for 10 minutes to sediment the nuclear material and unbroken cells. The supernatant was centrifuged at 17,000×g for 20 minutes. The resulting pellet was resuspended in 2.0 ml of Tris buffer and the suspension was forced through 18 and 23 gauge needles to obtain homogeneity. The volume was brought up to 12 ml with Tris buffer containing 10 mM $MgSO_4$. Two μl (20 μg) of Dnase I (Life Technologies, Inc., Gaithersburg, Md.) were added to the suspension and incubation carried out at 37° C. for about 10 minutes to digest the liberated host nuclear material. Two ml of the suspension were then layered on about 34 ml of a 20 to 45% linear density gradient of Renografin (Squibb Chemical Co., New Brunswick, N.J.) in TEN buffer (50 mM Tris, pH8.0, 25 mM EDTA, 0.9% NcCl). The gradients containing ehrlichiae were centrifuged at 83,000×g for one hour at 4° C. The ehrlichiae were observed to band at a density of about 1.182 gm/ml and could be visualized well with a pointed light source. The cellular debris formed a compact band at the top of the gradient. The ehrlichial bands were collected and diluted with 10 volumes of Tris buffer and centrifuged at 17,000×g for 20 minutes to remove the Renografin. The purified *E. risticii* pellet then was resuspended in TEN buffer to a final concentration of 500× for the DNA experiments or to a final concentration of 200× in 10 mM tris buffer, pH7.4, for all the analyses.

Extraction of *Ehrlichia risticii* DNA:

Purified *E. risticii* suspension (500×) in TEN buffer was treated with lysozyme (Sigma Chemical Co., St. Louis, Mo.) at a final concentration of 2.0 mg/ml and incubated in a 37° C. water bath for 30 minutes. To this digest, SDS was added to a final concentration of 0.5% and the lysate was kept in a 65° C. water bath for an additional 30 minutes. This lysate was then treated with proteinase K (Bethesda Research Laboratories., Gaithersburg, Md.) at a final concentration of 400 mg/ml and was incubated in a 56° C. water bath overnight. Two phenol extractions were done with equal volumes of water saturated phenol and by shaking on a Orbitron rotator (VWR Scientific, Brisbane, Calif.) for 30 minutes each. Three chloroform (chloroform:isoamyl alcohol; 24:1) extractions were done and the DNA was precipitated by the addition of sodium acetate (pH 5.2) to a final concentration of 0.3M. Two volumes of absolute ethanol was added and incubation was carried out at −20° C. for two hours. The precipitate was pelleted by centrifugation at 12,000 rpm in a table top microcentrifuge for 15 minutes at 4° C. The DNA precipitate was washed once with 70% ethanol and then with absolute ethanol each followed by centrifugation at 4° C. The DNA pellet was allowed to dry in a vacuum for five to ten minutes and then it was dissolved in TE buffer (10 mM Tris, pH 8.0, 1.0 mM EDTA) to a concentration of 1.0 μg DNA/μl and stored at −20° C. for future use.

Polyacrylamide Gel Electrophoresis and Western Immunoblotting:

Discontinuous SDS PAGE analyses were carried out over 10 and 12% polyacrylamide gels according to the method of Laemmli (120). Gels were cast on a vertical slab gel electrophoresis system (Model SE 600, Hoeffer scientific Instrument, San Francisco, Calif.). For a 10% gel, 10 ml of acrylamide solution containing 30% acrylamide and 2.7% N,N'-methylene bisacrylamide were mixed with 7.5 ml of 1.5 M Tris buffer, pH 8.8, 150 μl of 20% SDS, and 10.5 ml of distilled water and degassed for 15 minutes under vacuum. Polymerization was initiated by the addition of 150 µl of 10% ammonium persulfate and 10 µl TEMED (N,N,N',N'-tetramethylethylene-diamine), and then the solution was poured immediately into the gel apparatus. About 1.0 ml of water saturated butanol was layered on top and the gel was allowed to polymerize for about 30 minutes. The stacking gel contained 1.33 ml of acrylamide solution, 2.5 ml of 0.5 M Tris buffer, pH 6.8, 100 µl of 10% SDS, 6.1 ml of water, 50 µl of 10% ammonium persulfate and 5.0 µl of Temed. The samples were dissolved in sample buffer (62.5 mM Tris, pH6.8, 2% SDS, 5% 2-mercaptoethanol, 10% glycerol) and heated to 100° C. for 10 minutes, and loaded onto the gel. The gels were electro-phoresed for 1111 volthours at a constant current with an automated power supply (model 3000 xi, Bio-Rad laboratories, Richmond, Calif.), while the apparatus was kept cooled to 4° C. using a thermostatic circulator (LKB Instruments, Bromma, Sweden). The gels were stained with 0.05% Coomassie blue in 40% methanol, 10% acetic acid, or processed for Western blotting.

The Western immunoblotting was conducted according to the method of Towbin et al. using a transfer apparatus (Hoffer). The Western blotting sandwich contained 3.0 mm Whatman filter paper (Whatman Limited, England), nitrocellulose membrane (NCM; Bio-Rad), polyacrylamide gel, and 3.0 mm filter paper in that order. The sandwich was assembled in a tray containing blotting buffer such that no air bubbles were trapped between the sandwich layers. The transfer was performed at 100 volts for four to six hours with a transfer power supply (Hoeffer). The temperature was maintained at 4° C. during the transfer using a thermostatic circulator.

After the transfer, the NCM were cut, using the pre-stained molecular weight marker (Bio-Rad) lane as a guide, and the unbound sites were blocked by incubation in a two percent casein solution for three hours at 4° C. The antibodies were diluted in two percent casein solution and incubated with the membranes in a 150 mm diameter petri dishes or in hybridization bags (BRL) for three hours at room temperature, or for overnight at 4° C. The membranes were washed twice in Tris saline (10 mM Tris, pH 7.4, 150 mM NaCl), with 0.05% Triton X-100, and once in Tris saline for 15 minutes each. The membranes were then incubated with the appropriate alkaline phosphatase labeled antibodyies (Kirkegaard and perry laboratories, Inc.,) diluted to 2.0 µg/ml in casein solution, for one hour at room temperature. The membranes were washed as described earlier, followed by a final wash with 0.9% NaCl. Color development was accomplished with Fast Red TR salt and napthol AS MX phosphate substrates for about 10 minutes, and the reaction was stopped by washing the membrane in distilled water. The diluted sera and enzyme-labeled antibody solutions were stored at −70° C. for reuse.

Cloning of *Ehrlichia risticii* Genomes of Original (25D) and Variant (90-12) Strains:

Fragments of the genomic DNA of *E. risticii* (25D strain) were molecularly cloned in λ-gt11 vectors and a recombinant expressing a complete 50 kD protein antigen gene was identified. Additional cloning of *E. risticii* (90-12 strain) was performed with similar procedures in λ-ZAP (Stratagene, LA Jolla, Calif.) as described below.

Construction of Variant *Ehrlichia risticii* Recombinants:

Restriction enzymes were obtained from Bethesda Research Laboratories (Gaithersburg, Md.), Promega Corporation (Madison, Wis.) and New England Biolabs (Beverly, Mass.). T4 DNA ligase, λ packing mix, λ-ZAP II, pBluescript phagemids, and *E. coli* strain XII-Blue [recA1 endA1 gyrA96 thi hsdR17 ($r_k^-$ $m_k^-$) supE44 relA1 λ$^-$ (lac) {F' proAB lac,$^{-4}$ Z M15, Tn10(tet$^r$)}], were obtained from Stratagene (La Jolla, Calif.).

Restriction Enzyme Digestion of *Ehrlichia risticii* DNA:

Variant *E. risticii* genomic DNA was restriction digested by using Sau3AI (New England Biolabs) site-specific endonuclease in the following manner: Six µl of DNA sample containing 1.0 µg/µl of DNA were mixed with 36 µl of distilled water and 5.0 µl of 1×Sau3A I digestion buffer [100 mM NaCl, 10 mM Tris-HCL, 10 mM $MgCl_2$, (pH 7.3)], supplemented with 0.5 µl (100 µg/ml) bovine serum albumin. The contents of the tube were gently mixed in an eppendorf centrifuge at 10,000 rpm for five seconds. Finally, 2.5 µl of enzyme (10 units/µl) were added and the mixture was again centrifuged at 10,000 rpm for five seconds in an Eppendorf centrifuge, and was kept at 37° C. in a water bath for one hour. The reaction was stopped by the addition of EDTA to a final concentration of 25 mM. A small aliquot was electrophoresed over 1% agarose gel to monitor the digestion. One hundred µl of TE buffer were added to the mixture and the DNA was extracted once with phenol and subsequently washed three times with chloroform:isoamyl alcohol at the ratio of 24:1. The restriction digested DNA was precipitated with ethanol as described above.

Synthesis and Ligation of Adapters to *Ehrlichia risticii* DNA Fragments:

Three different types, (1, 2, and 3) of EcoR I-BamH I conversion adapters were prepared by the annealing of six different kinds of synthetic oligonucleotides, and each of these adapters was ligated separately to the Sau3A I cohesive ends of the variant *E. risticii* DNA fragments.

Synthesis of Duplex Oligonucleotide Conversion Adapters:

Each oligonucleotide used to form the duplex conversion adapters was synthesized by and obtained from Oligos ET Inc. (Wilsonville, Oreg.). One strand (A strand) of each duplex conversion adapter contains the EcoR I cohesive end (AATT) at the 5' terminus to the 10 mer core annealing sequence. Three lengths of the "A strand" (A1, A2, and A3) were synthesized by the addition of single cytosine residues between the 5' end of the core sequence and 3' end of the EcoR I cohesive end. Oligonucleotides complimentary to each length of the "A strand" core annealing sequences (14 mer=B1, 15mer=B2, 16mer=B3) were synthesized with Sau3A I, Mbo I or BamH I cohesive termini (GATC) added to the 5' end of the "B strand". The duplex conversion adapters were formed by separately annealing "A strands" and "B strands" with matching lengths of complimentary core sequences. For this, a 0.5 $A_{260}$ unit of each of the lyophilized oligonucleotide was dissolved in 120 µl of distilled water to obtain a 50 µM solution. Forty µl of each of these complimentary oligonucleotides (A1+B1, A2+B2, A3+B3) were mixed with 10 µl of 10× buffer (250 mM Tris, pH 8.0, 100 mM $MgCl_2$) and 10 µl of distilled water. These mixtures were heated separately to 95° C. and slowly cooled (approximately one hour) to room temperature. This yielded a 20 µM solutions of 1, 2 and 3 types of adapters. At this point the three lengths of each duplex conversion adapters with identical cohesive ends were stored separately at −80° C. for future use.

Ligation of Adapters to *Ehrlichia risticii* DNA Fragments:

Dried ethanol precipitate of Sau3A I *E. risticii* restriction fragments (6 µg) was resuspended in 45 µl of distilled water and was aliquoted in three equal parts. Next, 15 µl of preannealed adapters type 1, 2 and 3 were added to parts 1, 2 and 3 respectively to yield approximately a 10:1 molar ratio of adapter to the insert fragments. To each of these mixtures, 5.0 µl of 10× ligase buffer (500 mM Tris, pH 7.5, 70 mM MgCl$_2$, 10 mM DTT), 0.5 µl of 10 mM ATP, 13 µl of distilled water, and 1.5 µl (6 Weiss units) of T4 DNA ligase (Stratagene, La Jolla, Calif.) were added, mixed well and incubated at 15° C. for six hours. After completion of ligation reaction the contents of the three Eppendorf tubes were mixed together in one tube and were placed in a 70° C. water bath for 10 minutes to heat inactivated the ligase enzyme. Subsequently the tubes were cooled on ice.

Phosphorylation of Adapter Modified Insert DNA and Removal of Excess Adapters:

Adapter modified insert DNA was prepared for ligation into λ-ZAP vector (Stratagene, La Jolla, Calif.) by phosphorylation of adapter 5' ends with T4 polynucleotide kinase (Promega Corporation, Madison, Wis.) and removal of excess adapters by spin column chromatography.

Following heat inactivation and cooling, 150 µl of reaction mixture were added to 20 µl of 10× T4 polynucleotide kinase buffer (500 mM Tris-HCL, pH 7.5, 100 mM MgCl$_2$, 50 mM DTT, 1.0 mM spermidine), 10 µl of 0.1 mM ATP, 1.0 µl of T4 polynucleotide kinase (10 units), and 19 µl of distilled water. The reaction mixture was incubated at 37° C. for 30 minutes and reaction was terminated by single extraction with 1 volume of TE-saturated phenol, followed by three extractions of equal volume of chloroform:isomyl alcohol (24:1). The upper aqueous phase was transferred to a fresh tube and unligated adapters were efficiently removed with spin column chromatography.

The Sephacryl S-400 matrix, spin columns, wash tubes and collection tubes for column chromatography were obtained from Promega Corporation (Madison, Wis.). The chromatography columns were prepared according to the instruction of the Promega technical bulletin (#067). Briefly, Sephacryl S-400 slurry was thoroughly mixed and 1.0 ml slurry was transferred to a spin column. The column tip was placed in the wash tubes and then the whole assembly was placed inside a large centrifuge tube (Falcon #25319) and centrifuged in a swing bucket rotor at 800×g for five minutes. The wash tube with fluid in it was discarded, and a second centrifugation was performed in the same manner to discarded any remaining fluid in the column. The phosphorylated reaction mixture with excess adapters was applied to the top of the gel bed of the prepared column and the column was placed into the collection tube. This whole assembly was then centrifuged in the same manner as described before in the column preparation step. The phosphorylated adapter modified insert DNA present in the eluant of the collection tube was then ethanol precipitated at −20° C. overnight by adding 0.5 volume of 7.5 M ammonium acetate and 2.0 volumes of ethanol. The precipitated DNA was pelleted by centrifugation at 4° C. for 15 minutes and the invisible pellet was washed once with 70% alcohol prior to vacuum drying.

Ligation of Insert DNA to λ-ZAP Arms:

The adapter modified phosphorylated vacuum dried insert DNA pellet was resuspended in 6.0 µl of TE (10 mM Tris, pH 8.0, 0.1 mM EDTA). The optimal vector:insert ratio for efficient ligation was obtained by aliquoting 2.5, 0.5 and 0.1 µl of the *E. risticii* insert DNA into three separate tubes. One μg of EcoR I digested and dephosphorylated λ-ZAP arms (Stratagene) was added to each of the tubes, followed by 1.0 μl of 10× ligase buffer, 0.1 μl of 10 mM ATP, and distilled water to 9.0 μl. Then 1.0 μl of T4 DNA ligase (4 Weiss units, Stratagene) was added and the solution incubated at 15° C. for six hours.

Packaging of Recombinants λ-ZAP DNA:

In vitro packaging of λ-ZAP concatomers was done using the commercially available packaging mix (Gigapack II Gold, Stratagene). Two μl of concatamerized λ-ZAP recombinants were added to a freeze-thaw extract tube. To this, 15 μl of sonicated extract were added and mixed well. After a brief spin to pull the contents to the bottom, tubes were incubated at 22° C. for two hours. This packaging reaction was stopped by adding 500 μl of SM buffer (50 mM Tris, pH 7.5, 100 mM NaCl, 8.0 mM $MgSO_4$, 0.01% gelatin) and 20 μl of chloroform. The reaction mixture was centrifuged at 1500×g for five minutes to pull down the debris. The supernatant was transferred to another tube and 25 μl chloroform was added to it. This recombinant λ-ZAP stock was stored at 4° C. for future use in titrating and screening.

Titration and Amplification of the Recombinants:

Fifty ml of LB (Luria-Bertani) broth supplemented with 0.2% maltose and 10 mM $MgSO_4$ were inoculated with a single colony of XL1-Blue strain of *E. coli*. The cells were grown overnight at 37° C. in a shaking incubator. Then next day the cells were centrifuged at 1000×g for 10 minutes, and resuspended in 25 ml of 10 mM $MgSO_4$ and stored on ice. A 10-fold serial dilution of phage stock (packaging mix), up to $10^{-10}$, was prepared in SM buffer and 10 μl aliquots from each dilution were mixed and incubated separately with 200 μl of above prepared host cells. Each mixture was incubated at 37° C. for 15 minutes to absorb the phage on the surface of the host cells. Seventy ml of NZY top agar (0.75%) were equilibrated at 48° C. in a water bath; then 350 μl of 250 mg/ml 5-bromo-4-chloro-3-indoyl-β-D-galactopyranoside (X-gal) and 105 μl of 0.5M isopropyl-β-D-thiogalactoside (IPTG) were added to it. Seven ml of this molten top agar were mixed separately with each dilution of phage-bacteria mixture and poured immediately onto a 100 mm petri dish. The plates were incubated at 37° C. for 6 hours and stored at 4° C. overnight for color development. The next day, the blue and clear plaques were counted to determine the titer and cloning efficiency of the packaged λ-ZAP.

To obtain a high titer library for storage, in vitro packaged recombinants were amplified by plating approximately 50,000 plate forming units (pfu) and incubating at 37° C. for about 6 hours. When the plaques attained the size of about 0.5 mm, 10 ml of SM buffer were added to the plate and incubated overnight while shaking at 4° C. The suspension containing phage was extracted once with chloroform and stored in the presence of 0.3% chloroform.

Immunoscreening of Recombinants for Expression of Variant *Ehrlichia risticii* Antigens:

The variant recombinant clones were screened for expression of variant *E. risticii* antigens using rabbit and mouse antisera against the variant *E. risticii* strain. Before use, the rabbit antisera was exhaustively absorbed against *E. coli* and λ-ZAP protein components.

Production of Antiserum Against Variant Strain:

Hyperimmune sera to the variant strain of *E. risticii* were produced in rabbits. The first injection contained 80 μg and 320 μg of the purified organism, emulsified with Freund's adjuvant, administered by interdermal and intramascular routes, respectively. A second injection, administered two weeks later by the intramascular route, contained 200 μg of the purified *E. risticii* emulsified in Freund's incomplete adjuvant. At four and seven weeks following the first injection rabbits were again injected intramuscularly with 200 μg of the organism only. One week after the final injection, sera were collected and pooled. Antisera from mice infected or immunized with *E. risticii* were obtained as according to known procedures.

Absorption of Variant *Ehrlichia risticii* Antiserum:

Variant *E. risticii* antisera were exhaustively absorbed with the lysates of *E. coli* strain XL1-Blue and λ-ZAP phage to remove any non-specific antibodies. An one liter culture of XL1-Blue transformed with pBluescript SK-phagemids (Stratagene) was grown in LB medium to an $OD_{600}$ of 0.5 at 37° C., and IPTG was added to 10 mM final concentration. The cells were harvested by centrifugation at 11,000×g for 10 minutes and the cell pellet was resuspended in 20 ml of 10 mM Tris, pH 7.5, 1.0 mM phenylmethylsulfonyl fluoride (Sigma). About 15 ml of cell suspension were subjected to four 30 second cycles of sonication at 4° C. Next, Triton X-100 was added to 0.05% and the homogenate was incubated for 30 minutes on ice and then diluted in 30 ml Tris saline (10 mM Tris, pH 7.4, 150 mM NaCl), and stored at −70° C. This preparation of bacterial cell lysate was designated as sonic lysate. To the remaining 5.0 ml of original cell suspension, Laemmli sample buffer (62.5 mM Tris, pH 6.8, 2% SDS, 5% 2-mercaptoethanol, 10% glycerol) was added to 1×, heated to 100° C. for five minutes, and diluted with 10 ml of Tris saline and stored at −70° C. This preparation of bacterial cell lysate was designated as SDS lysate.

A large scale preparation of λ-ZAP phage particles was produced according to Maniatis. One liter of X11-Blue cells was grown up to the $OD_{600}$=0.5, in LB media supplemented with 0.2% maltose and 10 mM $MgSO_4$. The culture was inoculated with $10^{10}$ pfu of phage particles and incubated at 37° C. for an additional five to six hours, until the visible lysing of the bacterial cells was prominent as indicated by presence of cell debris. The lysed culture was further incubated for 10 minutes in presence of 20 ml of chloroform. Pancreatic DNAase-I and RNAase (Sigma), were added to this lysed culture to a final concentration of 1.0 μg/ml and a further incubation was performed for an additional 30 minutes at room temperature. To disperse the phage particles from the bacterial debris, 58.4 gm of solid NaCl were added and the lysate was incubated at 4° C. overnight. The next day the bacterial debris was removed from this lysate by centrifugation at 11,000×g for 10 minutes and 100 gm of solid polyethylene glycol (PEG 8,000) were mixed into the supernatant. The mixture was incubated on ice water for 1 hour and the precipitated phage particles were recovered by centrifugation at 11,000×g for 10 minutes. The supernatant was discarded and the phage pellet was resuspended in 20 ml of Tris saline and added to the sonic lysate obtained earlier.

In separate polyethylene bags, ten 137 mm nitrocellulose circles (NCM, Schleicher & Schuell, Inc., Keene, N.H.) were incubated with sonic lysate and another five membranes were incubated with SDS lysate for two hours at room temperature on a shaker. The membranes were then washed five times with Tris saline for 15 minutes each and incubated overnight with casein solution (2% casein in 10 mM Tris, pH 7.5, 120 mM NaCl) at 4° C. Five ml of rabbit anti- E. risticii serum were diluted in 100 ml of casein solution and placed in a tray. Two NCM adsorbed with sonic lysate and one NCM adsorbed with SDS lysate were placed in the tray and incubated for two hours. The membranes were taken out, replaced with new sets of membranes and incubated as before. The process was repeated with all the membranes. The absorbed serum was aliquoted and stored at −70° C.

Immunoscreening the Recombinants of Variant Strain:

Screening the λ-ZAP recombinants for expression of *E. risticii* antigens was done according to known procedures. *E. coli* strain XL1-Blue was used as a host cell to plate the library. A liquid culture was started from a single colony and grown overnight with vigorous shaking at 30° C. in LB media supplemented with 0.2% maltose and 10 mM $MgSO_4$. The cells were centrifuged at 1000×g for 10 minutes then gently resuspended in 0.5 volumes of 10 mM $MgSO_4$. About 700 to 1000 pfu of the packaged λ-ZAP were mixed with 1.2 ml of above prepared XL1-Blue cells and incubated at 37° C. for 18 minutes. Twenty one ml of molten NZY top agar (0.8%), prewarmed to 42° C. were then added, mixed, and poured onto a 150 mm plate containing 1.5% NZY bottom agar and the agar was allowed to solidify at room temperature for 15 minutes. The plates were incubated at 37° C. for four hours, until the plaques were about one mm in size. Next, a 137 mm colony/plaque screen membrane (NEN® Research products, Boston, Mass.) was saturated with IPTG solution (10 mg/ml) and blotted dry on a filter paper. This membrane was carefully placed on the top agar and incubation was continued at 37° C. for another three hours. The membrane was pierced asymmetrically at three places with an 18 gauze needle, peeled from the agar, and washed three times with Tris saline to remove the debris and bacteria. The plates were then stored at 4° C. and the washed NEN membranes were blocked with casein solution at 4° C. overnight. The next day, membranes were incubated in a 1:100 dilution of the absorbed *E. risticii* antisera for two hours at room temperature and washed twice in Tris saline with 0.05% Triton X-100, and once in Tris saline for 15 minutes each. The antisera treated membranes were incubated either with 2.0 μg/ml of alkaline phosphatase labeled goat anti-rabbit IgG or mouse anti-rabbit IgG (Kirkegaard and Perry) for one hour at room temperature. The membranes were consecutively washed three times in the same way described earlier in this procedure, followed by a final wash with 0.9% NaCl. Finally the membranes were treated with Fast Red and naphthol substrate solution for about 10 minutes and the reaction was stopped by washing the membrane in distilled water.

The pink immunoreactive spots corresponding to the recombinants expressing *E. risticii* antigens were aligned with the help of the needle marks and those positive plaques were picked up from the plates with the aid of a Pasteur pipette. The agar plugs containing the recombinant plaques were dispensed separately into 500 μl of SM buffer and the phage were allowed to diffuse out by vortexing and incubating vials at 4° C. for two hours. Twenty μl of chloroform were also added separately in each vial before long term storage. Plaque purification of the recombinants was accomplished by two additional rounds of immunoscreening as above.

Identification of Recombinant Antigens of Variant Strain:

The identity of the recombinant antigen expressed in the clones of the λ-ZAP library was established by preparing monospecific antigen-selected antibodies and reacting this with the nitrocellulose strips containing electrophoretically separated *E. risticii* antigens.

Production of Recombinant Clone Specific Antibody:

The plaque purified λ-ZAP recombinants ($10^5$ pfu) were mixed separately with 1.2 ml of pre-prepared $MgSO_4$ treated XL1-Blue cells and incubated at 37° C. for 18 minutes to absorb the phage on surface of bacteria. Each phage bacteria mixture was plated on a 150 mm petri dish as described above. After the plaques had attained the size of 1.0 mm, a 137 mm NCM saturated in IPTG solution (10 mg/ml) was overlaid on the top agar of the plate and incubated at 37° C. for four hours. The NCM was reversed and incubation was continued for an additional three hours. After washing and blocking the unbound sites, as described above, the NCMs were incubated with the 1:100 dilution of antisera at 4° C. overnight. The membranes were washed once with Tris saline, twice in Tris saline with 0.05% Triton X-100, and once in Tris saline for 15 minutes each. The membranes were then placed separately in polyethylene hybridization bags (BRL) and 10 ml of glycine buffer (0.2 M glycine, pH 2.8, 150 mM NaCl) were added to each bag. The bags were heat sealed and incubated at room temperature for one hour to elute the antibodies. The eluted antibodies were neutralized to pH 7.0 with 500 µl of 1.32 M Tris base and stored at −70° C. A preparation made from the non recombinant λ-ZAP was processed in same way as the negative control.

Identification of the Recombinant Antigens:

The recombinant clone-specific antibodies were diluted with an equal volume of casein solution. These antibodies were incubated overnight at 4° C. with a strip of NCM on which electrophoretically separated E. risticii proteins had been blotted. Next, the strips were treated with alkaline phosphatase labeled anti-rabbit IgG and substrates. The strips were now aligned with an adjacent strip which had been reacted with polyclonal *E. risticii* antisera and the identity of the antigen encoded by the recombinant was ascertained.

Antigenic Analysis of Standard and Variant Strains:

Western immunoblotting was performed on both standard and variant *E. risticii* strains with their homologous and heterologus mouse antisera by the procedure described above. Antigenic analysis of the component antigens of these two different strains of *E. risticii* was also performed by Western blotting with clone specific antibodies of 85 kD, 55 kD, 51 kD and 28 kD proteins of the variant strain and the 50 kD of the standard strain. In order to perform this renograffin purified *E. risticii* of standard and variant strains were gel electrophoresed in several lanes in alternate combination. After blotting the NCM strips were cut in such a way that each strip contained the antigens of both the standard and variant strains. These strips were then treated separately with a clone specific antibody to determine the antigenic difference and similarities between the strains. The techniques which were followed here were described above.

Construction of DNA Probe and DNA Hybridization:

The random primer labeling technique was used to incorporate the radioactive $^{32}P$ in *E. risticii* insert DNA of several recombinants. The labeled probes generated in this manner were used in Southern hybridization of the restricted *E. risticii* genome of standard and variant strains.

Probe DNA:

The probe DNAs were prepared by using two different techniques. One of the techniques involved restriction digestion of the recombinant phagemids, agarose gel electrophoretic separation of the insert DNA, and elution of the insert DNA band from the gel. In this process, after gel electrophoresis, the agar piece containing the specific DNA band was visualized on an ultraviolet light transilluminator (Hoeffer, San Francisco, Calif.) and separated out from the gel by using a razor blade. The DNA was extracted from the agarose gel piece by using silica beads (GenecleanII, Bio101, La Jolla, Calif.), following the manufacturer's suggested protocol. Briefly the gel piece was weighed and about three volumes of 6.0 M sodium iodide were added and incubated at 55° C. until the agarose completely dissolved. To this, 5.0 $\mu$l of silica beads (Glassmilk, Bio101) were added and the emulsion incubated at room temperature for five minutes while occasionally mixing the silica beads with the dissolved agarose by tapping the tube. The silica beads were separated out from the solution by quick centrifugation in a table top microcentrifuge and washed with 10 mM Tris, pH 7.5, 100 mM NaCl, 1.0 mM EDTA, 50% ethanol (New Wash; Bio101). The process was repeated for two more times and finally the DNA bound with the silica beads was eluted by resuspending the beads with 10 $\mu$l of distilled water and incubating at 55° C. for five minutes.

The other technique involved PCR amplification of a segment of DNA directly from the genomic DNA of *E. risticii*. Specific sequences obtained from the cloned *E. risticii* recombinants were used to select the proper primer pair for each amplification. Typically a 100 $\mu$l PCR reaction mixture consisted of 10 $\mu$l of 10× reaction buffer (0.5M KCl, 0.1M Tris, pH 8.3, 15 mM $MgCl_2$ and 0.1% gelatin), 16 $\mu$l of deoxyribonucleotide triphosphates (160 nmoles each), 4.0 $\mu$l of primers (0.1 nmole each), 0.5 $\mu$l of Taq polymerase (5 units/$\mu$l), 10 $\mu$l of *E. risticii* genomic DNA (1 $\mu$g/ml) and 59.5 $\mu$l of distilled water. The amplification was performed using a DNA Thermal Cycler (Perkin Elmer Cetus, Norwalk, Conn.). The initial template denaturation step proceeded for 1.5 minutes at 95° C. Then a typical cycle profile consisted of annealing for two minutes at 52° C., extension for three minutes at 72° C. and denaturation for one minute at 94° C. A total of 60 cycles were performed. At the end of the 60th cycle the heat denaturation step was omitted and the extension step was extended by an additional seven minutes. Following the termination of the amplification cycle, the sample was allowed to return to at 4° C. temperature and held there. The specificity of the PCR amplified DNA was further confirmed by gel electrophoresis and the DNA was purified by Geneclean II, following the procedure described above.

Labeling of Probe DNA:

The random primer labeling was done by Prime a Gene® Labeling System (Promega Corporation). Twenty ng of DNA were diluted in 25 $\mu$l of distilled water and boiled at 100° C. for two minutes. The solution was immediately chilled on ice. With the tube held on ice, 10 $\mu$l of 5× labeling buffer (250 mM Tris-HCl, pH 8.0, 25 mM $MgCl_{2,\ 10}$ mM DTT, 1 M HEPES, pH 6.6, and 26 $A_{260}$ units/ml random hexadeoxyribonucleotide primers), 2.0 $\mu$l mixture of nonlabeled deoxyribonucleotides (0.5 mM each of dATP, dGTP, and dTTP), 2.0 $\mu$l nuclease free BSA (400 $\mu$g/ml), 5.0 $\mu$l of $\alpha^{32}P$ (50 $\mu$Ci) dCTP and 5.0 units of DNA polymerase I Klenow fragment were added. The mixture was incubated overnight at room temperature and finally the labeling reaction was terminated by heating at 100° C. for two minutes. The unincorporated nucleotides from the reaction mixture was removed by using the Push column (Stratagene) and the mixture was stored at −20° C. for future use in a Southern hybridization cocktail.

The amount of incorporated radioactivity and the specific activity was measured by TCA precipitation (10% trichloroacetic acid and 1% sodium pyrophosphate). Specific activities in the range of $10^9$ counts/minutes (CPM) per $\mu$g of DNA were obtained by the random primer labeling method.

Southern Blot Hybridization:

The gel containing the DNA samples was acid-depurinated with 0.25M HCl for 15 minutes, denatured with 0.4 M NaOH-0.6 M NaCl for 30 minutes, and neutralized with 1.5 M NaCl/0.5 M Tris, pH 7.5, for 30 minutes. In preparing for capillary transfer, two layers of 3.0 mm Whatman filter paper were spread on the Plexiglas support of the blotting apparatus (BRL), and placed in a buffer tray filled with 10×SSC and a pipette was rolled over them to remove air bubbles. The gel was carefully inverted and placed on the filter paper, and again the pipette was rolled over to remove any trapped air bubbles. This whole assembly was then covered with Saran-wrap and the plastic was cut exactly to the outline of the gel. The Saran-wrap used to avoid direct contact between the wick and the stacking paper towels, and it also helped to prevent the unnecessary evaporation of the buffer. Genescreen Plus Membranes (NEN products) were presoaked in distilled water for one minute and in 10×SSC for 15 minutes. The membranes were placed on the gels and air bubbles were removed by rolling the pipette as before. Three sheets of 3.0 mm Whatman filter paper were soaked in 10×SSC and placed on the blotting membrane and a 5" stack of paper towels were laid on the top of these filter papers. The DNAs from the gel were capillary transferred to the Genescreen Membrane overnight. The next day, the membrane was carefully removed from the gel and was treated with 0.4 N NaOH for one minute and 2.0×SSC/0.2 M Tris, pH 7.5 for five minutes. Finally the membrane was placed on a 3.0 mm Whatman filter paper and DNAs were permanently bound with the membrane by a 30 seconds exposure in an Ultra Violet Crosslinker from Stratagene.

The membrane blot was prehybridized in a polypropylene bag for 1.5 hours at 45° C. in a prehybridization solution consisting of 8 ml of Hybrisol I (Oncor, Gaithersburg, Md.) and 2.0 ml of Hybrisol II (Oncor) solution. The probe DNA was denatured by boiling for two minutes and added to a final concentration of $3 \times 10^6$ counts/minutes (CPM) per ml of prehybridization solution. The hybridization was continued at 45° C. for 18 hours and then membrane blot was carefully removed from the bag. The membrane was washed twice with 1.0×SSC, 0.1% SDS at room temperature for 20 minutes each and once with 0.1×SSC, 0.1% SDS at 60° C. for one hour. The wet membrane was sealed in a hybridization bag and exposed to X-omat film (Kodak, Rochester, N.Y.) at −70° C. for varying time intervals. The multiple rehybridization of the same membrane blot was also accomplished by stripping the probe from the membrane. To do this the membrane was boiled for 30 minutes in a solution of 10 mM Tris-HCl, pH 8.0, 1 mM EDTA and 1% SDS. The DNA molecular weights in a Southern blot were determined by hybridizing the 1 kilobase DNA ladder (BRL) run in the adjacent lane of the gel with the $^{32}P$ labeled probe of one kilobase DNA ladder.

Recombinant DNA Procedures and Sequencing:

The variant E risticii antigens were expressed by several λ-ZAP recombinants. The in vivo excision of those λ-ZAP recombinants yielded pBluescript SK(−) phagemid clones. The specific clones obtained from the recombinants expressing 85 kD antigen were further subcloned to obtain the complete nucleotide sequence of the 85 kD gene. The λ-gt11 recombinant of 50 kD antigen gene was cloned in pBluescript SK(+) phagemid.

In vivo Excision of pBluescript SK(−) Phagemid:

In vivo excision of the pBluescript SK(−) phagemids from the λ-ZAP recombinant phages was done according to the procedures of the manufacturer (Stratagene). The ExAssist™ helper phage and Solr™ bacterial strain [e14$^-$(mcrA), Δ(mcrCB-hsdSMR-mrr) 171, sbcC, recB, recJ, umuC::Tn5 (kan$^r$), uvrC, lac, gyrA96, reiA1, thi-1, endA1, $\lambda^R$, {F' proAB, lac,$^4$ ZM15} Su$^-$ (non-suppressing)] were also obtained from the Stratagene. After being plate purified three times, a single recombinant plaque was lifted from the agar plate and transferred into a sterile microfuge tube containing 500 μl of SM buffer and 20 μl of chloroform. The tube was vortexed and incubated at room temperature for two hours to diffuse the phage from the agar block into SM buffer. The titer of this phage stock was $10^6$ pfu/ml. In a 50 ml tube, 200 μl of 0.5 $OD_{600}$ XL1-Blue cells were mixed with 100 μl of phage stock and 1.0 μl of ExAssist helper phage and incubated at 37° C. for 15 minutes. Next, 3.0 ml of 2×YT media were added and incubation was continued for another 2.5 hours at 37° C. in a shaker incubator. In this incubation period, a co-infection of the recombinant λ-ZAP phagemid and the ExAssist helper phage proceeded in the same XL1-Blue cells. As a final result the newly created recombinant pBluescript SK(−) phagemids were packed inside of the ExAssist helper phage and released from the bacterial cells. Once the phagemids were secreted, the remaining XL 1-Blue cells were removed from the mixture by heating the tube at 70° C. for 20 minutes. The heat treatment killed all the bacterial cells while the phagemid remained resistant to the heat treatment. The heat inactivated mixture was then centrifuged at 4,000×g for 10 minutes to pellet the cellular derbies and the supernatant was stored at 4° C.

To rescue the phagemid, 10 μl and 0.1 μl volumes of packaged phagemid stock from above were mixed with 200 μl of 0.1 $OD_{600}$ Solr cells (*E. coli*) separately and incubated at 37° C. for 15 minutes. About 10 to 50 μl volumes were plated onto LB plates containing 100 μg/ml of ampicillin, and incubated at 37° C. overnight. Since the Solr cells were resistant to λ-ZAP recombinant, the colonies which appeared the next day on the plates contained the pBluscript SK(−) double stranded phagemid with the cloned DNA insert. The bacteria infected with helper phage alone could not grow because they did not contain the ampicillin resistant gene.

Extraction and Purification of Phagemid DNA:

Phagemid template DNA was prepared for sequencing and other recombinant work by a known method. The cell containing the phagemids were grown in lightly capped 15 ml plastic screw cap tubes with 5.0 ml of LB broth containing 100 μg/ml ampicillin. The cultures were aerated by mixing them in a shaker incubator at 37° C. overnight. The following day 1.5 ml of the cultures were transferred to 1.5 ml microfuge tubes and centrifuged for two minutes. The supernatant was removed, an additional 1.5 ml of culture was added, and the tubes were again centrifuged for two minutes. The supernatant was removed as completely as possible and cellular pellet was resuspended in 100 μl of an ice cold solution of glucose/Tris/EDTA buffer (50 mM glucose, 25 mM Tris-HCl, pH 8.0 and 10 mM EDTA). The tubes were incubated at room temperature for five minutes. Cells were lysed by the addition of 200 μl NaOH/SDS solution (0.2 N NaOH, 1% SDS), gentle mixing, and incubation at room temperature for 10 minutes. Neutralization of NaOH and precipitation of SDS and chromosomal DNA was accomplished by the addition of 150 μl of 3.0M potassium acetate, pH 4.8 with gentle mixing for at least 30 seconds. The contents were centrifuged for five minutes at 4° C. and supernatants were transferred to fresh tubes, centrifuged another five minutes, and again transferred to new tubes, avoiding the carryover of any precipitate. To these supernatants, 1.0 ml of ice-cold absolute ethanol was added and the nucleic acids were allowed to precipitate at 20° C. for 30 minutes. The nucleic acid precipitates were collected by centrifugation at 4° C. for five minutes, washed with 70% ethanol, and the pellets were dried. The nucleic acids were resuspended in 20 μl of TE buffer and the RNA was digested by the addition of 1.0 μg of RNAase-A at 37° C. for 30 minutes. About 2.0 μl of this mini preparation DNA were used for restriction digestion analysis.

Subcloning of 50 kD Recombinant of 25D Strain:

The insert of 50 kD antigen gene of 25D strain identified from the λ-gt11 library, was re-cloned in pBluescript SK(+) for restriction mapping. This insert-plasmid of recombinant pBluescript SK(+) was restriction digested and the fragments were subcloned in pBluescript SK(−) vector for further analysis and sequencing purposes. The internal segment of the insert was also PCR amplified and subcloned for the same interest.

The specific restriction digestion was obtained by the Hind III enzyme. For this, 1.0 μg of pBluescript SK(−) phagemid (Stratagene) was digested with Hind III, and the completeness of digestion was ascertained by agarose gel electrophpresis. The DNA was then extracted with phenol:chloroform and resuspended in 1.0× calf intestinal alkaline phosphatase buffer (Promega, 50 mM Tris, pH 9.0, 10 mM $MgCl_2$, 1.0 mM $ZnCl_2$, 10 mM spermidine). Dephosphorylation of the 5' $PO_4$ groups was accomplished by digestion with 2.0 units of calf intestinal alkaline phosphatase (Promega). The enzyme was removed from the reaction mixture by phenol-chloroform extraction and DNA was ethanol precipitated as before, with additional washing in 70% ethanol to remove the pyrophosphate ions. Finally the DNA pellet was resuspended in 10 μl of TE buffer. About 2.0 μl of mini preparation DNA (1.0 μg) were mixed with 4.0 μl of the appropriate 10× digestion assay buffer (Promega) and Hind III restriction endonuclease (Promega) at a final concentration of 1.5 unit/μg DNA. After complete digestion for one hour at 37° C., 8.0 μl of the gel loading buffer (Appendix 5) containing a marker dye, were added to the tube. The reaction mixture was electrophoresed on 1% agarose gel by a submerged horizontal gel electrophoresis apparatus (BRL). Marker DNA (1 kilobase ladder, BRL) was electrophoresed simultaneously to monitor and compare the run of the DNA samples. Upon completion of the electrophoretic run, the migration pattern of the DNA bands was viewed with a 302 nanometer ultraviolet transilluminator (Spectoline, Model T. P.-302). The upper band consisted of plasmid DNA and the lower two bands consisted of insert DNA of the 50 kD antigen gene. The insert bands, as ascertained by electrophoretic migration, were cut out from the gel and processed for purification of DNA by Geneclean II (Bio101) silica matrix.

One μl of the prepared vector (0.1 μg) was mixed with two different 10 fold dilutions of insert DNA to obtain a nearly optimal ratio (2:1, insert:vector). To each of these reaction mixtures, 1.0 μl of 10 mM ATP and, 1.0 μl of 10×ligase buffer (Promega, 1.0× is 3.0 mM Tris, pH 7.8, 10 mM $MgCl_2$, 10 mM DTT and 5.0 mM ATP), were added. Each was brought to a final volume of 9.5 μl with distilled water. The DNA ends were ligated with two units of T4 DNA ligase (Promega) and the solution were incubated overnight at 18° C.

The *E. coli* XL1-blue competent cells were transformed with the ligated DNA by electro-transformation, using the Bio-Rad Gene Pulser apparatus. The competent cells were produced according the procedure described in Pulse controller instruction manual (Catalog #165-2098) of Bio-Rad. One liter of LB broth was inoculated with 1/100 volume of a fresh overnight culture and grown at 37° C. with vigorous shaking to an $OD_{600}$ of 0.6. The rapidly growing culture was cooled on ice for 30 minutes and the cells were harvested by centrifugation at 4,000×g for 15 minutes in 4° C. The pellet was washed two times with one liter of ice cold distilled water and finally the pellet was resuspended in 3.0 ml of 10% glycerol. The prepared cells were aliquoted and stored at −70° C. Just before the electro-transformation, the frozen cells were thawed on ice and 40 μl of the cell suspension were added to 2.0 μl of ligation mix. After one minute incubation on ice, the mixture was transferred into a cold 0.2 cm electroporation cuvette and pulsed with a time constant of four to five milli seconds with a field strength of 12.5 kV/cm. Immediately 1.0 ml of prewarmed SOC medium (2% Bacto tryptone, 0.5% Bacto yeast extract, 10 mM NaCl, 2.5 mM KCl, 10 mM $MgCl_2$, 10 mM $MgSO_4$, 20 mM glucose) was added to the mixture and then incubated at 37° C. for one hour in an orbital shaker. About 20 μl aliquots were plated on LB plates containing 100 μg/ml ampicillin, X-gal, and IPTG. After overnight incubation at 37° C., single white recombinant colonies were picked up, grown in 5.0 ml of LB medium with 100 μg/ml of ampicillin and stored at −70° C. in 15% glycerol.

Due to the presence of the direct repeats, the central segment of the 50 kD antigen gene was PCR amplified and subcloned separately. This strategy was followed to avoid the binding of sequencing primer at more than one place in the entire length of the gene. To do this, 1.0 pg of 50 kD recombinant plasmid DNA was PCR amplified following the standard reaction parameter described above. The amplified product was ascertained by electrophoretic migration and the product was cloned in pCR™II vector (Invitrogen). Briefly 1.0 μl of PCR amplified product was mixed with 5.0 μl of distilled water, 1.0 μl of 10×ligation buffer, 2.0 μl pCR™II vector and 4 units of T4 DNA ligase. The mixture was incubated at 12° C. overnight. *E. coli* One Shot™ competent cells (Invitrogen) were transformed with the ligated DNA according to the manufacturer's procedure. Fifty μl of competent cells were thawed on ice and 2.0 μl of 0.5 β-mercaptoethanol and 1.0 μl of ligation mix were added to it. After incubation on ice for 30 minutes, the cells were heat shocked by placing in a 42° C. water bath for 30 seconds and immediately transferred to ice for two minutes. The transformed cells were re-vitalized by adding 450 μl of pre warmed SOC media and shaking in a incubator at 37° C. for one hour. About 100 μl aliquots were plated on LB plates containing 50 μg/ml ampicillin and X-gal. After incubation at 37° C. overnight, single white colonies were picked up, grown in 5.0 ml of LB medium with 100 μg/ml of ampicillin and stored at −70° C. in 15% glycerol.

Subcloning of 85 kD Recombinants of 90-12 Strain:

Two different recombinant phagemid clones expressing the 85 kD antigen gene were identified from λ-ZAP library of 90-12 strain. After in vivo excision the recombinant phagemids DNA were extracted and the size of the inserts from these two specific clones were ascertained by Hind III and Sau3A I restriction enzyme digestion. Several insert fragments from Sau3A I restriction digestion products were further subcloned in pBluescript SK(−) vector for sequencing purposes. The two clones which expressed the 85 kD antigen gene did not cover the 5' end of this gene. To clone the 5' end and obtain the complete sequence, the upstream 5' region of the 85 kD gene was PCR amplified directly from the genomic DNA of 90-12 strain. The specific primers used for this purpose were selected from the 5' upstream and middle of the 50 kD gene sequence of 25D strain and the PCR product was cloned in pCR™II vector. This was accomplished according to the procedure described above.

DNA Sequencing:

The double stranded DNA was sequenced according to the Sangers dideoxy chain termination method using the Sequenase® Version 2.0 kit (United States Biochemical, Cleveland, Ohio). This method involved the in vitro synthesis of a DNA strand from a single stranded DNA template using a DNA polymerase. Synthesis was initiated at only one site where an oligonucleotide primer annealed to the template. The synthesis chain reaction was terminated by the incorporation of a nucleotide analogue that would not support continued DNA elongation (hence the name chain termination). The chain terminating nucleotide analogues were the 2', 3' dideoxynucleoside 5'-triphosphates (dd NTPs) which lacked the 3'-OH group necessary for DNA chain elongation. When proper mixtures of dNTPs and one of the four ddNTPs were used, enzyme catalyzed polymerization was terminated in a fraction of the chain population at each site where the ddNTPs were incorporated. Four separate reactions, each with different ddNTPs, gave complete sequence information. A radiolabeled nucleotide was incorporated during the synthesis, so that the labeled chain of various lengths were visualized by autoradiography, after separation by high resolution electrophoresis.

The polymerase 'Sequenase®' a modification of bacteriophage T7 DNA polymerase (United States Biochemical), was used for sequencing. The unique properties of Sequenase® are high processivity, low 3' to 5' exonuclease activity, and the efficient use of nucleotide analogues. These characteristics produce radioactive bands of more uniform intensity and less background radioactivity than those obtained when using a large fragment of E. coli DNA polymerase I or reverse transcriptase. Synthetic oligonucleotides (Oligos ETC Inc), specific for DNA clones at different restriction sites, were used as sequencing primers. Template DNA, purified by minipreparation was first annealed to the sequencing primer. Then DNA synthesis was carried out in two steps. The first step labeling and the second step resulted in the accurate termination of DNA synthesis using the dideoxynucleotides. In the first step, the primer was extended using a limiting concentration of deoxynucleoside triphosphates, including the radiolabeled dATP. In this step, virtually complete incorporation of labeled nucleotide occurred into DNA chains which were distributed randomly in length, from several to hundreds of nucleotides. In the second step, the concentration of all the deoxynucleoside triphosphates were increased and a dideoxynucleoside triphosphate was added. Processive DNA synthesis occurred until all growing chains were terminated by a dideoxynucleotide. At this stage, the chains were extended on an average of several dozen nucleotides. The reaction was ultimately terminated by the addition of EDTA and formamide. This was followed by denaturation electrophoresis and autoradiography.

Annealing of Template and Primer:

The miniprep, RNA-free double stranded plasmid DNA was first denatured by the alkaline denaturation method prior to annealing the sequencing primer with the target sequence. To do so, 8.0 µl of miniprep DNA was mixed with 9.0 µl of distilled water, 2.0 µl of 2M NaOH, 1.0 µl of 4.0 mM EDTA, and the mixture was incubated at 37° C. for 30 minutes in a water bath. The mixture was neutralized by adding 0.1 volume of 3 M sodium acetate (pH 5.0) and the DNA was precipitated with three volumes of ethanol at −70° C. for 15 minutes. After washing the pelleted DNA with 70% ethanol, it was redissolved in 7.0 µl of distilled water and 2.0 µl of Sequenase® (United State Biochemicals) reaction buffer, and 1.0 µl (3.0 ng) of the appropriate primer was added. The mixture was heated to 65° C. for two minutes and then slowly cooled down to ambient temperature over a period of 30 minutes. Once the temperature was below 35° C., annealing was complete.

Labeling Reaction:

To label the DNA, a labeling mix, (supplied with the kit) was diluted five fold with distilled water (2.0 µl of labeling mix and 8.0 µl of distilled water) in a sterile Eppendorf tube. One µl of Sequenase was diluted with 7.0 µl of ice cold TE buffer in another sterile Eppendorf tube. To the Eppendorf tube containing 10 µl of annealed template-primer, the following were added sequentially: 1.0 µl of 0.1M dithiothreitol, 3.0 µl of diluted labeling mix, 0.5 µl of DATP (10/µci/µl), and 2.0 µl of diluted Sequenase®. After mixing, the tube contents were incubated for five minutes at room temperature.

Termination Reaction:

Four Eppendorf tubes were labeled A, C, G and T. Two µl of each termination mix (supplied in Sequenase® kit) were placed in the respective tubes. The termination tubes were prewarmed to 37° C. for one minute in a water bath. When the labeling reaction was completed, 3.5 µl of labeling mixture was transferred into each termination tube. The contents were mixed and incubated at 37° C. for 5 minutes in a water bath. Following incubation, 4.0 µl of stop solution (95% formamide, 20 mM EDTA, 0.05% bromophenol blue, 0.05% xylene cyanol) were added to each tube to stop the reaction. The contents of the tubes were mixed thoroughly and stored at −20° C. until ready to load on the sequencing gel for electrophoresis.

Sequencing Gel Electrophoresis:

A Baserunner 200 Sequencing apparatus (Eastman Kodak Company, Rochester, N.Y.) was used for electrophoresis of the sequencing gel. To cast the 6% polyacrylamide gel, two clean, Sigmacote (Sigma) treated glass plates were assembled using a vinyl side spacer (0.4 mm) and 50 ml gel mixture (28.35 g urea, 10.5 ml 40% bisacrylamide, 6.75 ml 10×TBE, 26 ml of distilled water, 675 µl of 10% ammonium persulfate, 18 µl of TEMED) was poured into the gel mold. The flat edge of the shark-tooth comb (0.4 mm) was inserted between the plates to a minimum depth of 2.0 to 3.0 mm. After overnight polymerization, the comb was removed and then placed again with it's teeth facing the gel sandwich.

Then each buffer chamber of the apparatus was filled with approximately 500 ml of electrophoresis buffer (1×TBE). The gel was pre-electrophoresed for 30 minutes at a constant power of 60 watts, before loading the samples. The DNA samples from the dideoxy sequencing reactions were heated to 80° C. for two minutes and then transferred to ice immediately prior to loading onto gel. The wells of the gel were rinsed out using a 10 ml syringe, attached with a 18 gauge needle to remove urea that had diffused out from the gel. Three µl of sample from each tube marked A, C, G and T were loaded onto the gel in the wells in that order (left to right). After loading, the sequencing gel was electrophoresed at 55 watts to generate enough heat to keep the DNA denatured. The surface temperature of the glass plate was maintained at least 50° C. during electrophoresis. About three hours later, when the lower marker dye reached the bottom of the gel, another 3.0 µl of each sample were loaded into new wells in the same order and the gel was electrophoresed at 52 watts for another two hours. After the samples were run, the upper glass plates were disassembled carefully and the gel was soaked with 10% acetic acid and 12% ethanol until the xylene cyanol disappeared. This was done to ensure that all the urea was removed from the gel. The gel was removed from the lower glass plate onto a support of 3.0 mm Whatman paper and placed in a gel dryer for two hours.

The dried gel was placed in a metal cassette which had a spring-loaded lid to hold the gel and the film in a close contact. The gel was exposed to X-Omat™ (Eastman Kodak Company) 18×43 cm film in direct contact with the gel. After overnight exposure, the film was removed and developed by using an automatic X-ray developer.

Analysis of DNA and Deduced Amino Acid Sequences:

The DNA sequence analysis was done by IBI Pustell software (IBI Limited, Cambridge, England). Using the program "Protein Coding Region Locator" the open reding frame (ORF) of DNA sequences were acertained. This program combines several method for locating potential coding regions in a DNA sequence. The first method searches both strands of the DNA sequence, looking for regions between user-set start and stop codons (ORF). In prokaryotes it uses ATG for starts and termination codons for stops, and searches for all possible six reading frames. The second method uses a statistical search (Fickett's Testcode) which looks for regions of DNA with biased usage of codons. This measurement is made over a window of bases which Fickett has shown must be at least 200 for good results. The probability can be set (0.29, 0.40, 0.77 or 0.92) to confirm that the region located is a real coding region. The high value of 0.92 was used for this analysis to maintain a high stringency condition. A combined test was performed to get a potential region meeting both criteria.

The amino acid sequence analysis was performed by using Peptide-Structure and Plot-Structure programs (PepPlot). PepPlot was written by Drs. Michael Gribskov and John Devereux of the Genetics Computer Group, and it was available through National Institute of Health (NIH, Bethesda, Md.). Peptide-Structure makes secondary structure prediction for a peptide sequence. The predictions measure for antigenicity, flexibility, hydrophobicity and surface probability. Plot-Structure displays these predictions graphically. Using this program the secondary structure of a protein was predicted according to the Chou-Fasman method hydrophilicity according to the Kyte-Doolittle method and antigenic index according to the Jameson-Wolf method.

Expression of 50 kD and 85 kD Homologue Antigen Genes:

After the full sequence analyses of the 50 kD and 85 kD major antigen genes, they were cloned separately by PCR in the expression vector pRSET C (Invitrogen). The advantage of using this expression system was that the foreign prokaryotic genes were expressed in high amounts by the bacteriophage T7 promoter present upstream of the cloned genes. This high level of expression was facilitated by infecting the *E. coli* cells with M13 phage which expressed T7 RNA polymerase. For the cloning of the 50 kD and 85 kD antigen genes, two primers, one at the 5' end of start site of the gene and the other at the 3' end of the termination site of the gene, were selected. While synthesizing these primers, a sequence containing one restriction enzyme site was added eight bases upstream of the 3' end of each primer. Different restriction enzyme sites were added to the two primers so that the amplified product could be cloned in the desired orientation in the multiple cloning site of the vector. The expression of the cloned gene and purification of the expressed protein was done according to the recommendations of the manufacturer (Invitrogen). For easy purification of the expressed protein, a metal binding polyhistidine domain and a site for enterokinase cleavage were also added by the vector sequence to the amino-terminal of the recombinant protein. The expressed recombinant protein could be purified by binding to a nickel ($Ni^{2+}$) charged resin and the extra $Ni^{2+}$ domain could be cleaved using enterokinase.

PCR Amplification of 50 kD and 85 kD Genes:

The complete 50 kD and 85 kD genes were amplified separately from the genomic DNA of the original and variant strain of *E. risticii* by using two modified primers, named as expression cloning primers E.C.P-1 and E.C.P-2 (FIG. 1). The E.C.P-1 ($^{5'}$ CAT AAA ATT TCT AAG ACG AAG GAT CCC TAT GTC$^{3'}$) (SEQ ID NO. 9) was selected from the known sequence of bp upstream of the first methionine codon of the genes. This 33 base primer was modified at base 21 and 22 position by the substitution of two A's in it original sequence with two G's. In the same way, E.C.P-2 ($^{5'}$ GAG AGA AAG TTC CCC GTG TGA ATT CTA GCT AGG$^{3'}$) (SEQ ID NO. 10) was selected from the known sequence 69 bp downstream of the stop codon of the gene. This 33 base primer also was modified at base 21 by introducing another single base A. Amplification of the complete genes (50 kD and 85 kD) by using these two modified primers produced BamH I and EcoR I sites at the extreme 5' and 3' end of the genes respectively.

PCR amplification was accomplished according to the standard protocol described above. As a template, the genomic DNA of the original and variant strains were produced directly from their respective cell culture materials by the PCR lysis method (9). *E. risticii* infected HH cells (1 million) were harvested on day five to seven postinfection and the cell pellet was frozen and thawed three times to rupture the cells. Then 1.0 ml of PCR lysing buffer [50 mM KCl, 10 mM Tris (pH 8.3), 2.5 mM $MgCl_2$, 0.1 mg/ml gelatin, 0.45% Nonidet P40 (Sigma Chemicals), 0.45% Tween 20 and 0.06 mg/ml K ] was added to the ruptured cells and the mixture was incubated at 62° C. for one hour. Finally the mixture was incubated at 95° C. for seven minutes to heat inactivate the protinase K and stored at 4° C. Ten μl of this preparation were used as a template for PCR amplification.

Cloning the PCR Amplified Products in SK(−) Phagemid:

The PCR amplified 50 kD and 85 kD genes were cloned separately in the multiple cloning region of the Sk(−) phagemid (Stratagene) for further sequence analyse. This extra step of cloning and sequencing was accomplished to confirm the correct amplification of the ORF prior to directional cloning in the expression vector pRSET-C.

To accomplish this amplified product (100 μl) was electrophorsed in an agarose gel and the specific DNA band was purified by Geneclean II, following the procedure described above. Fifty μl of this purified DNA were mixed with 6.0 μl of NEBuffer three (New England Biolabs), 3.0 μl of distilled water, and 10 units each of BamH I and EcoR I enzymes (New England Biolabs), and double digested at 37° C. for one hour. The digested product was further purified by Geneclean II and eluted in 25 μl of distilled water. The SK(−) phagemid DNA (1.0 μg) was also double digested and purified separately by using the same technique and eluted in 25 μl of distilled water. The ligation of vector and insert DNA was accomplished by mixing 2.0 μl of double digested phagemid DNA with 4.0 μl of double digested PCR amplified product, 1.0 μl of 10× ligase buffer, 0.1 μl of 10 mM ATP, 1 μl (4 Weiss units) of ligase (Stratagene), and 1.9 μl of distilled water and incubating the mixture at room temperature for 2.5 hours. After the ligation reaction, the *E. coli* XL1-blue competent cells were transformed with 2.0 μl of the ligation mixture by electro-transformation technique and the recombinant clones were selected by plating the transformed cells on LB plates containing 100 μg/ml ampicillin, X-gal, and IPTG. DNA from the recombinant clones were extracted by the minipreparation technique and sequenced to confirm the complete ORF of the 50 kD and 85 kD genes.

Cloning the 50 kD and 85 kD Gene in pRSET-C Expression Vector:

Insert DNAs from the SK(−) recombinant clones of the 50 kD and 85 kD genes, which were confirmed by the sequence analyse, were used for further cloning in pRSET-C expression vector. The selected recombinants were grown in 50 ml of 2×YT media containing 100 μg/ml of ampicillin and recombinant phagemid DNA was extracted by minipreparation following the technique described above. For cloning, 1.0 μg of each pRSET-C plasmid DNA (Invitrogen) and recombinant phagemid DNA were taken separately and double digested with BamH I and EcoR I restriction enzymes in a 60 μl reaction volume. The reaction conditions were the same as described above. After the restriction digestion, both recombinant phagemid and pRSET-C plasmid DNA were electrophoresed in an agarose gel in separate lanes. The specific insert DNA bands and linear pRSET-C plasmid DNA bands were purified from the agarose gel by Geneclean II and eluted separately in 10 μl distilled water. One μl of the prepared vector (0.1 μg of pRSET-C) was mixed with two different 10 fold dilutions of insert DNA to obtain a nearly optimal ratio (2:1::insert:vector). To each of these reaction mixtures, 1.0 μl of 10 mM ATP, 1.0 μl of 1×ligase buffer (Promega), and distilled water were added to a final volume of 9.5 μl. The DNA ends were ligated by incubation at room temperature for 2.5 hours in presence of 2 units (0.5 μl) of T4 DNA ligase (Promega).

The $E.\ coli$ JM 109 [recA1, supE44, endA1, hsdR17, gyrA96, relA1, thiΔ(lac-proAB) F'(traD36, proAB$^+$, lacI$^q$, lacZΔM15)] competent cells were transformed with the ligated DNA by electro-transformation, using the Bio-Rad Gene Pulser apparatus. The competent cells were produced according the procedure described above and 40 μl of cell suspension were added to 2.0 μl of ligation mix. After incubation on ice for one minute, the mixture was transferred into a cold 0.2 cm electroporation cuvette and pulsed with a time constant of four to five milliseconds with a field strength of 12.5 kV/cm. Immediately thereafter 1.0 ml of prewarmed SOC medium was added to the mixture and incubated at 37° C. for one hour in an orbital shaker. About 50 μl aliquots were plated on SOB (2% Bacto trypton, 0.5% Bacto yeast extract, 8.5 mM NaCl, 2.5 mM KCl) plates containing 100 μg/ml ampicillin, X-gal and IPTG. After an overnight incubation at 37° C., single white recombinant colonies were picked up, grown in 5.0 ml of SOB medium with 50 μg/ml of ampicillin and stored at −70° C. in 15% glycerol. Prior to the long term storage, further confirmation of the recombinants was ascertained by BamH I and EcoR I restriction digestion and agarose gel electrophoresis of miniprep DNA from +ve clones.

Expression of Recombinant Proteins in pRSET-C:

Each recombinant protein has different characteristics which can affect optimal expression parameters. To overcome this situation a pilot expression experiment was performed to determine the kinetics of induction for the 50 kD and 85 kD antigen genes. Briefly 2.0 ml of SOB media with 50 μg/ml of ampicillin were inoculated with a single white recombinant $E.\ coli$ colony. The cells were grown at 37° C. overnight in an orbital shaker. The next day 50 ml of SOB media with 50 μg/ml ampicillin was inoculated with 0.2 ml of the overnight culture and grown at 37° C. with vigorous shaking to an OD$_{600}$=0.3. An one ml aliquot of the culture was removed at this time point and centrifuged to pellet the cells. This was considered as the time zero sample and was frozen at −20° C. IPTG was added to the remaining culture to a final concentration of 1.0 mM and the cells were grown in presence of IPTG for an additional hour. After this time period the culture was inoculated with M13/T7 phage (Invitrogen) at an optimal ratio of 5 pfu/cell. The infection was allowed to proceed for another five hours at 37° C. and an one ml aliquot of culture was removed every hour. Each sample was centrifuged and both the supernatant and cell pellet was stored as before.

After all the samples were collected, the each pellet was resuspended in 100 μl of 20 mM phosphate buffer (pH 7.0) and frozen in liquid nitrogen. The frozen samples were thawed again in a 42° C. water bath and this freeze/thaw cycle was repeated an additional three times. Finally the freeze/thaw pellets were centrifuged at 14000×g for 10 minutes in a refrigerated microcentrifuge and the supernatants with the soluble protein fractions were transferred to a fresh tube. The pellets with the insoluble protein fractions were also collected and resuspended in 100 μl of Laemmli buffer. The supernatants were also mixed with equal volumes of Laemmli buffer. Twenty μl of each sample (fractions of both supernatants and pellets) was electrophoresed separately on a 10% SDS polyacrylamide gel, following the identical procedures as described above. The gels were stained with Coomassie Blue and the bands were compared for increasing intensity in the expected size range of the 50 kD and 85 kD antigens to determine the optimal time point of maximum expression.

The large scale extraction and purification of the recombinant proteins were accomplished under denaturing condition. To do this, 50 ml culture of the selected bacteria expressing the recombinant proteins were harvested at the optimal time point of maximum expression. The cells were pelleted by centrifugation at 5,000 rpm for five minutes in a Sorvall SS-34 rotor and the pellets were resuspended in 10 ml of guanidine lysis buffer (6 M guanidine-HCl, 20 mM NaPO$_4$, 500 mM NaCl). The temperature of the buffer was preadjusted to 37° C. for quick lysis of the cells, but to assure that complete lysis was obtained, the cells were rocked at room temperature for additional 10 minutes. To shear the DNA and RNA, the cell lysates were sonicated on ice with three five seconds pulses at a high intensity setting. After the sonication, the insoluble debris were removed from the sheared lysates by centrifugation at 3,000×g for 15 minutes and the clear lysates were stored at −20° C. for further purification with ProBond™ resin columns (Invitrogen).

The recombinant proteins expressed in the pRSET-C vector contained six tandem histidine residues in the amino terminal of the peptides, which had a high affinity for ProBond™ resin. To bind the recombinant proteins in the columns, the resins of the columns were resuspended with 5.0 ml of guanidine lysate of the expressed proteins and rocked on an orbital shaker for 10 minutes at room temperature. The resins were settled by gravity and supernatants were removed carefully. This step was repeated again with another 5.0 ml fresh aliquot of the lysates. After binding the proteins with the resins, the columns were washed twice with denaturing binding buffer (8M urea, 20 mM NaPO$_4$, 500 mM NaCl, pH 7.8), twice with denaturing wash buffer (8M urea, 20 mM NaPO$_4$, 500 mM NaCl, pH 6.0) and twice with the same denaturing wash buffer at pH 5.3. The washings were accomplished by simply resuspending the resins with 4.0 ml of each buffer for two minutes and then separating the resins from the supernatants by gravity. Finally the washed columns were clamped in a vertical position and the cap was snapped off on the lower end. The proteins were eluted from the columns by applying 5.0 ml of denaturing elution buffer (8M urea, 20 mM NaPO$_4$, 500 mM NaCl, pH 4.0). The elutes were collected and dialyzed against 10 mM Tris, pH 8.0, 0.1% Triton X-100 overnight at 4° C. to remove urea, and then analyzed by Western blotting to confirm the specificity of the expressed proteins.

Immunoblot Analysis of $Ehrlichia\ risticii$ Component Antigens of 25D and 90-12 Strains:

The antigenic composition profile of the variant (90-12) strain by Western blotting differed considerably from that of the 25D strain. Previous analysis of the Renografin purified standard (25D strain) indicated the presence of 18 component antigens of which nine (with molecular weights of 110, 70, 68, 55, 51, 50, 33, 28, and 22 kD) were major antigens. $I^{125}$ surface labeling determined that the above antigens were apparent surface antigens. Further analysis by Western blotting with horse, rabbit and mouse antisera confirmed them as major antigens. Though several of these major antigens, namely the 68, 55, 49, and 28 kD, proteins were similar in both strains, the main differences between them were as follows: (i) The 110 and 70 kD antigens were present only in the 25D strain and they did not react with the 90-12 strain antisera. (ii) The 85 kD antigen was present only in the 90-12 strain, but it reacted with the 25D strain antisera. (iii) The 50 kD antigen was present only in the 25D strain and cross reacted with 90-12 strain antisera. (iv) The 55 and 51 kD antigen bands in the 25D strain were well separated, whereas in the 90-12 strain they were close together as a 55/51 kD band. (v) The 33 kD antigen band of each strain showed comparatively less color intensity, with the heterologous antiseras as compared to the homologous antisera.

The Recombinant Antigens and their Identity:

The recombinant clones expressing the partial or complete antigen genes were identified from two different genomic library of *E. risticii* strains. A λ-gt11 recombinant library was constructed with 25D strain genomic DNA and a λ-ZAP recombinant library was constructed with 90-12 strain genomic DNA.

λ-gt11 Recombinants:

The recombinant clones expressing the 50 kD and 70 kD antigen genes of 25D strain was produced previously in λ-gt11 bacteriophage. The 70 kD recombinant was obtained from a library generated by using the partial Hpa II digest of *E. risticii* DNA. The 50 kD recombinant was obtained from the library generated from *E. risticii* DNA subjected to a complete double digestion with Hpa II and HinP I. After identification of the recombinant antigens by the corresponding clone-specific antibodies, further analysis was conducted on 50 kD antigen gene as a part of this study.

λ-ZAP Recombinants:

The genomic expression library in λ-ZAP was generated with Sau3A I digested *E. risticii* DNA. The Sau3A I digested fragments ranged in size from about 400 bp to 2 kb. The efficiency of production of λ-ZAP recombinants was about $10^7$ pfu/μg of λ-ZAP DNA, of which about 8% were non-recombinants. The number of antibody reactive recombinants was about 10 to 14 per $10^4$ pfu. A total of 170 clones reactive with the 90-12 strain antisera were picked up for further analysis. Clone-specific antigen selected antibodies from these clones were prepared and reacted with strips of transblotted 90-12 strain antigens. A comparison of the Western blots of these clone specific antigen selected antibodies with polyclonal 90-12 antisera resulted in the identification of recombinants expressing the 85, 68, 55, 49, 33, 28, and 22 kD antigens. The 51 kD recombinant clone was identified separately from an EcoR I library of 90-12 strain generated in λ-ZAP system. After identification of recombinant antigens from this λ-ZAP library, further study was conducted on the 85 kD antigen.

The Expression Characteristics and Cross Reactivity of 50 kD and 85 kD Recombinant Antigens:

A single recombinant clone expressing the 50 kD recombinant antigen was identified from the λ-gt11 library of the 25D strain, whereas two different recombinant clones expressing the 85 kD recombinant antigen were isolated from λ-ZAP library of the 90-12 strain. Among these two recombinant antigens, the 50 kD antigen was a nonfusion protein, expressed independently of the IPTG induction. Further analysis also revealed that the molecular mass of 50 kD recombinant was identical to that of its native counterpart, indicating expression of the complete protein. Both 85 kD recombinant clones expressed a partial 85 kD antigen with β-galactosidase fusion. They migrated in the gel in conjunction with β-galactosidase, and their expression was dependent on IPTG induction.

It was discussed above that 85 kD and 50 kD antigens were not present in the 25D and 90-12 strains respectively, but these two proteins were cross reacted with each other's strain specific antisera. Further analysis by Western blot also revealed that the recombinant clone expressing only the 50 kD antigen were cross-reactive with antisera raised in mice specifically against the 90-12 strain and the same way vice-versa with 85 kD recombinant clones. These observations clearly indicated that the 50 kD and 85 kD antigens had their corresponding cross-reactive counter part present in both strains. As an attempt to identify these corresponding crossreactive counter parts of the two proteins in each strain, a Western immunoblot was performed with the 50 kD and 85 kD clone specific antibodies. It was observed that the 50 kD clone specific antibody cross reacted with the 85 kD antigen of the 90-12 strain and the 85 kD clone specific antibody cross reacted with the 50 kD antigen of the 25D strain. These results indicated the presence of common cross-reactive epitopes in two different molecular weight proteins which were very strain specific and distinguishable serologically. These two homologous proteins were designated as strain-specific antigens (SSA).

Nucleotide Sequence of 50 kD and 85 kD Recombinant Clones:

The complete sequence of the 50 kD antigen gene reading frame was obtained from a single clone identified in the λ-gt11 library of the 25D strain where as a partial reading frame of the 85 kD antigen gene was obtained from two separate overlapping clones identified in λ-ZAP library of the 90-12 strain. The remaining sequence at the 5' terminus of this gene was obtained later from a PCR amplified segment of the 90-12 genomic DNA. Both the 50 kD and 85 kD insert pieces were subcloned several times to obtain nucleotide sequence information and identify the possible open reading frame of both genes.

Sub clones of 50 kD and 85 kD Recombinants:

EcoR I restriction digestion of the 50 kD λ-gt11 recombinant phage DNA, generated a 3.9 kb insert DNA fragment which was cloned in pBluscript SK(+) phagemid for restriction mapping. Fifteen restriction enzymes (6 base-cutters) were used to determine the presence of restriction sites in the insert DNA of the above pBluscript SK(+) subclone. The Hind III digestion of the recombinant pBluscript SK(+) DNA produced three DNA fragments of 3.5 kb, 2.2 kb and 1135 bp. The 3.5 kb DNA fragment was a plasmid-insert DNA piece, where 565 bp was an insert part and the rest of it was pBluscript SK(+) phagemid. This specific fragment was re-circularized to form a pB50-6.1 subclone. The 2.2 kb and 1135 bp insert fragments were subcloned separately in pBluscript SK(−) phagemid and they were designated as pB50-6.2 and pB50-6.3 respectively. It was difficult to select a primer for downstream sequencing of the pB50-6.2 recombinant clone, due to the presence of direct repeats in the middle of the insert. In order to overcome this situation an internal segment of 826 bp was PCR amplified by using two unique primers: 50-A ($^{5'}$ ATA CTA AAA AGC ATA CTC$^{3'}$) (SEQ ID NO. 11) and 50-B ($^{5'}$ TTC TAC AAG CCC TTT AAA$^{3'}$) (SEQ ID NO. 12). The amplified product was cloned in pCR™ vector and designated as pCR50-6.2.1. The insert piece of the pCR50-6.2.1 recombinant clone was then easily sequenced by using the universal primers of the vector. The presence of direct repeat motifs in the pB50-6.3 recombinant clone produced the same problem as described above and thus the insert piece of this clone was further subcloned in smaller fragments to exploit the advantage of the universal primer sequences for the vector. For this purpose the restriction digestion was performed with Pst I and the generated fragments were cloned separately in pBluscript SK(-) phagemids. Subclones were designated as pB50-6.3.1 and pB50-6.3.2.

The two in vivo excised phagemid clones partially expressing the 85 kD antigen gene were designated as pB85-11 and pB85-17. The insert size of these two clones were 4.5 kB and 1.1 kb respectively. These two clones had 58% overlapping regions with each other and they together covered 84% of the 85 kD gene sequence. The remaining unknown 16% of the 5' region of the gene was separately cloned by PCR from 90-12 genomic DNA, using primers 50-C (5' GAA TGT TCA GCT TTC CGG³') (SEQ ID NO. 13) and 50-D (5' AGC TGT ATC GTT CGT GAG³') (SEQ ID NO. 14) The 1.5 kb amplified product was cloned in pCR™II vector and designated as pCR85-3. The 3' region of the gene was covered by the pB85-11 recombinant clone. The presence of too many direct repeats in this region made the selection of sequencing primers extremely difficult. To overcome this situation the insert segment of this clone was further subcloned in smaller fragments to exploit the advantage of the universal primer sequences for the vector. For this purpose two primers, 85-E (5' GTA TAC TTA CAG ATA GCA C³') (SEQ ID NO. 15) and 50-E (5' GCC GAC AGT ATC ATT AAA C³') (SEQ ID NO. 16), were used to amplify a 876 bp segment, using pB85-11 recombinant DNA as a template. The segment was cloned separately in a pCR™II vector and designated as pCR85-11.1. The insert piece of pCR85-11.1 was restriction digested with Hind III enzyme and as a result of this, two DNA fragments of 4.3 Kb and 443 bp were produced. The 4.3 Kb fragment consisted of 495 bp insert piece and the rest of it (3.8 kb) was the plasmid vector part. This specific fragment was re-circularized to form the pCR85-11.1.1 subclone. The 441 bp fragment consisted of a 383 bp insert piece and a 60 bp plasmid piece. The 441 bp fragment was subcloned at the Hind III site of the pBluscript SK(-) phagemid and designated as pB85-11.1.2. The recombinant DNA of pCR85-11.1.1 was double digested with Hind III and EcoR I. The generated fragments were purified from the agar gel by the Gene clean technique and were further restriction digested with Sau3A I enzyme. The Sau3A I digestion generated two fragments of 317 bp and 247 bp. These fragments had a 9 bp and a 60 bp of plasmid sequence, respectively. These two pieces were separately subcloned at BamH I-EcoR I and BamH I -Hind III sites of pBluscript SK(-) phagemid. They were designated as pB85-11.1.1.1 and pB85-11.1.1.2 respectively.

Sequence of 50 kD and 85 kD Recombinant Clones:

Two vector primers from the opposite direction were used to reveal the complete sequence of a 565 bp insert fragment of the pB50-6.1 recombinant. Sequence analysis of this region did not indicate the presence of any possible reading frames for the 50 kD antigen gene. The composite sequence analysis of the pB50-6.2 and pCR50-6.2.1 recombinants indicated a possible reading frame for the 50 kD antigen gene present in the 2.2 kb fragment of pB50-6.2. The first methionine was located at the 848 bp downstream of the 5' end of this fragment, and the reading frame was continued all the way to it's 3' end. Further sequence analyse of the pB50-6.3.1 and pB50-6.3.2 recombinants revealed the complete sequence profile of the 50 kD antigen gene.

Sequence analysis of the pB85-17 recombinant clone of the 90-12 strain helped to identify the presence of an 1155 bp uninterrupted reading frame of the 85 kD antigen gene. However the fragment did not contain the 5' or 3' end of the gene. Further analysis of this clone revealed a partial sequence homology with the the 50 kD gene of the 25D strain which helped in the selection of the two primers 50-C and 50-D for amplifing the 5' end of the gene. The sequence analysis of the cloned, amplified product (recombinant pCR85-3) revealed the 5' end of the gene. Analyse of the reading frames for subclones pCR85-11.1, pCR85-11.1.1, pCR-11.1.2, pB85-11.1.1.1 and pB85-11.1.1.2 exposed the complete 3' end sequence information of this gene.

Genomic Localization of 50 kD and 85 kD Strain Specific Antigen Homologues:

The presence of a variable number of tandem repeats in the ORFs of both the 50 kD and 85 kD antigen genes, increases the possibility that these genes might be residing in a multigene family category. Thus there may be more than one copy of these genes, with other variable numbers of repeats, present somewhere in the chromosome. To confirm this, a specific probe of 1.5 kb was generated by PCR from the 90-12 genomic DNA following the procedure described above. The primers for amplification were selected in such a way that the amplified product contained a common 697 bp upstream and 180 bp downstream regions from the first methionine of the both 50 kD and 85 kD antigen genes. As a control, the insert segment of two other recombinant clones expressing the 55 kD and 51 kD antigen genes of the 90-12 strain were used as a probe.

The $\alpha^{32}P$ labeled probes were hybridized to the *E. risticii* genomic DNA of the 25D and 90-12 strains. The genomic DNA of both strains were digested with EcoR I and HinD III. Since Sau3A I was the single restriction enzyme used to obtain λ-ZAP recombinants, *E. risticii* DNA of both strains, digested with Sau3A I, were also used for the identification of homologous genomic DNA fragments in these recombinants.

The probes made with the inserts of the 55 kD and 51 kD recombinant clones of the 90-12 strain hybridized with the same-size fragments in each of the three restriction enzyme digests of both strains.

Molecular Structure of *Ehrlichia risticii* SSA Homologues:

The molecular structure of *E. risticii* of the SSA homologues (50 kD and 85 kD) antigen genes were revealed by analyzing the complete nucleotide and amino acid sequences of these two proteins. The complete nucleotide sequences of the genes were constructed from the sequences of individual clones and their subclones. Due to the presence of several direct repeats in these genes, the sequences obtained from the overlapping and adjoining clones and their subclones were further confirmed by amplification and sequencing of those areas directly from the genomic DNA of their respective strains.

Nucleotide Sequence Analysis:

A total of 2632 bp (25D strain) and 3357 bp (90-12 strain) were sequenced in the cloned *E. risticii* DNAs. The nucleotide sequence of the cloned 25D strain consisted of 869 bp of 5' noncoding region, 1617 bp of the ORF, and 146 bp of a 3' noncoding region. The nucleotide sequence of the cloned 90-12 strain consisted of 696 bp of a 5' noncoding region, 2547 bp of the ORF, and 114 bp of a 3'noncoding region. The base compositions of the sequenced DNAs showed high A+T contents (70%), especially in the 5' and 3' noncoding regions (71–80%). This reflects a high A+T-rich genomic DNA in Ehrlichia.

Structure of the 50 kD Antigen Gene:

The nucleotide sequence of the 50 kD antigen gene ORF and 5' and 3' flanking regions were determined and the amino acid sequence was deduced and depicted (FIG. 3, SEQ ID NO: 3 and 4). An ATG translation start site at base pair position 175 and a TAA termination site at base pair position 1792 completed an ORF of 1617 nucleotides encoding 539 amino acids. The deduced sequence of the 50 kD antigen has a calculated molecular mass of 59.829 kD, which is in reasonably close agreement to the size originally observed on SDS-PAGE. The possible transcription initiation site and upstream control region are indicated in FIG. 3. The upstream control region contained nearly perfect −10 and −35 consensus prokaryotic promoter sequences.

The ORF of the 50 kD antigen gene continued uninterrupted at least 66 bp upstream of the proposed ATG translation start site. This 5' region had no ATG codons present which could potentiate another translation initiation site. The further 5' upstream region of this gene had two ATG codons which may be considered as translation initiation sites, but there were two distinct stop signal within 50 bases downstream of these two ATGs. Also, the recombinant in the expression vector produced a full-length product, while lacking the region 5' of the proposed ATG. These two pieces of evidence nullified the possibility of these two ATGs as a translation initiator. The space between the −35 and −10 regions was 17 bp, which is consistent with the optimal spacing (17±1) for prokaryotic promoters. The sequence GAAAAA at 7 bp upstream from the start codon was identified as a potential ribosome-binding site for m-RNA translation.

The non-coding region downstream of the translation termination site was a 143 bp stretch containing inverted repeats bordered by a thymine rich region, resembling prokaryotic rho-independent transcription terminators. These features are denoted in FIG. 3.

Structure of the 85 kD Antigen Gene:

The nucleotide sequence of the 85 kD antigen gene ORF and 5' and 3' flanking regions were determined and the amino acid sequence was deduced (FIG. 2, SEQ ID NO: 5 and 6). An ATG translation start site at base pair position 175 and a TAA termination site at base pair position 2722 completed an ORF of 2547 nucleotides encoding 849 amino acids. The deduced sequence of the 85 kD antigen has a calculalated molecular mass of 94.333 kD, which is in reasonably close agreement to the size originally observed on SDS-PAGE. The possible transcription initiation site and upstream control region are indicated in FIG. 2. The upstream control region, the translation start site, and first 178 bp after the first ATG were almost identical with the 50 kD antigen gene sequence. The ORF of 85 kD antigen gene continued uninterrupted at least 66 bp upstream of the proposed ATG translation start site. Like the 50 kD antigen gene sequence, this 5' region had no ATG codons present which could potentiate another translation initiation site, and it did not affect the full-length expression of the 85 kD antigen, as the recombinant expression vector produced a full-length product while lacking the region 5' of the proposed ATG. The proposed ribosome-binding site GAAAAA was present 7 bp upstream from the start codon.

The non-coding region downstream of the translation termination site was a 112 bp stretch containing inverted repeats bordered by a thymine rich region, resembling prokaryotic rho-independent transcription terminators. These features are denoted in FIG. 2.

Repeat Motifs and Their Nature in 50 kD and 85 kD SSA Homologues:

The DNA sequence analyse of the 50 kD and 85 kD antigen genes revealed the presence of several direct repeats in both genes. The frequency of these repeats were more in middle of the genes and many of these repeats were identical in both genes. All these identical repeats coded for same amino acids but the position and the frequency of repetition were quite different in both genes.

| Type of Repeats | Repeat Sequence | Repeated from Base |
|---|---|---|
| I | (SEQ ID NO. 17) AAAGAAATACT | 957, 1434, 777, 1287, 1353, 648. |
| II | (SEQ ID NO. 18) CAAATACTCAC | 807, 1356, 651, 1290, 1383. |
| III | (SEQ ID NO. 19) AAATTTAAAGA | 978, 1242, 852, 1110, 915. |
| IV | (SEQ ID NO. 20) CTAAAGAGAT | 510, 1017, 891, 1149. |
| V | (SEQ ID NO. 21) AAAGACATACT | 501, 1071 |
| VI | (SEQ ID NO. 22) TTTAAAGAGCT | 342, 1113. |
| VII | (SEQ ID NO. 23) ATTTTTTATAA | 75, 119. |
| VIII | (SEQ ID NO. 24) AACTTTAAAGG | 408, 1179. |
| IX | (SEQ ID NO. 25) AAGTTTAAAGA | 339, 1584. |
| X | (SEQ ID NO. 26) TACTCACTAAT | 457, 1504. |
| XI | (SEQ ID NO. 27) ACTTTAAAAAA | 669, 1309. |
| XII | (SEQ ID NO. 28) ATAAGTTTAAA | 237, 288 |

Table 1. Repeat locations and sequences along the 50 kD antigen gene. Analyses were conducted on the 11-base repeats. There were 12 different types of 11-base repeats present in the complete sequence of the gene. A total of thirty-four 11-base direct repeats were identified in the gene.

Repeats in the 50 kD Gene:

There were a total of 97 repeats present in the 50 kD antigen gene sequence. These repeats were not totally identical in their lengths and sequences. They were first categorized according to their lengths and then, under the same lengths they were grouped according to their sequence profiles. The minimum length of these repeats was 10 bases, whereas the maximum length was 38 bases. The result of these Analyses are represented in Table 1.

Repeats in the 85 kD Gene:

The structures of repeats in the 85 kD antigen gene were almost identical to the 50 kD antigen gene. There are a total of 356 repeats present in this gene sequence. As for the 50 kD antigen gene, these repeats were categorized according to their lengths and then, under the same length, they were grouped according to their sequence profiles. The maximum and minimum lengths of these repeats were 55 and 10 bases respectively. As with the 50 kD antigen gene the 11-mer repeats were also abundant in the complete sequence of the 85 kD antigen gene, and they also were further analyzed for their specific positions in the sequence. The results of these analyses are presented in Table 2.

| Type of Repeats | Repeat Sequence | Repeated From Base. |
|---|---|---|
| I | (SEQ ID NO. 29) ATACTTACAGA | 652, 1963, 1300, 901, 832, 385, 2260, 1729, 316. |
| II | (SEQ ID NO. 30) AAATTTAAAGA | 1984, 2116, 1852, 1390, 1252, 853, 784, 1915. |
| III | (SEQ ID NO. 31) CTAAAAGAGAT | 1891, 2023, 1429, 892, 760, 376, 1228. |
| IV | (SEQ ID NO. 32) AAAGAAATACT | 1696, 1567, 1165, 2227, 1030, 2161, 646. |
| V | (SEQ ID NO. 33) TACTTACAGAT | 1064, 1964, 834, 902, 1301, 1730, 2261. |
| VI | (SEQ ID NO. 34) AAAGACATACT | 310, 1945, 1351, 1282, 883, 814, 367. |
| VII | (SEQ ID NO. 35) ACAGCTAAAGA | 2275, 2302, 1771, 1744, 2302, 1159. |
| VIII | (SEQ ID NO. 36) TTTAAAGAACT | 1393, 2515, 2185, 856, 1323, 339. |
| IX | (SEQ ID NO. 37) GAAATACTTAC | 2164, 2257, 641, 1168, 1726. |
| X | (SEQ ID NO. 38) AGCACTGGTAA | 1975, 2005, 1381, 844, 1312. |
| XI | (SEQ ID NO. 39) GATAAATTTAA | 1912, 2380, 781, 1249, 1849. |
| XII | (SEQ ID NO. 40) CTTATAGAAAG | 934, 1333, 865, 349, 550. |
| XII | (SEQ ID NO. 41) GAAATACTCAC | 676, 2230, 1699, 1570, 1033. |
| XIV | (SEQ ID NO. 42) ACCGGTAACTT | 532, 916, 2230, 1699, 1570, 1033. |
| XV | (SEQ ID NO. 43) ATGCAACAAAA | 2204, 2621, 1007. |
| XVI | (SEQ ID NO. 44) GCTAAAGAAGT | 1189, 2278, 1747. |
| XVII | (SEQ ID NO. 45) CTTACAGATAA | 904, 2035, 1441. |
| XVIII | (SEQ ID NO. 46) GCAATAACTGG | 733, 1864. |
| XIX | (SEQ ID NO. 47) ATGGTAAGGAC | 494, 746. |
| XX | (SEQ ID NO. 48) ACTTATAGAAG | 417, 1401. |

Table 2. Repeat locations and sequences along the 85 kD antigen gene. Analyse were conducted on the 11-base repeats. There were 20 different types of 11 base repeats in the complete sequence of the gene. A total one hundred and one 11-base direct repeats were identified in the gene.

Analysis of Deduced Amino Acid Sequences of SSA Homologues:

The amino acid sequence analyse of the 50 kD and 85 kD antigen genes indicated a considerable homology between these two SSA homologues. That the identical repeats of these two genes code for the same amino acids, indirectly indicates a conserved region between these two genes. From a comparison of the 32 amino acid sequences encoded in the N-terminal ends of the 50 kD and 85 kD antigens an almost identical signal sequence was identified for both proteins. Only one substitution of leucine for isoleucine occurred at residue 26 of the amino acid sequence in the 90-12 strain. These signal peptides for both strains consist of a polar region and a hydrophobic core, of which the same characteristics are seen in the signal peptides of other prokaryotic cells. The hydrophobic core region is extended from the 16th to 28th residues in the signal sequence. The predicted processing site of the signal peptide is at the bond between the 31st and 32nd amino acids, with isoleucine as the N-terminal amino acid of the mature SSA in both cases.

Amino acid sequence comparison of the SSAs of these two antigenic variants is presented in FIG. 5 (SEQ ID NO: 4 and 6). In these analyses, substitution or the addition of one or several contiguous amino acid residues were identified throughout the molecules, but the significant homology in amino acid sequence of the 50 kD and 85 kD antigen was very pronounced in certain regions of the two molecules. These specific areas were designated as ID (identical domain) I–VIII in FIG. 5. The most interesting feature of these IDs was the unique distribution of domains in the linear amino acid sequence of individual antigens. The domains were positioned one after another (ID I to ID VIII) in the 50 kD antigen, whereas the positioning of the same domains was totally different in the 85 kD antigen. In these ID regions, the similarities in the amino acid sequences between these two individual strains vary from more than 94% to less than 79%.

ID I is the largest identical domain, consisting of 129 amino acids. Here the amino acid sequence of the 50 kD and 85 kD antigens were very similar, and estimated homology is 89.15% (87.08% in nucleotide sequence) with 14 amino acid conversions. The position of this particular domain was the same in primary structures of both the antigens. This domain contained the signal sequence region of the the SSA homologues.

ID II consists of 51 amino acids. When comparing SSA homologues, this particular domain is found further downstream in the 85 kD antigen. Here the estimated homology was 88.24% (89.54% in nucleotide sequence) with six amino acid conversions in between the 50 kD and 85 kD antigens.

ID III consists of 42 amino acids. The estimated homology is 92.85% (92.06% in nucleotide sequence) with 3 amino acid conversions. This particular domain is also found further downstream in the 85 kD antigen as compared to the 50 kD antigen.

ID IV consists of 21 amino acids. Here the estimated homology in amino acid sequence is 90.48% (85.71% in nucleotide sequence) with 2 amino acid conversions. With respect to the 50 kD antigen this particular domain is found further upstream in the 85 kD antigen.

ID V consisted of 39 amino acids. Among all the domains, this area had the minimum homology of 79.49% (80.34% in nucleotide sequence) in SSA homologues. In the 85 kD antigen this domain is found further upstream as compared to the 50 kD antigen.

The ID VI domain region has the maximum homology of 94.55% (93.82% in nucleotide sequence) between the two antigens. Similarly, the ID VII and ID VIII domains possess the high homology. ID VII has 92.11% homology (85.08% in nucleotide sequence) and ID VIII has 94.12% homology (96.73% in nucleotide sequence) in their respective areas of the SSA homologues.

After comparing the position of all the identical domains in SSA homologues it is clear that six domains out of eight are changed with respect to their positions in these antigens. In the 85 kD antigen the domains are further apart from each other as compared to the 50 kD antigen, and these gaps are filled with new sequences. These observations indirectly indicate the generation of more new and different domains in the 85 kD antigen.

Hydropathy Analysis of SSA Homologues:

Hydropathy analysis showed that the SSAs of both strains have alternative hydrophilic and hydrophobic motifs which are characteristic of transmembrane proteins. The hydropathy plot of the 50 kD antigen revealed four major hydrophobic stretches which are sufficient in length and hydrophobicity to serve as transmembrane domains. The largest hydrophobic stretch belongs to the identical domain I, and forms the hydrophobic core region of the predicted signal peptide. The other three hydrophobic stretches are clustered in last 60 amino acids of the C-terminus of the protein. Hydropathy analysis of the 85 kD antigen indicats the presence of at least eight major hydrophobic regions. Any one of these regions can act as a transmembrane domain. Like the the 50 kD antigen, this antigen also possesses the largest hydrophobic region in its identical domain I, and other three hydrophobic regions in the last 60 amino acids of the C-terminus. The other four major hydrophobic regions are distributed between residue200 and residue 410 in the sequence. Hydrophilicity indices for both antigens indicated the presence of many outer membrane domains which may be exposed on the outer surface of the organism or the inner cytoplasomic side of the membrane.

Epitope Analysis of SSA Homologues:

Locating the possible antigenic determinants by analyzing protein amino acid sequences in order to find the point of greatest local hydrophilicity, is a common technique nowadays. This was accomplished by assigning each amino acid a numerical value (hydrophilicity value) and then repetitively averaging those values along the peptide chain. The point of highest local average hydrophilicity was invariably located in, or immediately adjacent to, an antigenic determinant or epitope. Using this technique combined with analysis of the flexibility of proteins, the possible antigenic determinants of the 50 kD and 85 kD antigens were determined. Analysis of the comparative position of these epitopes in the common domains of the 50 kD and 85 kD antigens was critical to the evaluate the presence of possible cross-reactive and strain specific antigenic determinants in the 25D and 90-12 strains.

In order to compare the structural as well as antigenic aspects of the SSA homologues, Chou-Fasman predictions of the secondary structure of both the 50 kD and 85 kD complete antigens were plotted. None of these plots were identical to each other. Those regions predicted to have a high likelihood of antigenicity were also determined by the algorithm of Jameson and Wolf. Several regions of high antigenic indices appeared to be conserved in both the antigens, although their positions and orientations in the secondary structure are quite different. Analysis of antigenicity of the 50 kD indicated nine major areas with high antigenic indices (residues 76-80, 118-122, 274-278, 332-336, 362-366, 478-482, 508-512, 518-522, and 528-532). Among these nine major areas, the first two belong to ID-I; the 3rd one belonged to ID-IV; the 4th and 5th, to ID-VI; and the last four to an unique amino acid sequence region of the 50 kD antigen which had no homology with the 85 kD sequence. Analysis of antigenicity of the 85 kD antigen indicated nine major areas with high antigenic indices (residues 76-80, 108-112, 118-122, 212-216, 246-250, 426-430, 590-595, 622-627, 844-848). Among those nine major areas, the first two belonged to ID-I, and the 3rd, 4th and 5th to ID-IV, ID-V and ID-VI respectively. The last three belonged to an unique amino acid sequence region of the 85 kD antigen which had no homology with the 50 kD antigen sequence. Several regions of high antigenic index in both antigens appeared to be conserved (residues 76-80, 118-122, 274-278, 332-336 in the 50 kD antigen and 76-80, 108-112, 118-122, 212-216, 426-430 in the 85 kD antigen). A high antigenic index region in the 85 kD antigen belonged to ID-V, where as the ID-V in the 50 kD antigen does not possess such type of high antigenic index region. This type of variation in this region of both the 50 kD and 85 kD antigens was predicted because the homology between the ID-V's in SSA homologues was minimum (79.49%) when compared to the other identical domains of these two antigens.

Recombinant Antigens and Their Characteristics:

The complete ORF of the 50 kD and 85 kD antigens were constructed by PCR and cloned in pRSET-C expression vector. The correct ORF of the genes were confirmed by cloning and sequencing the PCR amplified product separately in pBluescript SK(-) phagemids prior to expression.

SK(-) Recombinant Clones of the 50 kD and 85 kD Antigens:

The molecular size of the PCR generated fragments which contained the full length genes of the 50 kD and 85 kD antigens were 1.61 kb and 2.54 kb respectively. They were cloned separately in SK(-) phagemids. The BamH I -EcoR I restriction digestions of the recombinant phagemids generated right size inserts, which were expected from the sequence information for these genes. Sequence analyse of these recombinant inserts confirmed the correct amplification of the SSA genes directly from their respective strains.

pRSET-C Recombinant Clones of the 50 kD and 85 kD Antigens:

Total 18 positive pRSET-C recombinant clones of the 50 kD and 85 kD antigen genes (nine for each gene) were separately analyzed by restriction digestions to confirm the proper transfer of inserts from SK(-) phagemids to pRSET-C expression vectors. All nine positive clones from the 50 kD recombinants were successfully transferred in expression vectors, whereas in the 85 kD group only four of the clones were successfully recombined with the expression vectors. Finally, the complete 50 kD and 85 kD antigens were expressed in the pRSET-C systems. Coomassie Blue staining of expressed proteins indicated that maximum expression was achieved four to five hours after the IPTG induction.

Western Blot Analysis of the 50 kD and 85 kD Expressed Proteins:

The identities of the expressed proteins were established to be the 50 kD and 85 kD antigens by the reactivities of *E. risticii* (25D and 90-12 strains) polyclonal antisera and the 85 kD clone specific antibody with the 50 kD and 85 kD antigens of their respective strains and corresponding expressed proteins. Both the 50 kD and 85 kD antigens migrated anomalously during electrophoresis and appeared to be 9.0 kD smaller than the encoded sizes.

Example 2

Isolation of Strain Specific Surface Antigen Gene of *Ehrlichia risticii* ATCC Type Strain Using the procedures outlined in Example 1, the gene encoding the 50 kDa SSA from the ATCC type strain was isolated. The gene sequence and the amino acid sequence encoded thereby is shown in FIG. 4 (SEQ ID NO: 7 and 8).

Example 3

Challenge Experiments

SUMMARY

To study the role of major antigens of *E. risticii* in protective immune response, we expressed the genes of the 55 kDa, 51 kDa and 85 '50 kDa-strain-specific antigens of the 90-12 85 kDa antigen and 25-D (50 kDa antigen strains in *Escherichia coli*. Mice immunized with these purified recombinant proteins of *E. risticii* developed strong and specific humoral immune response. The recombinant 85 kDa antigen of the 90-12 strain protected mice against challenge infection with both *E. risticii* strains, whereas its homologue from the 25-D strain, the recombinant 50 kDa antigen, protected mice against only the homologous strain challenge, but not against the heterologous 90-12 strain. Sera from mice immunized with the 85- or 50-kDa antigens did not inhibit the replication of cell-free Ehriichia in in vitro neutralization assays. Sera from normal mice and mice immunized with other antigens caused non-specific neutralization of *E. risticii*. Immunoglobulin G from mice immunized with the 51 kDa protein of the 90-12 strain caused partial in vitro neutralization of both strains of *E. risticii*. These studies demonstrate that the 85/50-kDa-strain-specific antigen of *E. risticii* is involved in immunoprotection against PHF.

RESULTS

The protective capabilities of the purified recombinant antigens of *R. risticii* were tested in mice. In a pilot experiment, the 51 kDa, 55 kDa, 85 kDa, and 51+85 kDa antigens of the 90-12 strain were used to immunize the mice. Immunizations were performed by intraperitoneal inoculation of the respective antigen(s). The antibody response of mice to the recombinant antigens was determined by IFA using MM cells infected with the 90-12 strain. The prechallenge serum antibody titers of the different experimental groups are shown in FIG. 6. The antibody titers varied from 1/40 to 1/640. The 85 kDa and 51+81 kDa groups of mice contained higher titers compared to the mice in the 51 kDa and 55 kDa groups. After the challenge infection with the 90-12 strain, the mice in 51, 85, 51+85 kDa, and the 90-12 organism groups did not show any clinical signs up to 21 days post-challenge. The 55 kDa and adjuvant groups showed only mild clinical signs.

Figure 7:
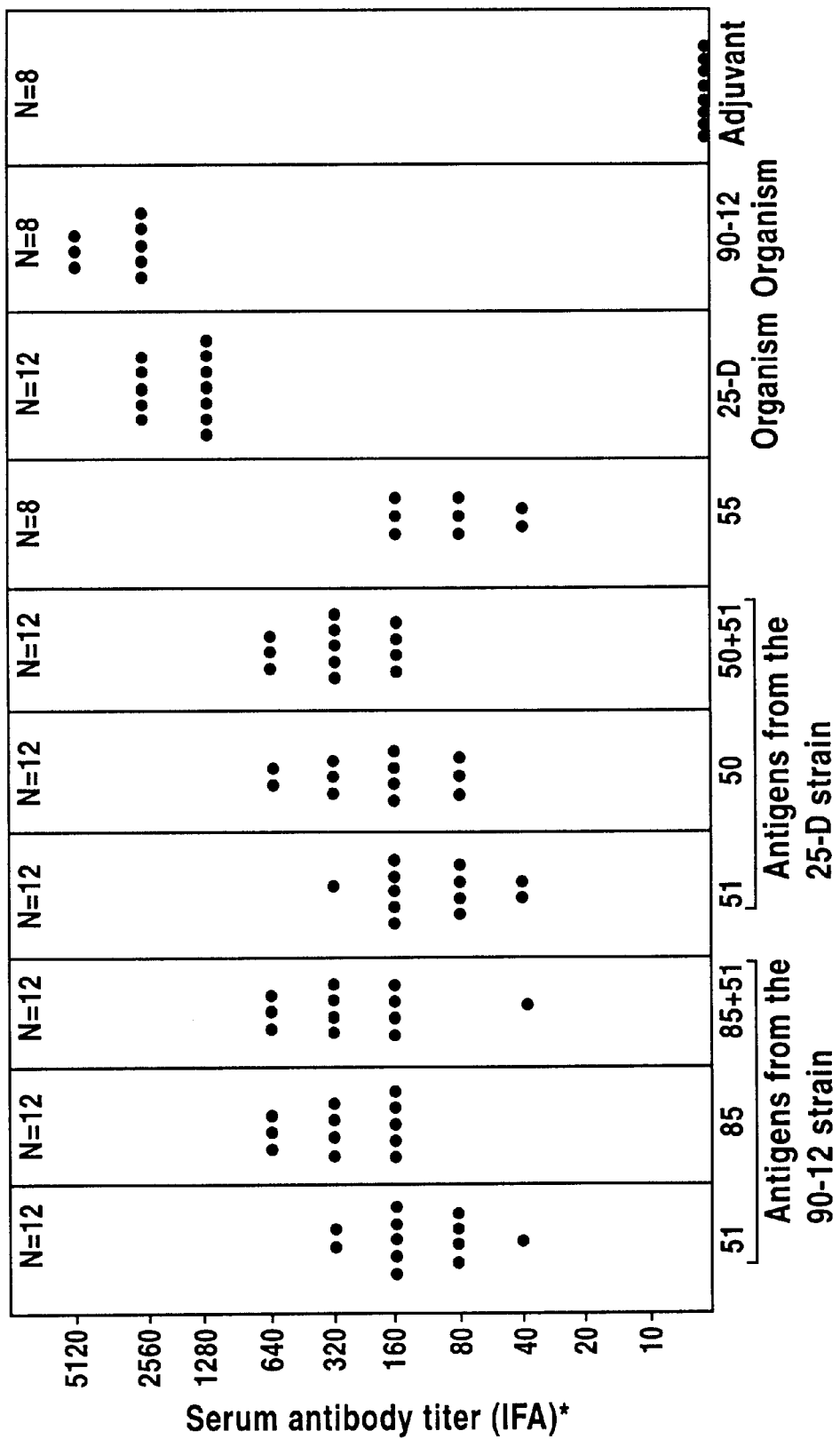
FIG. 7: Pre-challenge serum antibody titers of mice from different groups of experiment 2. Antibody titers were determined by performing IFA using MM cells infected with the 90-12 strain.
Figure 8:
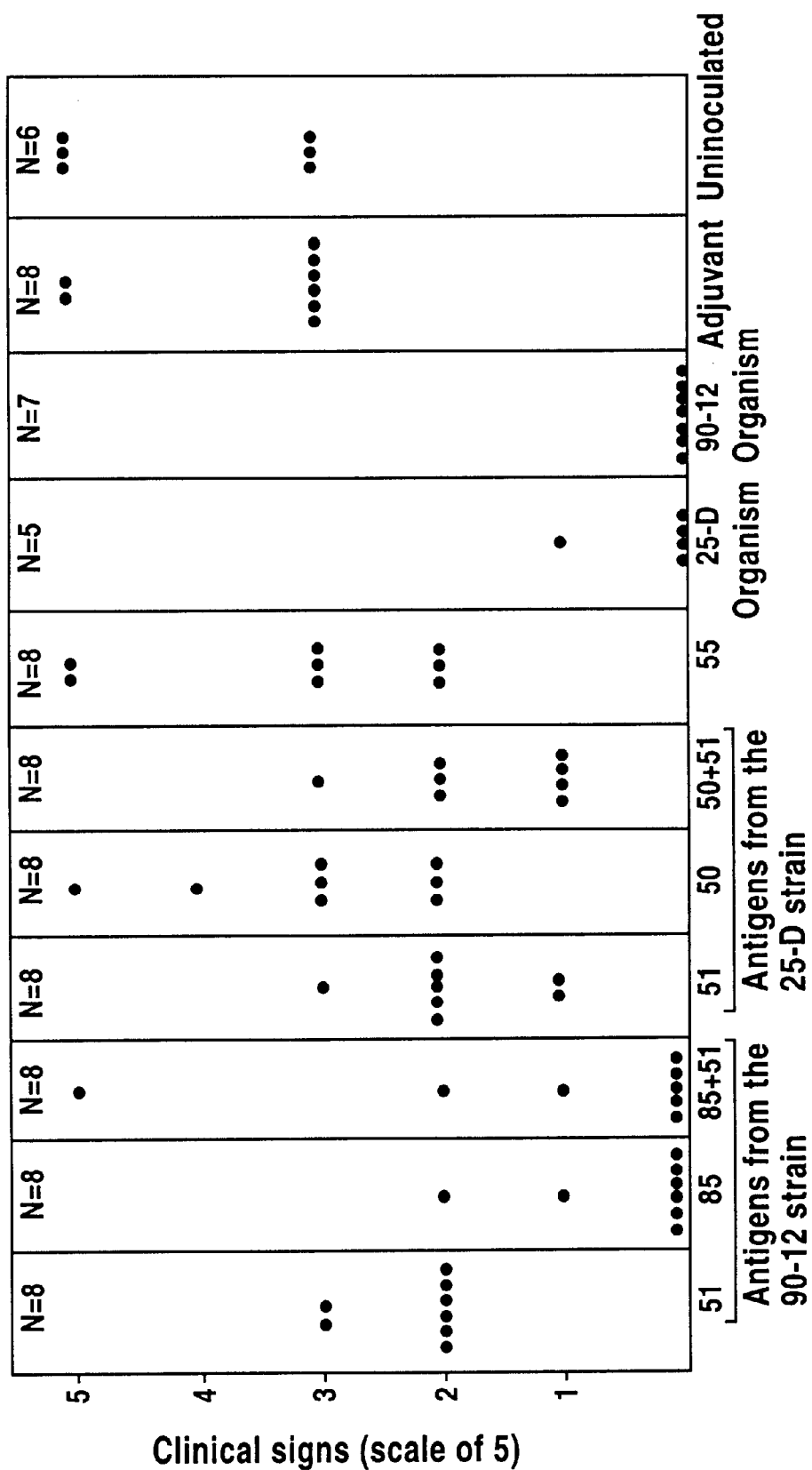
FIG. 8: Post-challenge clinical signs of mice from different groups of experiment 2. Clinical signs were scored on a scale of 0 to 5, with 5 representing the most severe symptoms.

In a second experiment, the 50, 85, 51+85 kDa antigens of the 90-12 strain, and the 51, 50, 51+50 kDa antigens of the 25-D strain were included in the experimental groups. As positive controls, the mice were immunized with the purified organisms of the 90-12 and 25-D strains. The negative controls included the 55 kDa antigen, adjuvant, and uninoculated groups. At the time of the challenge infection, the serum antibody titers of these mice against the 90-12 strain (IFA titers) were obtained (FIG. 7). After challenge infecting with the 90-12 strain, mice in the 85 kDa and 51+85 kDa groups showed significant protection (FIG. 8). In the 85 kDa immunized group, only two out of eight mice suffered mild clinical signs for one and two days respectively. In the 51+85 kDa immunized group one mouse suffered from the infection and it died on day 12 post-challenge. The prechallenge serum antibody titer of this mouse was comparatively lower than the rest of the mice in that group. Mice in the positive control groups were completely protected from the infection. Mice in the negative control groups suffered from the clinical infection. The clinical signs of the mice immunized with either strain's 51 kDa antigen were less severe compared to those of the negative control groups.

In a third experiment, the mice were challenge infected with the 25-D strain. Even in the negative controls, the severity of the infection was less, thus confirming the lower pathogenicity of the 25-D strain. The 55 kDa immunized mice suffered mild clinical signs for only two days. None of the experimental groups showed any clinical signs.

DISCUSSION

The various challenge experiments described herein indicate that the recombinant strain-specific antigens, primarily the 85 kDa antigen of the 90-12 strain or the 90-12 strain itself can be used for immunization purposes. Any variants of *E. risticii* that bind to the antibodies to the 85 kDa antigen of the 90-12 strain may also be used for an attenuated bacterial vaccine. At present, vaccine effectiveness of existing PHF vaccines is low, and it is believed that the present invention can provide a superior vaccine against PHF.

Figure 9:
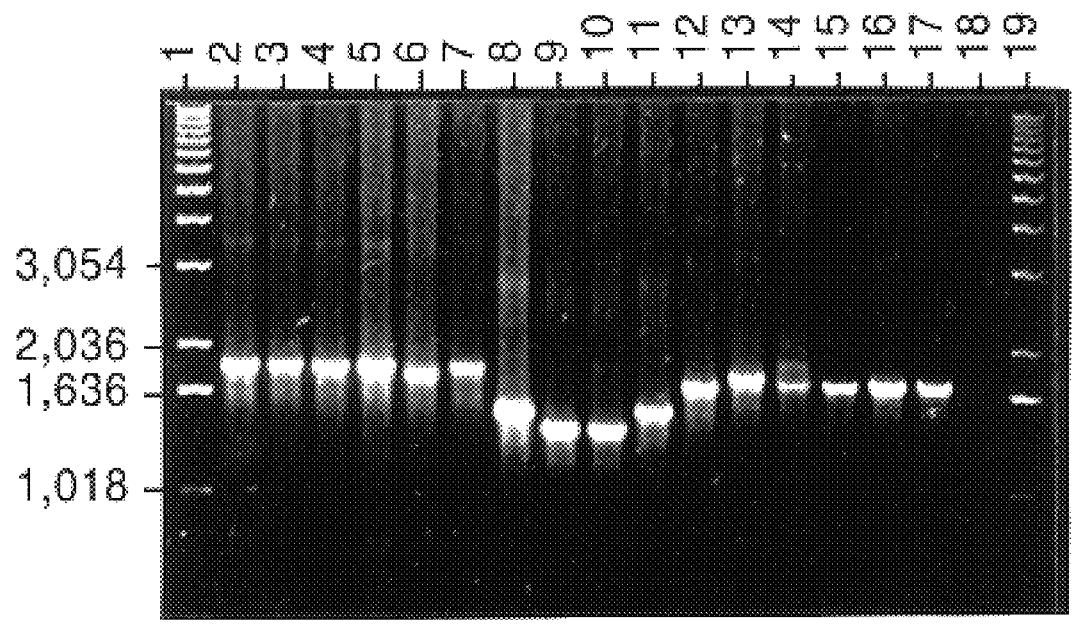
FIG. 9: DAF patterns (size of the amplified DNA in ethidium bromide agarose gel electrophoresis) of field strains of *E. risticii*. Group 1 (1.88 kb): Isolates 94-2, 94-3, 94-24, 90-30 and 25-D strain in lanes 3, 4, 5, 7 and 2. Group 2 (1.86 kb): Isolate 94-27 in lane 6. Group 3 (1.80 kb): Isolate 94-28 in lane 13. Group 4 (1.75 kb): Isolates 94-8, 94-31, 94-37, 94-49 and 94-50 in lanes 12, 13, 15, 16 and 17 which is similar for Illinois/ATCC strain (1.75 kb). Group 5 (1.56 kb): Isolate 64-29 and 90-12 strain in lanes 11 and 8. Group 6 (1.45 kb): Isolates 94-22 and 94-25 in lanes 9 and 10. The DNA from uninfected mouse macrophage cells were used as a control in PCR amplification (lane 18). No visible band in lane 18 indicates the specificity of the primers. Molecular weight markers in lanes 1 and 19.

Also, the antigens disclosed herein can be utilized in diagnostic tests or test kits to diagnose PHF in horses. In addition, the nature of the repeated sequences of SSA can be used to generate intragenic primers to obtain specific DNA amplification finger printing (DAF) to differentiate various strains of *E. risticii*. The DNA amplification finger printing (DAF) of field *E. risticii* isolates are shown in FIG. 9.

The following references are incorporated herein by reference in their entirety:

U.S. Provisional Application Serial No. 60/059,252, filed on Sep. 18, 1997;

Biswas, Biswajit, Molecular basis of antigenic variation of strain-specific surface antigen gene of *Ehriichia risticii* and development of a multiplex PCR assay for differentiation of strains, Ph.D. Thesis, Univ. of Maryland, College Park, Md., USA SO (1996), 186 pp. Avail.: Univ. Microfilms Int., Order No. DA9707569 From: Diss. Abstr. Int., B 1997, 57(10), 6067;

Vemulapalli, Ramesh, Molecular analysis of differences between two strains of *Ehriichia risticii* and identification of protective antigen, Ph.D. Thesis, Univ. of Maryland, College Park, Md., USA, SO (1996) 176 pp., Avail.: Univ. Microfilms Int., Order No. DA9707676, From: Diss. Abstr. Int., B 1997, 57(10), 6125;

Vemulapalli et al, *Veterinary Parisitology*, 76, (1998), pp. 189–202; and

Dutta et al, *Journal of Clinical Microbiology*, Feb. 1998, pp. 506–512.

Obviously, numerous modifications and variations of the present invention are possible in light of the above teachings. It is therefore to be understood that within the scope of the appended claims, the invention may be practiced otherwise than as specifically described herein.

What is claimed is:

1. A method of inducing a protective immune response against *E. risticii* in an animal susceptible to infection by *E. risticii*, the method comprising administering to the animal a purified protein antigen having an amino acid sequence selected from the group consisting of (a) SEQ ID NO: 4, (b) SEQ ID NO: 6 and (c) SEQ ID NO: 8 in an amount to induce a protective immune response against *E. risticii* in the animal.

2. The method of claim 1, wherein the animal is selected from the group consisting of a horse and a mouse.

3. The method of claim 1, wherein the animal is a horse.

* * * * *